(12) United States Patent
Zhang et al.

(10) Patent No.: US 7,238,701 B2
(45) Date of Patent: Jul. 3, 2007

(54) SUBSTITUTED TETRAHYDROBENZO-THIENOPYRIMIDINAMINE COMPOUNDS USEFUL FOR TREATING HYPER-PROLIFERATIVE DISORDERS

(75) Inventors: Chengzhi Zhang, Orange, CT (US); Gaetan H. Ladouceur, Guilford, CT (US); Catherine Brennan, Hamden, NC (US); Brent Chandler, New Haven, CT (US); Julie A. Dixon, Bethany, CT (US); Karl Miranda, Lexington, MA (US); Dongping Fan, North Haven, CT (US); Qingming Zhu, Malden, MA (US); Sharad Verma, New Haven, CT (US); Jacques Dumas, Bethany, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 30 days.

(21) Appl. No.: 10/557,090

(22) PCT Filed: Jul. 23, 2004

(86) PCT No.: PCT/US2004/023698

§ 371 (c)(1),
(2), (4) Date: Nov. 16, 2005

(87) PCT Pub. No.: WO2005/010008

PCT Pub. Date: Feb. 3, 2005

(65) Prior Publication Data

US 2006/0293322 A1 Dec. 28, 2006

Related U.S. Application Data

(60) Provisional application No. 60/490,335, filed on Jul. 24, 2003.

(51) Int. Cl.
*A01N 43/54* (2006.01)
*A61K 31/505* (2006.01)
*C07D 239/00* (2006.01)

(52) U.S. Cl. ...................... 514/267; 544/250

(58) Field of Classification Search ............... None
See application file for complete search history.

(56) References Cited

FOREIGN PATENT DOCUMENTS

| DE | 245 667 A1 | 5/1987 |
| WO | WO 00/39101 A1 | 7/2000 |
| WO | WO 02/088138 A1 | 11/2002 |
| WO | WO 03/040141 A1 | 5/2003 |
| WO | WO 03/057149 A2 | 7/2003 |

OTHER PUBLICATIONS

Ram, Vishnu J., et al., Thieno[2,3-d]pyrimidines as Potential Chemotherapeutic Agents, Journal of Heterocyclic Chemistry, 18(7), 1277-80 (1981).*

* cited by examiner

*Primary Examiner*—Zachary C. Tucker
*Assistant Examiner*—Erich A. Leeser

(57) ABSTRACT

The present invention relates to a compound of Formula (I) and its use in treating lung and breast cancer.

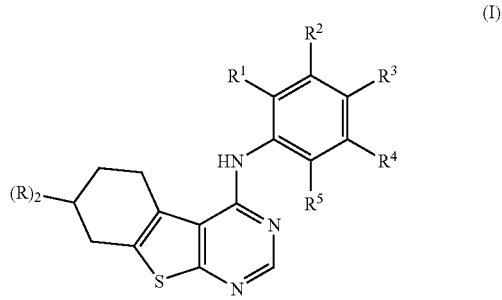

7 Claims, No Drawings

SUBSTITUTED TETRAHYDROBENZOTHIENOPYRIMIDINAMINE COMPOUNDS USEFUL FOR TREATING HYPER-PROLIFERATIVE DISORDERS

This application claims benefit of U.S. Provisional Application Ser. No. 60/490,335, filed Jul. 24, 2003, the contents of which are incorporated herein by reference in their entirety.

FIELD OF THE INVENTION

This invention relates to novel substituted tetrahydrobenzothienopyrimidinamine compounds, pharmaceutical compositions containing such compounds and the use of those compounds and compositions for the treatment of hyper-proliferative disorders.

DESCRIPTION OF THE INVENTION

One embodiment of the present invention relates to a compound of Formula I

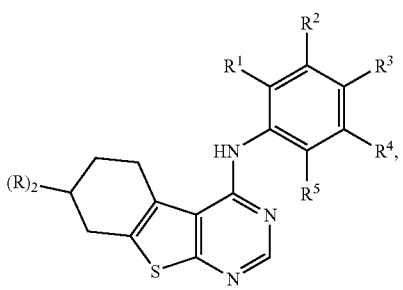

(I)

wherein
R is in each instance selected independently from H, $(C_2–C_6)$alkenyl, $C(O)R^6$, hydroxy, $NR^{8-1}R^{8-1}$, and

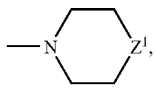

or
R is $(C_1–C_6)$alkyl said alkyl being optionally mono-substituted with $R^7$,
  with the proviso that when one R is H, the other R must be other than H or methyl, and with the further proviso that when one R is hydroxy, the other R must be other than hydroxy;
$R^1$ is selected from H, OH, halo, CN, $NH_2$, $CF_3$, $OCF_3$, $(C_1–C_3)$alkyl, $(C_2–C_3)$alkynyl, and $(C_1–C_3)$alkoxy;
$R^2$ is selected from H, OH, halo, $NH_2$, CN, $CF_3$, $OCF_3$, $(C_1–C_3)$alkyl, $(C_2–C_6)$alkynyl, $(C_1–C_3)$alkoxy,
  $(C_1–C_3)$alkoxy-phenyl where said phenyl is optionally substituted with 1, 2 or 3 substituents each selected independently from $(C_1–C_3)$alkyl, $(C_1–C_3)$alkoxy, halo, $CF_3$, CN, and OH, and
  $(C_1–C_3)$alkoxy-pyridyl, where said pyridyl is optionally substituted with 1, 2 or 3 substituents each selected independently from $(C_1–C_3)$alkyl, $(C_1–C_3)$alkoxy, halo, $CF_3$, CN, and OH,
  O-phenyl optionally substituted with 1, 2 or 3 substituents each selected independently from $(C_1–C_3)$alkyl, $(C_1–C_3)$alkoxy, halo, $CF_3$, CN, and OH;
  O-pyridyl optionally substituted with 1, 2 or 3 substituents each selected independently from $(C_1–C_3)$alkyl, $(C_1–C_3)$alkoxy, halo, $CF_3$, CN, and OH;
$R^3$ is selected from H, OH, halo, $NH_2$, CN, $CF_3$, $OCF_3$, $(C_1–C_3)$alkyl, $(C_2–C_6)$alkynyl,
  $(C_1–C_3)$alkoxy,
  $(C_1–C_3)$alkoxy-phenyl where said phenyl is optionally substituted with 1, 2 or 3 substituents each selected independently from $(C_1–C_3)$alkyl, $(C_1–C_3)$alkoxy, halo, $CF_3$, CN, and OH,
  $(C_1–C_3)$alkoxy-pyridyl, where said pyridyl is optionally substituted with 1, 2 or 3 substituents each selected independently from $(C_1–C_3)$alkyl, $(C_1–C_3)$alkoxy, halo, $CF_3$, CN, and OH,
  O-phenyl optionally substituted with 1, 2 or 3 substituents each selected independently from $(C_1–C_3)$alkyl, $(C_1–C_3)$alkoxy, halo, $CF_3$, CN, and OH,
  O-pyridyl optionally substituted with 1, 2 or 3 substituents each selected independently from $(C_1–C_3)$alkyl, $(C_1–C_3)$alkoxy, halo, $CF_3$, CN, and OH; or
$R^2$ and $R^3$ together with the carbon atoms to which they are attached form a pyrazole, where said pyrazole is optionally substituted with 1 or 2 substituents each selected independently from methyl, ethyl and benzyl or pyridylmethyl, wherein benzyl and pyridylmethyl can optionally be substituted with 1 or 2 substituents each selected independently from methyl, halo, cyano and methoxy;
$R^4$ is selected from H, OH, halo, CN, $CF_3$, $OCF_3$, $NH_2$ $(C_1–C_3)$alkyl, $(C_2–C_6)$alkynyl,
  $(C_1–C_3)$alkoxy, trifluoromethyl, trifluoromethoxy,
  $(C_1–C_3)$alkoxy-phenyl where said phenyl is optionally substituted with 1, 2 or 3 substituents each selected independently from $(C_1–C_3)$alkyl, $(C_1–C_3)$alkoxy, halo, $CF_3$, CN, and OH, and
  $(C_1–C_3)$alkoxy-pyridyl, where said pyridyl is optionally substituted with 1, 2 or 3 substituents each selected independently from $(C_1–C_3)$alkyl,
  $(C_1–C_3)$alkoxy, halo, $CF_3$, CN, and OH,
  O-phenyl optionally substituted with 1, 2 or 3 substituents each selected independently from $(C_1–C_3)$alkyl, $(C_1–C_3)$alkoxy, halo, $CF_3$, CN, and OH;
  O-pyridyl optionally substituted with 1, 2 or 3 substituents each selected independently from $(C_1–C_3)$alkyl, $(C_1–C_3)$alkoxy, halo, $CF_3$, CN, and OH; or
$R^5$ is selected from H, OH, halo, CN, $CF_3$, $OCF_3$, $NH_2$, $(C_1–C_3)$alkyl, $(C_2–C_3)$alkynyl, and $(C_1–C_3)$alkoxy;
$R^6$ is selected from OH, $(C_1–C_6)$alkyl, $(C_1–C_3)$alkoxy, phenyl, pyridyl, $NR^8R^8$,

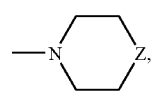

$NH(C_2–C_6)$alkenyl, and
a five membered heterocycle optionally substituted with a substituent selected from OH, $N[(C_1–C_3)alkyl]_2$, and $(C_1–C_3)$alkyl, said alkyl being optionally substituted with a substituent selected from OH, $(C_1–C_3)$alkoxy, and

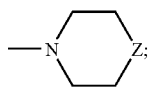

$R^7$ is selected from OH, halo, $(C_1-C_4)$alkoxy, phenoxy optionally substituted with halo or amino, $C(O)R^6$, halo, $NR^8R^8$, imidazolyl, phenyl, indazolyl, aminoindazolyl, $-OS(O)_2C_1-C_3$),

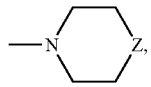

$NHC(O)NR^8R^8$, $NHS(O)_2R^9$, $NHC(O)$-pyrrolidinyl, $NHC(O)$-morpholinyl, and pyrrolidinyl optionally substituted with one or two substituents selected from hydroxy, $(C_1-C_3)$alkoxy, $N[(C_1-C_3)\text{alkyl}]_2$, and $(C_1-C_3)$alkyl optionally mono-substituted with hydroxy or $(C_1-C_3)$alkoxy;

$R^8$ is in each instance selected independently from H, pyridyl,
$(C_1-C_4)$alkyl optionally mono-substituted with hydroxy, $(C_1-C_3)$alkoxy, $-S(O)_2(C_1-C_3)$alkyl, $NR^{10}R^{10}$, or

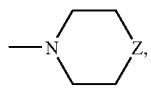

and phenyl optionally substituted with 1, 2, or 3 substituents each independently selected from CN, OH, halo, $CF_3$, $NR^{10}R^{10}$ and $(C_1-C_3)$alkoxy, or

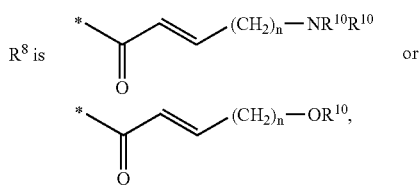

wherein n is a number from 1 to 5 and $R^{10}$ is selected from H and $(C_1-C_3)$alkyl;

$R^{8-1}$ is in each instance selected independently from H, and $(C_1-C_4)$alkyl optionally mono-substituted with $(C_1-C_3)$alkoxy, $NR^{10}R^{10}$, or

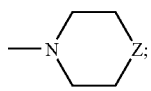

$R^9$ is selected from $(C_1-C_3)$alkyl, pyridyl, thienyl, and phenyl where said phenyl is optionally substituted with 1, 2, or 3 substituents each independently selected from $(C_1-C_3)$alkyl, $(C_1-C_3)$alkoxy, CN, OH, halo, $CF_3$, and $NR^8R^8$;

$R^{10}$ is selected from H and $(C_1-C_3)$alkyl;

Z is selected from $CH_2$, O, S, SO, $SO_2$, and NH, and when Z is NH, H is optionally replaced with pyridyl,
$(C_1-C_3)$alkyl optionally substituted with a substituent selected from hydroxy, $(C_1-C_3)$alkoxy and pyridyl, or phenyl optionally substituted with 1, 2, or 3 substituents each independently selected from $(C_1-C_3)$alkyl, $(C_1-C_3)$alkoxy, CN, halo, $CF_3$, and $NR^8R^8$;

$Z^1$ is selected from $CH_2$, O, S, SO, $SO_2$, and NH, and when $Z^1$ is NH, H is optionally replaced with pyridyl,
$(C_1-C_3)$alkyl optionally substituted with a substituent selected from hydroxy, $(C_1-C_3)$alkoxy and pyridyl, or phenyl optionally substituted with 1, 2, or 3 substituents each independently selected from $(C_1-C_3)$alkyl, $(C_1-C_3)$alkoxy, CN, halo, $CF_3$, and $NR^8R^8$;

or a pharmaceutically acceptable salt or ester thereof, excluding the following compounds:

5,6,7,8-tetrahydro-7-methyl-N-[4-(phenylmethoxy)phenyl]-[1]benzothieno-[2,3-d]pyrimidin-amine, monohydrochloride;

5,6,7,8-tetrahydro-N-(4-methoxyphenyl)-7-methyl-[1]benzothieno[2,3-d]pyrimidin-4-amine, monohydrochloride;

5,6,7,8-tetrahydro-7-methyl-N-[3-(trifluoromethyl)phenyl]-[1]benzothieno-[2,3-d]pyrimidin-4-amine;

N-(3,4-dimethylphenyl)-5,6,7,8-tetrahydro-7-methyl [1]benzothieno-[2,3-d]pyrimidin-4-amine.

The terms have the following meaning throughout:

The term "optionally substituted" means that the moiety so modified may have from none to up to at least the highest number of substituents indicated. The substituent may replace any H atom on the moiety so modified as long as the replacement is chemically possible and chemically stable. When there are two or more substituents on any moiety, each substituent is chosen independently of any other substituent and can, accordingly, be the same or different.

The terms "$(C_1-C_3)$alkyl" and "$(C_1-C_6)$alkyl" mean a linear or branched saturated hydrocarbon radical having from about 1 to about 3 or about 6 C atoms, respectively. Such groups include but are not limited to methyl, ethyl, n-propyl, isopropyl, and the like.

The term "$(C_1-C_3)$alkoxy" means a linear or branched saturated hydrocarbon radical having from about 1 to about 3 C atoms, said radical being attached to an O atom. The O atom is the point of attachment of the alkoxy substituent to the rest of the molecule. Such groups include but are not limited to methoxy, ethoxy, n-propoxy, isopropoxy, and the like.

The term "$(C_1-C_3)$alkoxy-phenyl" means a phenyl group bonded to the alkyl portion of an alkoxy group, as alkoxy is defined above. The phenyl group is bonded to any accessible primary or secondary C atom in the alkyl portion of the alkoxy-phenyl group, and the alkoxy-phenyl group is attached to the rest of the molecule through the O atom.

The term "$(C_1-C_3)$alkoxy-pyridyl" means a pyridyl group bonded to the alkyl portion of an alkoxy group, as alkoxy is defined above. The pyridyl group is bonded to any accessible primary or secondary C atom in the alkyl portion of the alkoxy-pyridyl group, and the alkoxy-pyridyl group is attached to the rest of the molecule through the O atom.

The term "O-phenyl" means a phenyl group bonded to an O atom. The O atom is the point of attachment of the group to the rest of the molecule.

The term "$(C_2-C_6)$alkenyl" means a linear or branched carbon group having from about 2 to about 6 C atoms wherein at least two adjacent C atoms in the alkenyl group are joined by a double bond, with the proviso that when a C atom is double bonded to one adjacent C atom, it must be single bonded to any other adjacent C atom. The alkenyl group is attached to the rest of the molecule through a single bond.

The term "$(C_2-C_6)$alkynyl" means a linear or branched carbon group having from about 2 to about 6 C atoms wherein there is at least one triple bond between two adjacent C atoms in the group with the proviso that when a C atom is triple bonded to one adjacent C atom, it must be single bonded to any other adjacent C atom. The alkynyl group is attached to the rest of the molecule through a single bond.

The term "halo" means Cl, Br, F or I.

When "(O)" is used in a chemical formula, it means an O atom that is double bonded to the atom to which it is attached, but is not further bonded to any other atom, for example, "C(O)" represents a carbonyl group.

The formulae "$N[C_1-C_3)alkyl]_2$", "$NR^8R^8$", "$NR^{8-1}R^{8-1}$" and "$NR^{10}R^{10}$" each means that each of the 2 possible groups attached to the N atom are selected independently from the other so that they may be the same or they may be different.

The term "a five membered heterocycle" means a ring made of 5 atoms, 1, 2 or 3 of which are N with the remaining atoms being C. The heterocycle is saturated, unsaturated or partially saturated. Five membered heterocycles include but are not limited to pyrrolyl, imidazolyl, pyrazolyl, pyrrolidinyl, pyrrolinyl, imidazolidinyl, imidazolinyl, pyrazolidinyl, pyrazolinyl, triazolyl, and the like. The heterocycle is attached to the rest of the molecule through a bond attached to the heterocycle at any position of the heterocyclic radical from which a H atom could conceptually have been removed to create the radical from its corresponding stand-alone molecule.

When a phenyl ring, pyridyl ring, or a five membered heterocycle is attached to the rest of the molecule, the bond to the rest of the molecule is attached to the radical at any position of the radical from which a H could conceptually have been removed to create the radical from its corresponding stand-alone molecule.

When prefixes such as $(C_1-C_4)$ are used before substituents, they mean to indicate the respective number of carbon atoms, in this case 1 to 4.

A * symbol next to a bond denotes the point of attachment in the molecule.

Except for intermediates, chemically unstable compounds are less preferred in the context of the present invention. Chemically unstable here is meant to include conditions to which a compound is exposed when administered to a patient in need thereof, such as acidic or basic conditions of the gastrointestinal tract. For example, a chemically unstable compound would be one where two nitrogen or oxygen substituents are bonded to a single aliphatic carbon atom. Another example of a chemically unstable compound would be one where an alkoxy group is bonded to the unsaturated carbon of an alkene to form an enol ether. Furthermore, an aliphatic carbon atom attached to oxygen may not also bear a chloro, bromo or iodo substituent, and when any alkyl group is attached to O, S, or N, and bears a hydroxyl substituent, then the hydroxyl substituent is separated by at least two carbon atoms from the O, S, or N to which the alkyl group is attached.

Another embodiment of the present invention relates to a compound of Formula (I), wherein
R is selected independently from hydrogen and $C(O)R^6$, or
R is $(C_1-C_6)$alkyl said alkyl being optionally mono-substituted with $R^7$;
with the proviso that when one R is H, the other R must be other than H or methyl;
$R^1$ is selected from H, OH, halo, CN, $NH_2$, $CF_3$, methyl, ethyl, ethynyl, methoxy, and ethoxy;
$R^2$ is selected from H, OH, halo, $NH_2$, CN, $CF_3$, $(C_1-C_3)$alkyl, $(C_2-C_6)$alkynyl,
$(C_1-C_3)$alkoxy,
$(C_1-C_3)$alkoxy-phenyl where said phenyl is optionally substituted with 1, 2 or 3 substituents each selected independently from $(C_1-C_3)$alkyl, $(C_1-C_3)$alkoxy, halo, $CF_3$, CN, and OH, and
$(C_1-C_3)$alkoxy-pyridyl, where said pyridyl is optionally substituted with 1, 2 or 3 substituents each selected independently from $(C_1-C_3)$alkyl, $(C_1-C_3)$alkoxy, halo, $CF_3$, CN, and OH,
O-phenyl optionally substituted with 1, 2 or 3 substituents each selected independently from $(C_1-C_3)$alkyl, $(C_1-C_3)$alkoxy, halo, $CF_3$, CN, and OH;
$R^3$ is selected from H, OH, halo, $NH_2$, CN, $CF_3$, $(C_1-C_3)$alkyl, $(C_2-C_6)$alkynyl,
$(C_1-C_3)$alkoxy,
$(C_1-C_3)$alkoxy-phenyl where said phenyl is optionally substituted with 1, 2 or 3 substituents each selected independently from $(C_1-C_3)$alkyl, $(C_1-C_3)$alkoxy, halo, $CF_3$, CN, and OH,
$(C_1-C_3)$alkoxy-pyridyl, where said pyridyl is optionally substituted with 1, 2 or 3 substituents each selected independently from $(C_1-C_3)$alkyl, $(C_1-C_3)$alkoxy, halo, $CF_3$, CN, and OH,
O-phenyl optionally substituted with 1, 2 or 3 substituents each selected independently from $(C_1-C_3)$alkyl, $(C_1-C_3)$alkoxy, halo, $CF_3$, CN, and OH,
O-pyridyl optionally substituted with 1, 2 or 3 substituents each selected independently from $(C_1-C_3)$alkyl, $(C_1-C_3)$alkoxy, halo, $CF_3$, CN, and OH; or
$R^2$ and $R^3$ together with the carbon atoms to which they are attached form a pyrazole, where said pyrazole is optionally N-substituted with 1 substituent selected from methyl, ethyl and benzyl;
$R^4$ is H;
$R^5$ is H;
$R^6$ is selected from $NR^8R^8$,

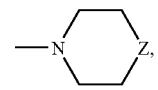

$NH(C_2-C_6)$alkenyl and
a five membered heterocycle optionally substituted with a substituent selected from OH, $N[(C_1-C_3)alkyl]_2$, and $(C_1-C_3)$alkyl, said alkyl being optionally substituted with a substituent selected from OH, $(C_1-C_3)$alkoxy, and

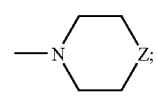

$R^7$ is selected from phenoxy optionally substituted with halo or amino, $NR^8R^8$, imidazolyl, indazolyl, aminoindazolyl,

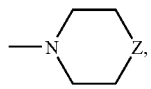

NHC(O)NR$^8$R$^8$, NHS(O)$_2$R$^9$, NHC(O)-pyrrolidinyl, NHC(O)-morpholinyl, and pyrrolidinyl optionally substituted with one substituent selected from (C$_1$–C$_3$)alkoxy, N[(C$_1$–C$_3$)alkyl]$_2$, and (C$_1$–C$_3$)alkyl optionally mono-substituted with (C$_1$–C$_3$)alkoxy;

R$^8$ is in each instance selected independently from H, pyridyl, (C$_1$–C$_4$)alkyl optionally mono-substituted with (C$_1$–C$_3$)alkoxy, —S(O)$_2$(C$_1$–C$_3$)alkyl, NR$^{10}$R$^{10}$, or

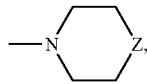

and phenyl optionally substituted with 1, 2, or 3 substituents each independently selected from CN, OH, halo, CF$_3$, NR$^{10}$R$^{10}$ and (C$_1$–C$_3$)alkoxy;

R$^9$ is selected from (C$_1$–C$_3$)alkyl, pyridyl, thienyl, and phenyl where said phenyl is optionally substituted with 1, 2, or 3 substituents each independently selected from (C$_1$–C$_3$)alkyl, (C$_1$–C$_3$)alkoxy, CN, OH, halo, CF$_3$, and NR$^8$R$^8$;

R$^{10}$ is selected from H and (C$_1$–C$_3$)alkyl;

Z is selected from CH$_2$, O, S and NH, and when Z is NH, H is optionally replaced with pyridyl, (C$_1$–C$_3$)alkyl optionally substituted with a substituent selected from hydroxy, (C$_1$–C$_3$)alkoxy and pyridyl, or phenyl optionally substituted with 1, 2, or 3 substituents each independently selected from (C$_1$–C$_3$)alkyl, (C$_1$–C$_3$)alkoxy, CN, halo, CF$_3$, and NR$^8$R$^8$;

or a pharmaceutically acceptable salt or ester thereof, excluding the following compounds:

5,6,7,8-tetrahydro-7-methyl-N-[4-(phenylmethoxy)phenyl]-[1]benzothieno-[2,3-d]pyrimidin-4-amine, monohydrochloride;

5,6,7,8-tetrahydro-N-(4-methoxyphenyl)-7-methyl-[1]benzothieno[2,3-d]pyrimidin-4-amine, monohydrochloride;

5,6,7,8-tetrahydro-7-methyl-N-[3-(trifluoromethyl)phenyl]-[1]benzothieno-[2,3-d]pyrimidin-4-amine;

N-(3,4-dimethylphenyl)-5,6,7,8-tetrahydro-7-methyl[1]benzothieno-[2,3-d]pyrimidin-4-amine.

Another embodiment of the present invention relates to a compound of Formula I, wherein one R is hydrogen and the other R is methyl, ethyl or propyl, said methyl, ethyl or propyl being mono-substituted with R$^7$; and R$^7$ is selected from hydroxy, NR$^8$R$^8$,

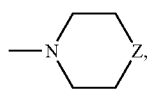

NHC(O)NR$^8$R$^8$, NHS(O)$_2$R$^9$, NHC(O)-pyrrolidinyl, and NHC(O)-morpholinyl.

Another embodiment of the present invention relates to a compound of Formula I of claim 1, wherein R$^3$ is 4-fluorobenzyloxy, 3-fluorobenzyloxy.

Another embodiment of the present invention relates to a compound of Formula I of claim 1, wherein R$^3$ is a dihalogenated phenyl, e.g. wherein halo is fluoro or chloro, such as 3-chloro-4-fluorophenyl.

Another embodiment of the present invention relates to a compound of Formula I of claim 1, wherein R$^3$ is meta-substituted phenyl, such as 3-bromophenyl or 3-ethynylphenyl.

Another embodiment of the present invention relates to a compound of Formula I, wherein R is in each instance selected independently from H, (C$_2$–C$_6$)alkenyl, C(O)R$^6$ and (C$_1$–C$_6$)alkyl said alkyl being optionally mono-substituted with R$^7$, with the proviso that when one R is H, the other R must be other than H;

R$^1$ is selected from H, OH, halo, CN, NH$_2$, CF$_3$, (C$_1$–C$_3$)alkyl, and (C$_1$–C$_3$)alkoxy;

R$^2$ is selected from H, OH, halo, NH$_2$, CN, CF$_3$, (C$_1$–C$_3$)alkyl, (C$_2$–C$_6$)alkynyl, (C$_1$–C$_3$)alkoxy, (C$_1$–C$_3$)alkoxy-phenyl where said phenyl is optionally substituted with 1, 2 or 3 substituents each selected independently from (C$_1$–C$_3$)alkyl, (C$_1$–C$_3$)alkoxy, halo, CF$_3$, CN, and OH, and O-phenyl optionally substituted with 1, 2 or 3 substituents each selected independently from (C$_1$–C$_3$)alkyl, (C$_1$–C$_3$)alkoxy, halo, CF$_3$, CN, and OH;

R$^3$ is selected from H, OH, halo, NH$_2$, CN, CF$_3$, (C$_1$–C$_3$)alkyl, (C$_2$–C$_6$)alkynyl, (C$_1$–C$_3$)alkoxy, (C$_1$–C$_3$)alkoxy-phenyl where said phenyl is optionally substituted with 1, 2 or 3 substituents each selected independently from (C$_1$–C$_3$)alkyl, (C$_1$–C$_3$)alkoxy, halo, CF$_3$, CN, and OH, and O-phenyl optionally substituted with 1, 2 or 3 substituents each selected independently from (C$_1$–C$_3$)alkyl, (C$_1$–C$_3$)alkoxy, halo, CF$_3$, CN, and OH;

R$^4$ is selected from H, OH, halo, CN, CF$_3$, NH$_2$ (C$_1$–C$_3$)alkyl, (C$_2$–C$_6$)alkynyl, (C$_1$–C$_3$)alkoxy, (C$_1$–C$_3$)alkoxy-phenyl where said phenyl is optionally substituted with 1, 2 or 3 substituents each selected independently from (C$_1$–C$_3$)alkyl, (C$_1$–C$_3$)alkoxy, halo, CF$_3$, CN, and OH, and O-phenyl optionally substituted with 1, 2 or 3 substituents each selected independently from (C$_1$–C$_3$)alkyl, (C$_1$–C$_3$)alkoxy, halo, CF$_3$, CN, and OH;

R$^5$ is selected from H, OH, halo, CN, CF$_3$, NH$_2$, (C$_1$–C$_3$)alkyl, and (C$_1$–C$_3$)alkoxy;

R$^6$ is selected from OH, (C$_1$–C$_6$)alkyl, (C$_1$–C$_3$)alkoxy, phenyl, pyridyl, NR$^8$R$^8$,

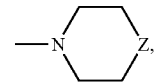

NH(C$_2$–C$_6$)alkenyl, and a five membered heterocycle optionally substituted with a substituent selected from OH, N[(C$_1$–C$_3$)alkyl]$_2$, and (C$_1$–C$_3$)alkyl, said alkyl being optionally substituted with a substituent selected from OH, (C$_1$–C$_3$)alkoxy, and

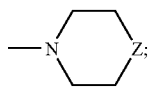

R$^7$ is selected from OH, (C$_1$–C$_4$)alkoxy, C(O)R$^6$, halo, NR$^8$R$^8$, imidazolyl, phenyl,

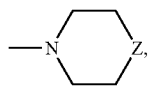

NHC(O)NR$^8$R$^8$, NHS(O)$_2$R$^9$, NHC(O)-pyrrolidinyl, NHC(O)-morpholinyl, and
pyrrolidinyl optionally substituted with one substituent selected from (C$_1$–C$_3$)alkoxy,
N[(C$_1$–C$_3$)alkyl]$_2$, and (C$_1$–C$_3$)alkyl optionally mono-substituted with (C$_1$–C$_3$)alkoxy;
R$^8$ is in each instance selected independently from H, pyridyl,
(C$_1$–C$_4$)alkyl optionally mono-substituted with (C$_1$–C$_3$) alkoxy, S(O)$_2$(C$_1$–C$_3$)alkyl, NR$^{10}$R$^{10}$, or

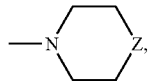

and
phenyl optionally substituted with 1, 2, or 3 substituents each independently selected from CN, OH, halo, CF$_3$, NR$^{10}$R$^{10}$ and (C$_1$–C$_3$)alkoxy;
R$^9$ is selected from (C$_1$–C$_3$)alkyl, pyridyl, thienyl, and phenyl where said phenyl is optionally substituted with 1, 2, or 3 substituents each independently selected from (C$_1$–C$_3$)alkyl, (C$_1$–C$_3$)alkoxy, CN, OH, halo, CF$_3$, and NR$^8$R$^8$;
R$^{10}$ is selected from H and (C$_1$–C$_3$)alkyl;
Z is selected from CH$_2$, O, S and NH, and
when Z is NH, H is optionally replaced with pyridyl, (C$_1$–C$_3$)alkyl optionally substituted with a substituent selected from (C$_1$–C$_3$)alkoxy and pyridyl, or
phenyl optionally substituted with 1, 2, or 3 substituents each independently selected from (C$_1$–C$_3$)alkyl, (C$_1$–C$_3$)alkoxy, CN, halo, CF$_3$, and NR$^8$R$^8$;

or a pharmaceutically acceptable salt or ester thereof, excluding the following compounds:
5,6,7,8-tetrahydro-7-methyl-N-[4-(phenylmethoxy)phenyl]-[1]benzothieno-[2,3-d]pyrimidin-4-amine, monohydrochloride;
5,6,7,8-tetrahydro-N-(4-methoxyphenyl)-7-methyl-[1]benzothieno[2,3-d]pyrimidin-4-amine, monohydrochloride;
5,6,7,8-tetrahydro-7-methyl-N-[3-trifluoromethyl)phenyl]-[1]benzothieno-[2,3-d]pyrimidin-4-amine;
N-(3,4-dimethylphenyl)-5,6,7,8-tetrahydro-7-methyl [1]benzothieno-[2,3-d]pyrimidin-4-amine.

In another embodiment, the present invention relates to a method of treating a hyper-proliferative disorder comprising the administration to a patient in need thereof of an effective amount of a compound of Formula I.

In another embodiment, the present invention relates to a method of treating a hyper-proliferative disorder comprising the administration to a patient in need thereof of an effective amount of a compound of Formula I

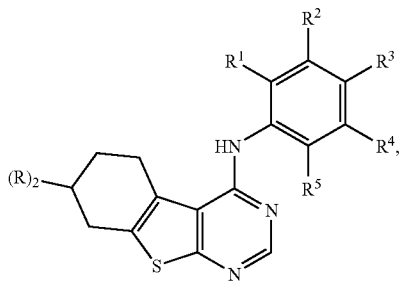

(I)

wherein
R is in each instance selected independently from H, (C$_2$–C$_6$)alkenyl, C(O)R$^6$ and
(C$_1$–C$_6$)alkyl said alkyl being optionally mono-substituted with R$^7$,
with the proviso that when one R is H, the other R must be other than H;
R$^1$ is selected from H, OH, halo, CN, NH$_2$, CF$_3$, (C$_1$–C$_3$) alkyl, and
(C$_1$–C$_3$)alkoxy;
R$^2$ is selected from H, OH, halo, NH$_2$, CN, CF$_3$, (C$_1$–C$_3$) alkyl, (C$_2$–C$_6$)alkynyl,
(C$_1$–C$_3$)alkoxy,
(C$_1$–C$_3$)alkoxy-phenyl where said phenyl is optionally substituted with 1, 2 or 3 substituents each selected independently from (C$_1$–C$_3$)alkyl, (C$_1$–C$_3$)alkoxy, halo, CF$_3$, CN, and OH, and
O-phenyl optionally substituted with 1, 2 or 3 substituents each selected independently from (C$_1$–C$_3$)alkyl, (C$_1$–C$_3$)alkoxy, halo, CF$_3$, CN, and OH;
R$^3$ is selected from H, OH, halo, NH$_2$, CN, CF$_3$, (C$_1$–C$_3$) alkyl, (C$_2$–C$_6$)alkynyl,
(C$_1$–C$_3$)alkoxy,
(C$_1$–C$_3$)alkoxy-phenyl where said phenyl is optionally substituted with 1, 2 or 3 substituents each selected independently from (C$_1$–C$_3$)alkyl, (C$_1$–C$_3$)alkoxy, halo, CF$_3$, CN, and OH, and
O-phenyl optionally substituted with 1, 2 or 3 substituents each selected independently from (C$_1$–C$_3$)alkyl, (C$_1$–C$_3$)alkoxy, halo, CF$_3$, CN, and OH;
R$^4$ is selected from H, OH, halo, CN, CF$_3$, NH$_2$ (C$_1$–C$_3$) alkyl, (C$_2$–C$_6$)alkynyl,
(C$_1$–C$_3$)alkoxy,
(C$_1$–C$_3$)alkoxy-phenyl where said phenyl is optionally substituted with 1, 2 or 3 substituents each selected independently from (C$_1$–C$_3$)alkyl, (C$_1$–C$_3$)alkoxy, halo, CF$_3$, CN, and OH, and
O-phenyl optionally substituted with 1, 2 or 3 substituents each selected independently from (C$_1$–C$_3$)alkyl, (C$_1$–C$_3$)alkoxy, halo, CF$_3$, CN, and OH;
R$^5$ is selected from H, OH, halo, CN, CF$_3$, NH$_2$, (C$_1$–C$_3$) alkyl, and (C$_1$–C$_3$)alkoxy;

$R^6$ is selected from OH, $(C_6-C_6)$alkyl, $(C_1-C_3)$alkoxy, phenyl, pyridyl, $NR^8R^8$,

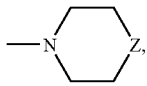

$NH(C_2-C_6)$alkenyl, and
a five membered heterocycle optionally substituted with a substituent selected from OH, $N[(C_1-C_3)$alkyl$]_2$, and $(C_1-C_3)$alkyl, said alkyl being optionally substituted with a substituent selected from OH, $(C_1-C_3)$alkoxy, and

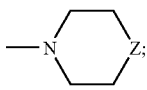

$R^7$ is selected from OH, $(C_1-C_4)$alkoxy, $C(O)R^6$, halo, $NR^8R^8$, imidazolyl, phenyl,

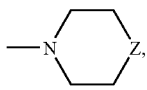

$NHC(O)NR^8R^8$, $NHS(O)_2R^9$, NHC(O)-pyrrolidinyl, NHC(O)-morpholinyl, and
pyrrolidinyl optionally substituted with one substituent selected from $(C_1-C_3)$alkoxy,
$N[(C_1-C_3)$alkyl$]_2$, and $(C_1-C_3)$alkyl optionally mono-substituted with $(C_1-C_3)$alkoxy;
$R^8$ is in each instance selected independently from H, pyridyl,
$(C_1-C_4)$alkyl optionally mono-substituted with $(C_1-C_3)$alkoxy, $S(O)_2(C_1-C_3)$alkyl, $NR^{10}R^{10}$, or

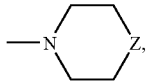

and
phenyl optionally substituted with 1, 2, or 3 substituents each independently selected from CN, OH, halo, $CF_3$, $NR^{10}R^{10}$ and $(C_1-C_3)$alkoxy;
$R^9$ is selected from $(C_1-C_3)$alkyl, pyridyl, thienyl, and phenyl where said phenyl is optionally substituted with 1, 2, or 3 substituents each independently selected from $(C_1-C_3)$alkyl, $(C_1-C_3)$alkoxy, CN, OH, halo, $CF_3$, and $NR^8R^8$;

$R^{10}$ is selected from H and $(C_1-C_3)$alkyl;
Z is selected from $CH_2$, O, S and NH, and
when Z is NH, H is optionally replaced with pyridyl,
$(C_1-C_3)$alkyl optionally substituted with a substituent selected from $(C_1-C_3)$alkoxy and pyridyl, or
phenyl optionally substituted with 1, 2, or 3 substituents each independently selected from $(C_1-C_3)$alkyl, $(C_1-C_3)$alkoxy, CN, halo, $CF_3$, and $NR^8R^8$;

or a pharmaceutically acceptable salt or ester thereof, excluding the following compounds:
5,6,7,8-tetrahydro-7-methyl-N-[4-(phenylmethoxy)phenyl]-[1]benzothieno-[2,3-d]pyrimidin-4-amine, monohydrochloride;
5,6,7,8-tetrahydro-N-(4-methoxyphenyl)-7-methyl-[1]benzothieno[2,3-d]pyrimidin-4-amine, monohydrochloride;
5,6,7,8-tetrahydro-7-methyl-N-[3-(trifluoromethyl)phenyl]-[1]benzothieno-[2,3-d]pyrimidin-4-amine;
N-(3,4-dimethylphenyl)-5,6,7,8-tetrahydro-7-methyl[1]benzothieno-[2,3-d]pyrimidin-4-amine.

In another embodiment, the present invention relates to a process for making a compound of formula (I), wherein
a compound of formula (II)

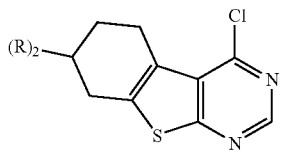

(II)

wherein R has the meaning indicated above,
is reacted with a compound of formula (III)

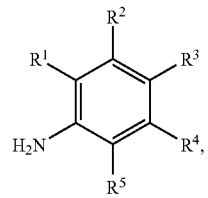

(III)

wherein $R^1$ to $R^5$ have the meaning indicated above, preferably in the presence of an acid.

Representative compounds of Formula I are described in Table 1 below.

TABLE 1

| Ex. No. | Structure | LCMS RT (min)ᵃ or TLC $R_f$ [solvent] | LCMS Ion $[M + H]^+$ |
|---|---|---|---|
| 1 | 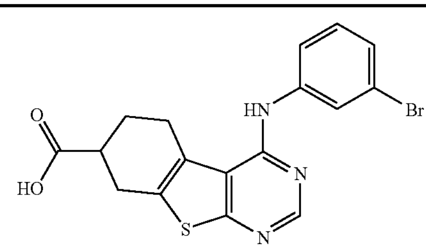 | 2.83 | 404 |

TABLE 1-continued

| Ex. No. | Structure | LCMS RT (min)[a] or TLC R_f [solvent] | LCMS Ion [M + H]+ |
|---|---|---|---|
| 2 | 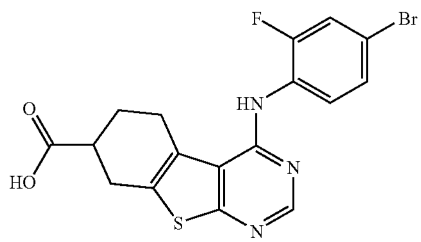 | 3.00 | 424 |
| 3 | 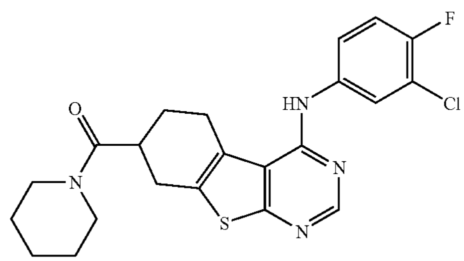 | 3.12 | 446 |
| 4 | 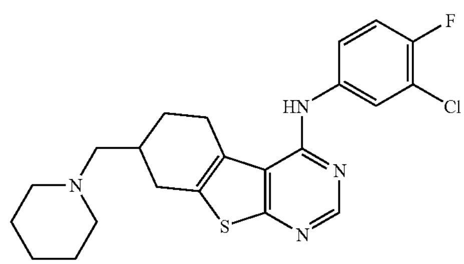 | 2.26 | 431 |
| 5 | 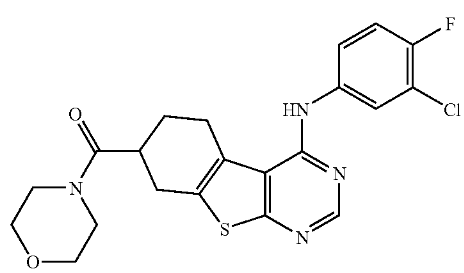 | 2.68 | 447 |
| 6 | 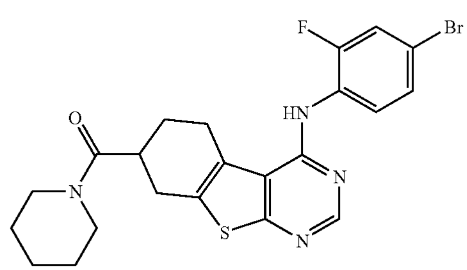 | 3.39 | 489 |

TABLE 1-continued

| Ex. No. | Structure | LCMS RT (min)a or TLC Rf [solvent] | LCMS Ion [M + H]+ |
|---|---|---|---|
| 7 | 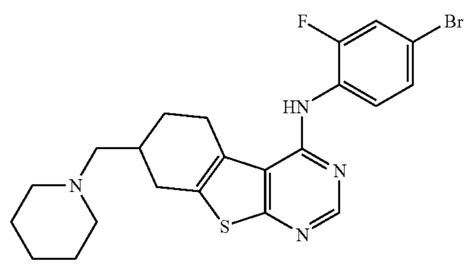 | 2.32 | 475 |
| 8 | 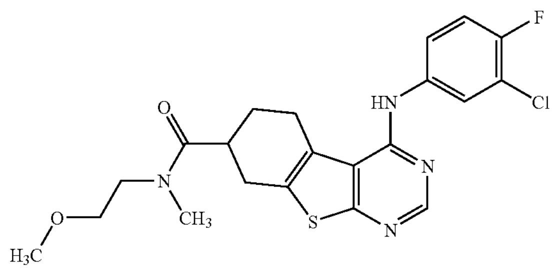 | 2.78 | 449 |
| 9 | 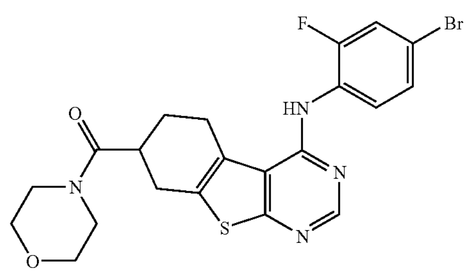 | 2.80 | 491 |
| 10 | 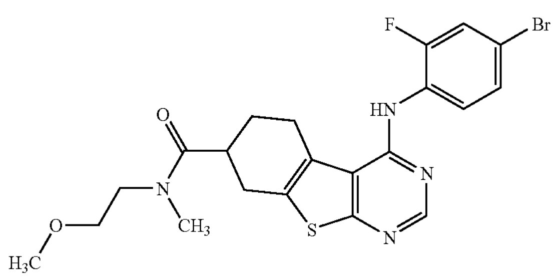 | 2.91 | 493 |
| 11 | 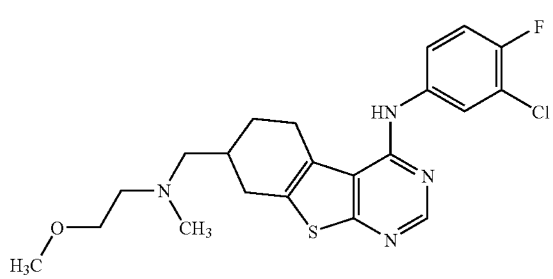 | 2.21 | 435 |

TABLE 1-continued
| Ex. No. | Structure | LCMS RT (min)[a] or TLC R_f [solvent] | LCMS Ion [M + H]+ |
|---|---|---|---|
| 12 | 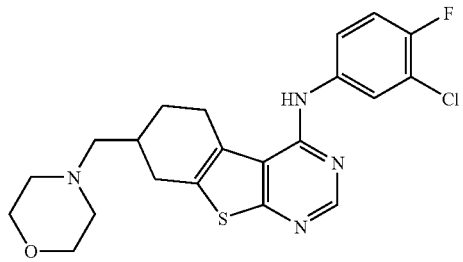 | 2.16 | 433 |
| 13 | 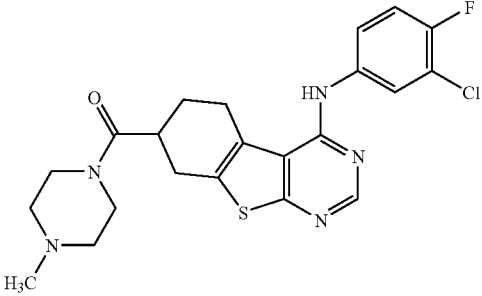 | 2.62 | 460 |
| 14 | 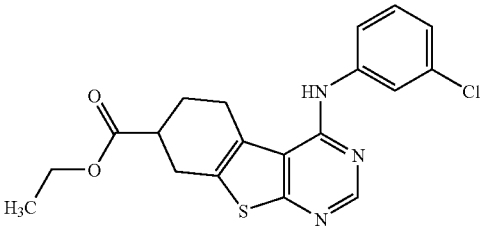 | 3.48 | 432 |
| 15 | 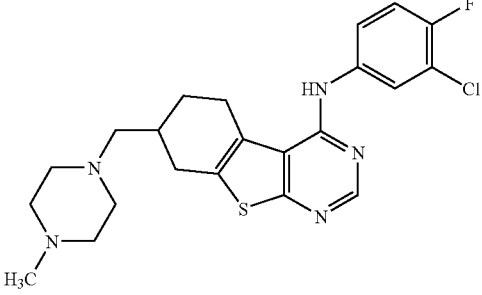 | 2.58 | 446 |
| 16 | 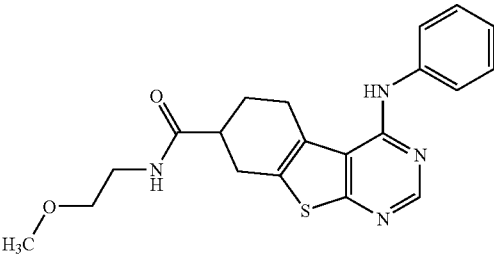 | 2.62 | 435 |

TABLE 1-continued

| Ex. No. | Structure | LCMS RT (min)a or TLC Rf [solvent] | LCMS Ion [M + H]+ |
|---|---|---|---|
| 17 | 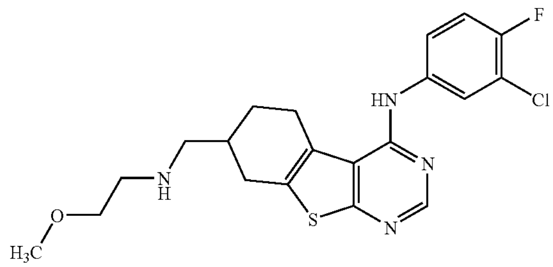 | 2.25 | 421 |
| 18 | 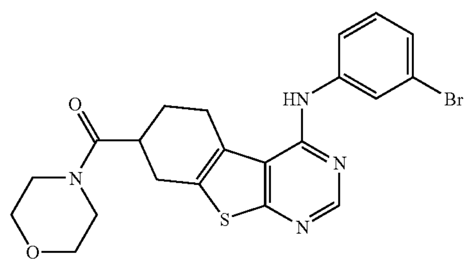 | 2.69 | 473 |
| 19 | 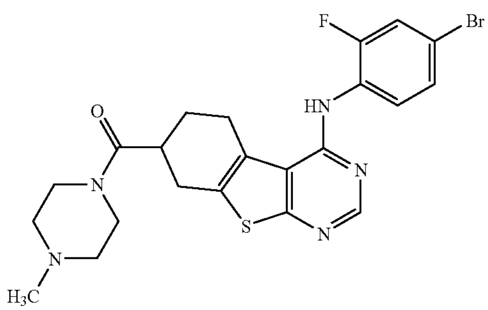 | 2.27 | 504 |
| 20 | 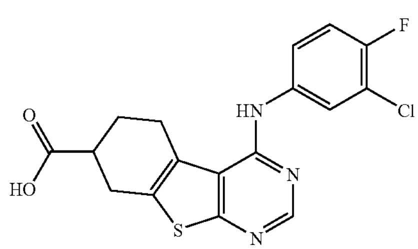 | 2.77 | 378 |
| 21 | 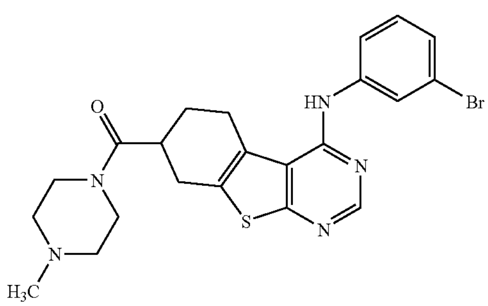 | 2.14 | 486 |

TABLE 1-continued
| Ex. No. | Structure | LCMS RT (min)[a] or TLC R_f [solvent] | LCMS Ion [M + H]+ |
|---|---|---|---|
| 22 | 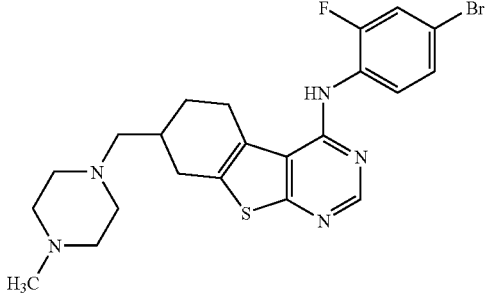 | 2.09 | 490 |
| 23 | 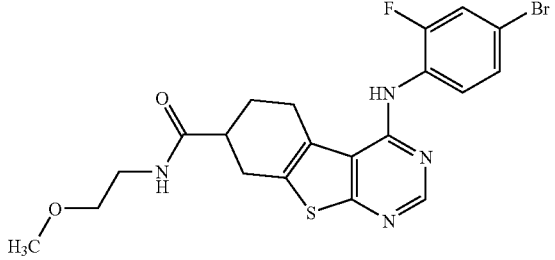 | 2.79 | 479 |
| 24 | 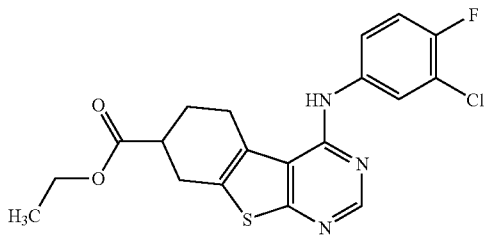 | 3.41 | 406 |
| 25 | 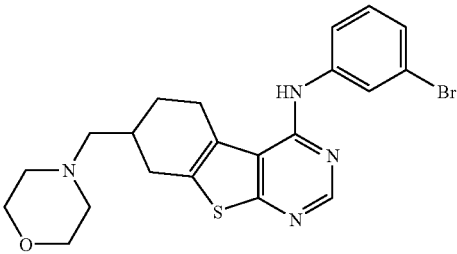 | 2.20 | 459 |
| 26 | 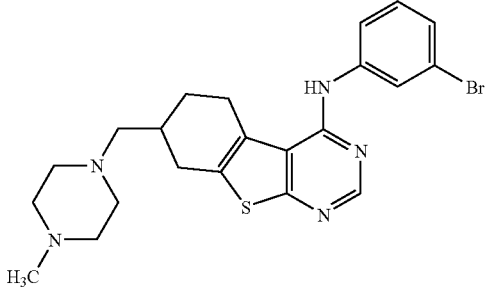 | 2.02 | 472 |

TABLE 1-continued

| Ex. No. | Structure | LCMS RT (min)[a] or TLC R_f [solvent] | LCMS Ion [M + H]+ |
|---|---|---|---|
| 27 | 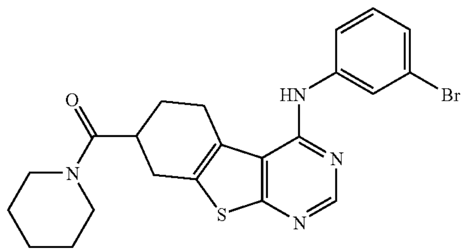 | 3.15 | 471 |
| 28 | 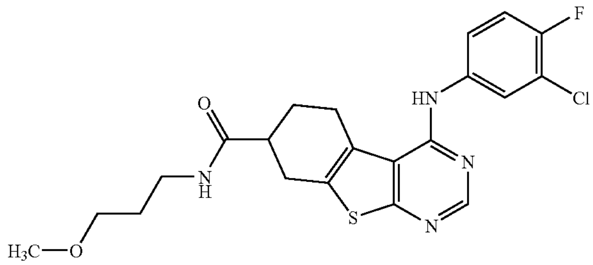 | 3.27 | 449 |
| 29 | 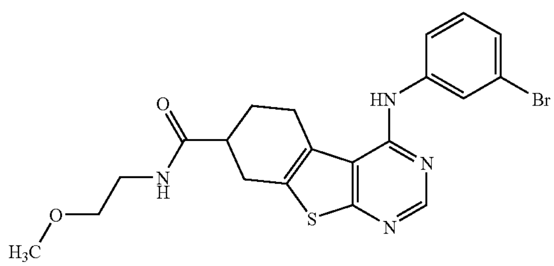 | 2.60 | 461 |
| 30 | 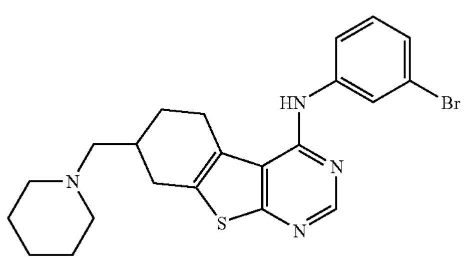 | 2.29 | 457 |
| 31 | 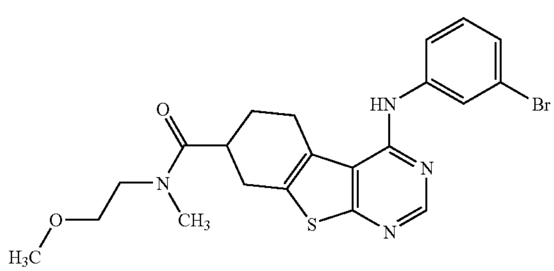 | 2.80 | 475 |

TABLE 1-continued

| Ex. No. | Structure | LCMS RT (min)ᵃ or TLC $R_f$ [solvent] | LCMS Ion [M + H]⁺ |
|---|---|---|---|
| 32 | 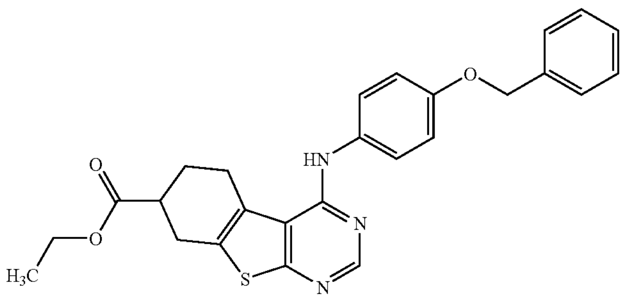 | 3.19 | 460 |
| 33 | 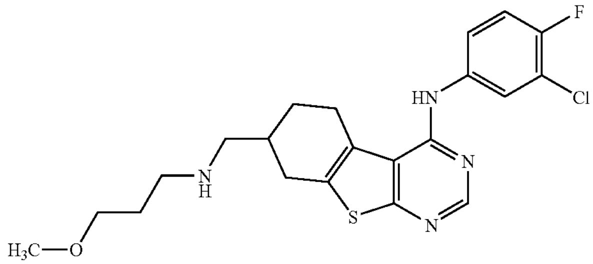 | 2.30 | 435 |
| 34 | 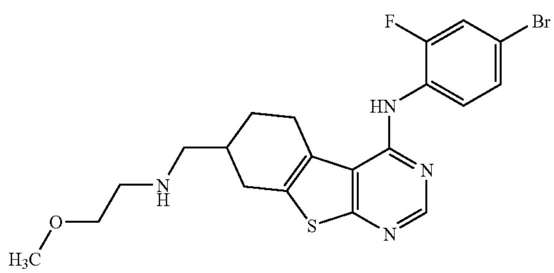 | 2.25 | 465 |
| 35 | 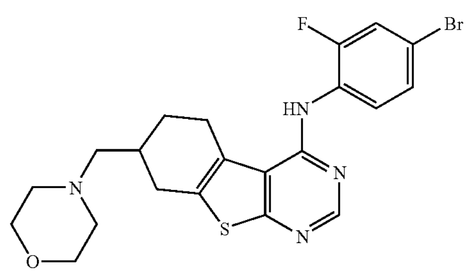 | 2.25 | 477 |
| 36 | 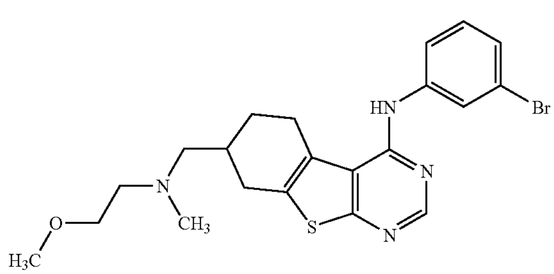 | 2.23 | 463 |

TABLE 1-continued

| Ex. No. | Structure | LCMS RT (min)[a] or TLC $R_f$ [solvent] | LCMS Ion [M + H]+ |
|---|---|---|---|
| 37 | 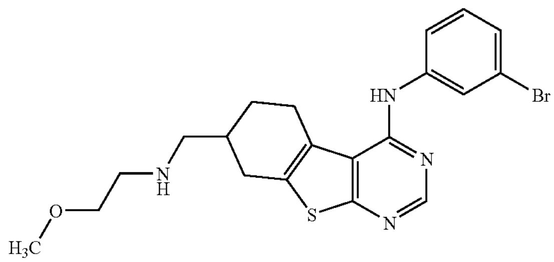 | 2.20 | 447 |
| 38 | 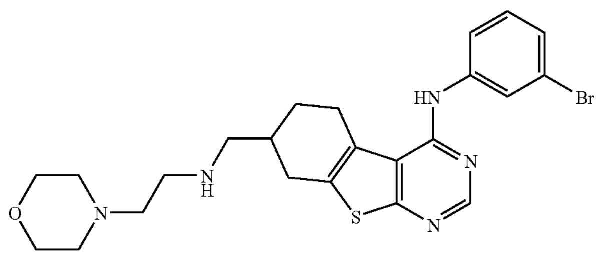 | 2.02 | 502 |
| 39 | 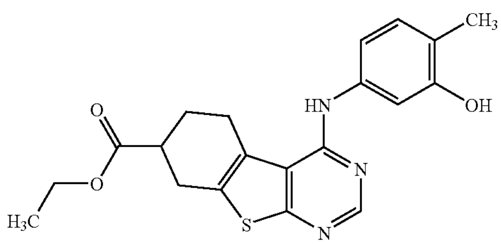 | 2.56 | 384 |
| 40 | 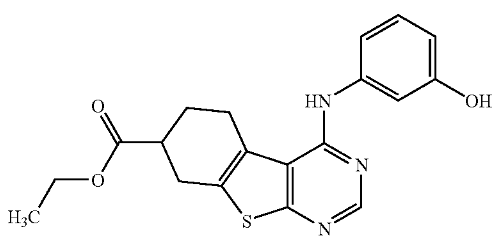 | 2.39 | 370 |
| 41 | 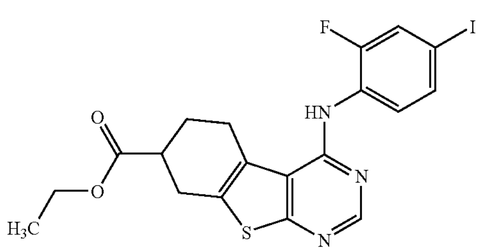 | 3.67 | 498 |

TABLE 1-continued

| Ex. No. | Structure | LCMS RT (min)[a] or TLC R_f [solvent] | LCMS Ion [M + H]+ |
|---|---|---|---|
| 42 | 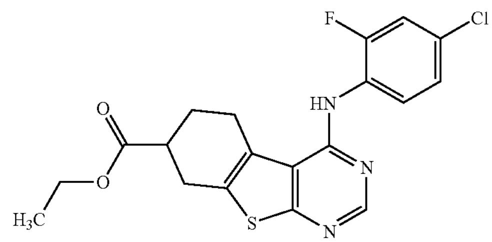 | 3.45 | 406 |
| 43 | 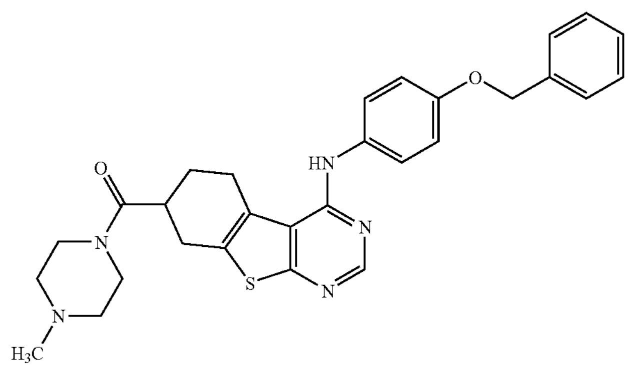 | 2.22 | 514 |
| 44 | 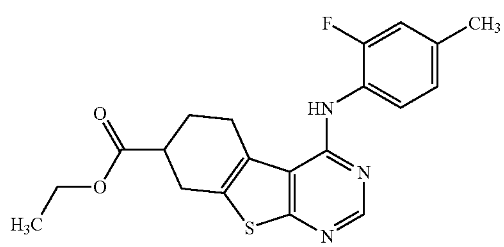 | 3.19 | 386 |
| 45 | 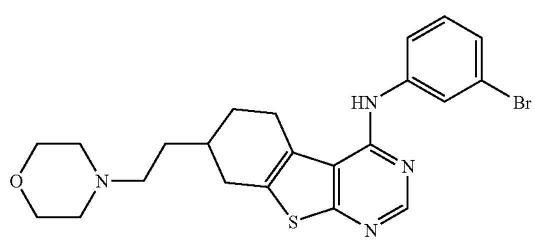 | 2.30 | 473 |
| 46 | 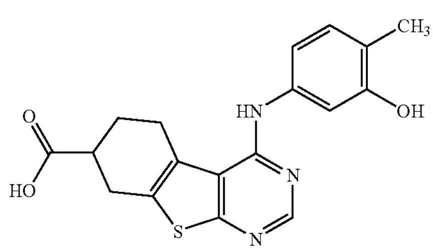 | 2.00 | 356 |

TABLE 1-continued

| Ex. No. | Structure | LCMS RT (min)[a] or TLC R$_f$ [solvent] | LCMS Ion [M + H]$^+$ |
|---|---|---|---|
| 47 | 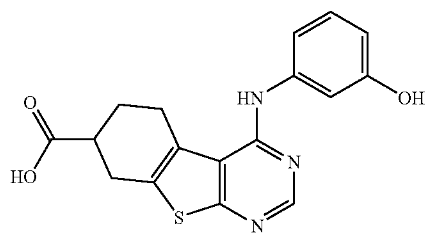 | 1.83 | 342 |
| 48 | 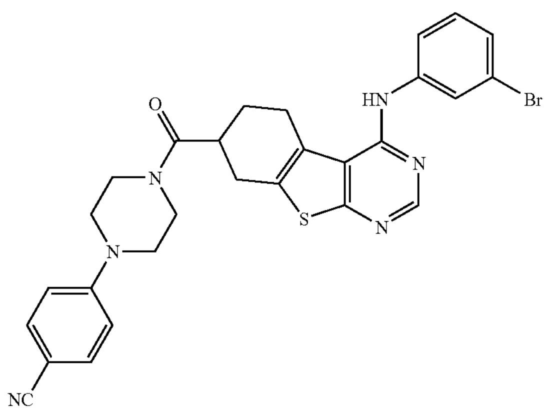 | 3.16 | 573 |
| 49 | 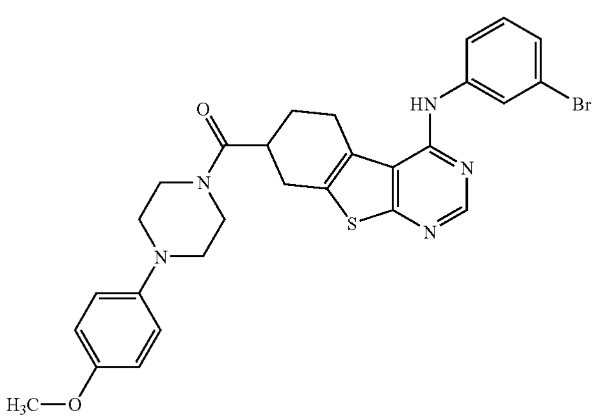 | 2.62 | 578 |
| 50 | 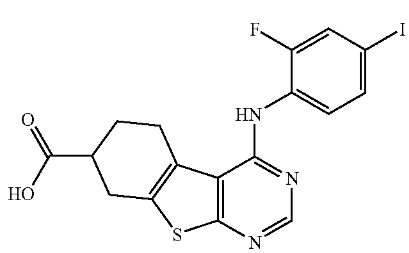 | 3.09 | 470 |

TABLE 1-continued

| Ex. No. | Structure | LCMS RT (min)ᵃ or TLC R_f [solvent] | LCMS Ion [M + H]⁺ |
|---|---|---|---|
| 51 | 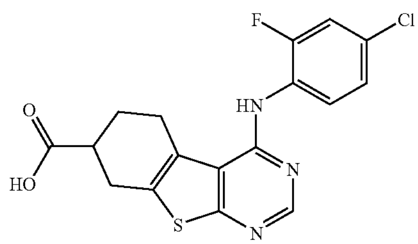 | 2.81 | 378 |
| 52 | 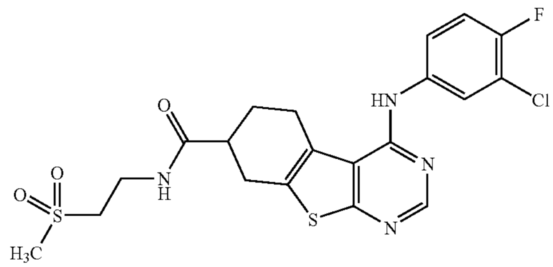 | 2.44 | 483 |
| 53 | 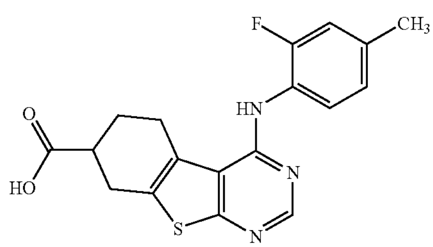 | 2.49 | 358 |
| 54 | 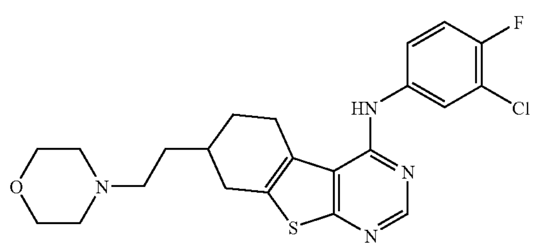 | 2.22 | 447 |
| 55 | 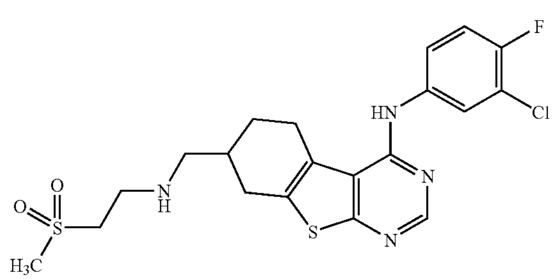 | 2.17 | 470 |

TABLE 1-continued

| Ex. No. | Structure | LCMS RT (min)[a] or TLC R_f [solvent] | LCMS Ion [M + H]+ |
|---|---|---|---|
| 56 | 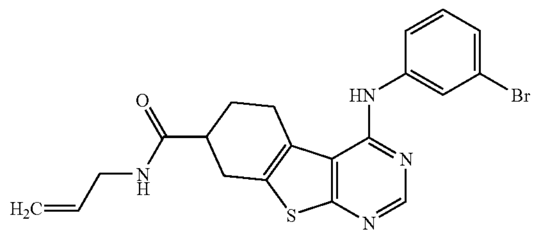 | 2.78 | 444 |
| 57 | 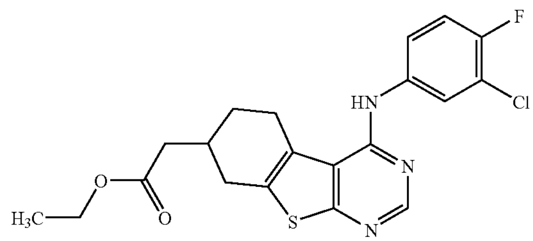 | 3.49 | 420 |
| 58 | 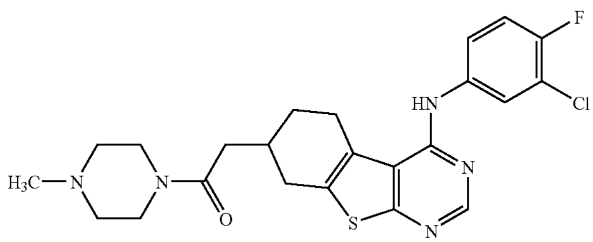 | 2.20 | 474 |
| 59 | 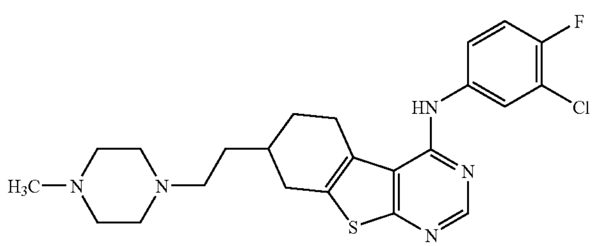 | 2.07 | 460 |
| 60 | 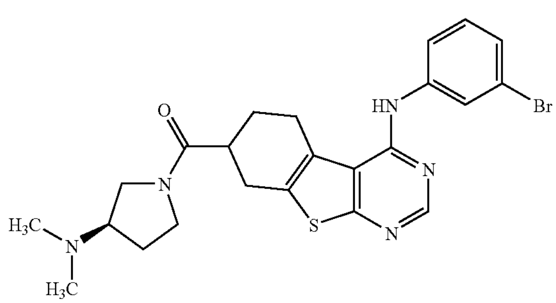 | 2.15 | 501 |

TABLE 1-continued

| Ex. No. | Structure | LCMS RT (min)[a] or TLC R$_f$ [solvent] | LCMS Ion [M + H]$^+$ |
|---|---|---|---|
| 61 | 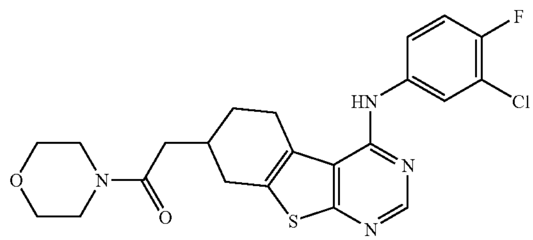 | 2.78 | 461 |
| 62 | 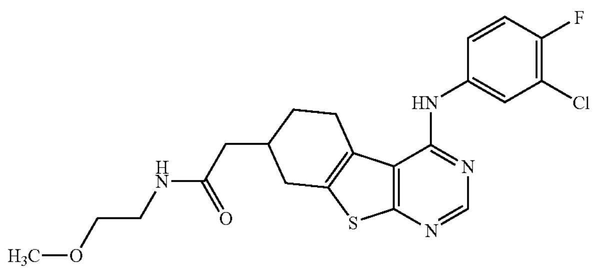 | 2.58 | 449 |
| 63 | 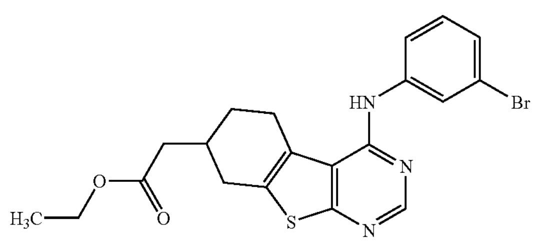 | 3.39 | 446 |
| 64 | 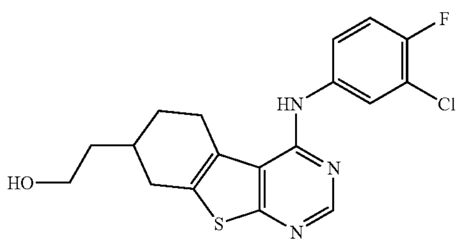 | 2.83 | 378 |
| 65 | 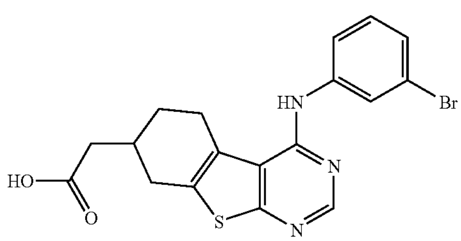 | 2.91 | 420 |

TABLE 1-continued
| Ex. No. | Structure | LCMS RT (min)[a] or TLC R$_f$ [solvent] | LCMS Ion [M + H]+ |
|---|---|---|---|
| 66 | 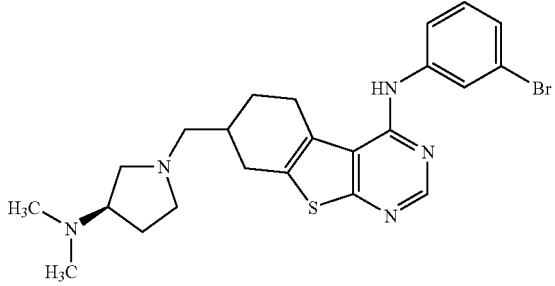 | 2.02 | 487 |
| 67 | 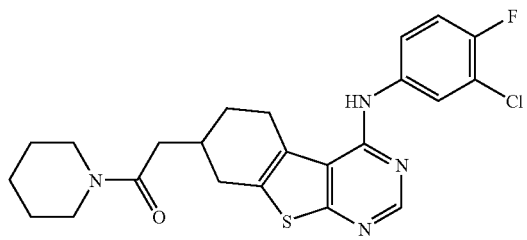 | 3.08 | 459 |
| 68 | 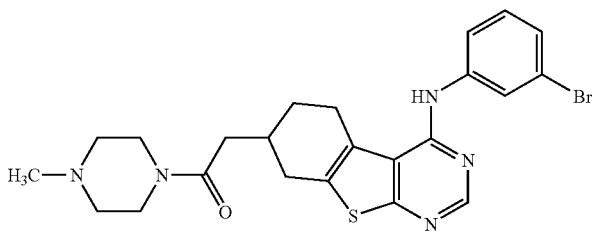 | 2.21 | 502 |
| 69 | 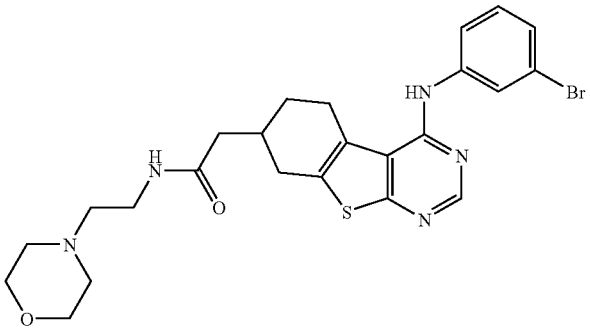 | 2.20 | 530 |
| 70 | 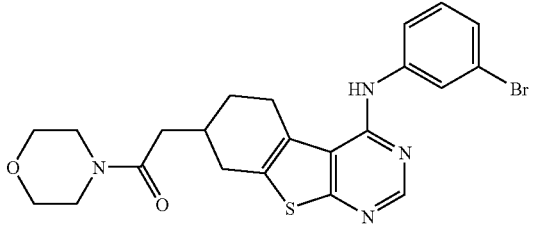 | 2.73 | 487 |

TABLE 1-continued
| Ex. No. | Structure | LCMS RT (min)ᵃ or TLC R_f [solvent] | LCMS Ion [M + H]⁺ |
|---|---|---|---|
| 71 | 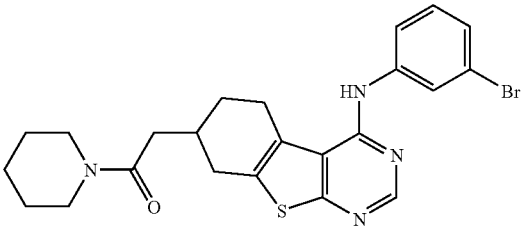 | 3.13 | 485 |
| 72 | 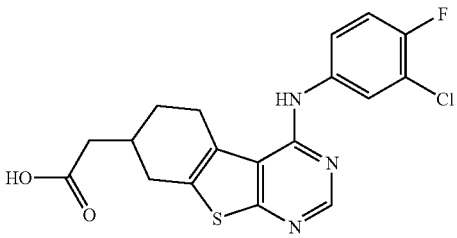 | 2.76 | 392 |
| 73 | 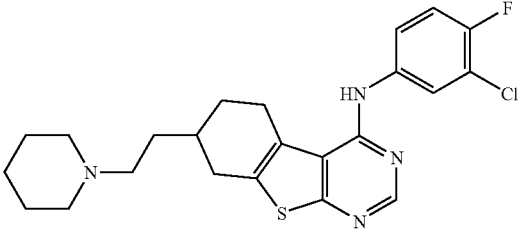 | 2.34 | 445 |
| 74 | 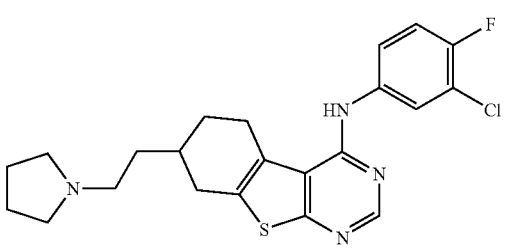 | 2.30 | 431 |
| 75 | 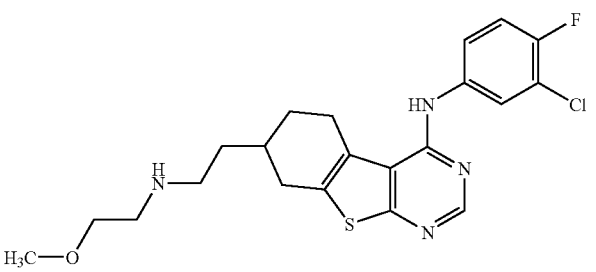 | 2.28 | 435 |

TABLE 1-continued
| Ex. No. | Structure | LCMS RT (min)[a] or TLC R_f [solvent] | LCMS Ion [M + H]+ |
|---|---|---|---|
| 76 | 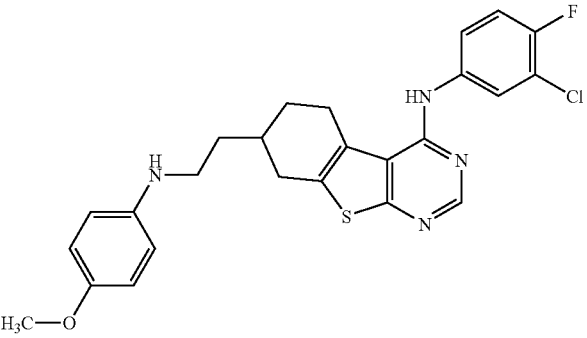 | 2.53 | 483 |
| 77 | 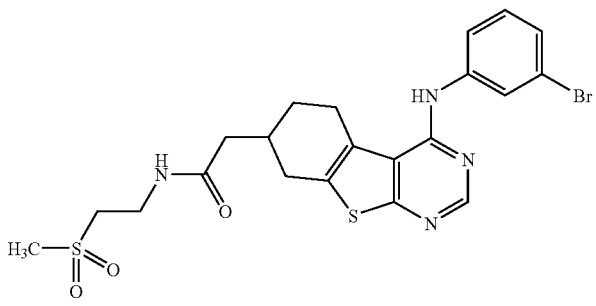 | 2.61 | 523 |
| 78 | 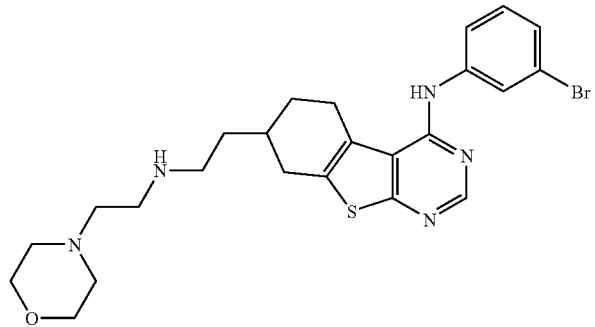 | 2.12 | 516 |
| 79 | 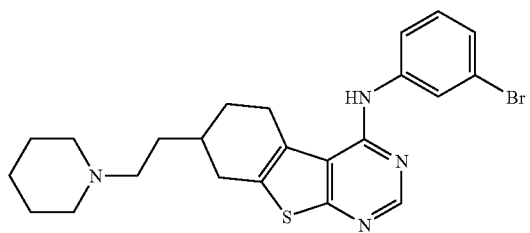 | 2.38 | 471 |
| 80 | 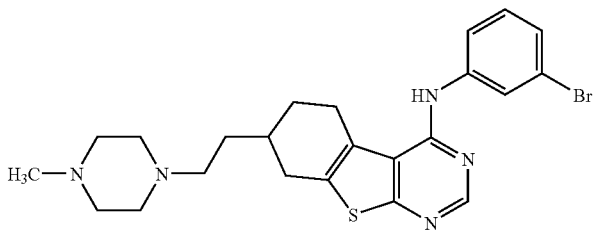 | 2.06 | 486 |

TABLE 1-continued

| Ex. No. | Structure | LCMS RT (min)[a] or TLC R_f [solvent] | LCMS Ion [M + H]+ |
|---|---|---|---|
| 81 | 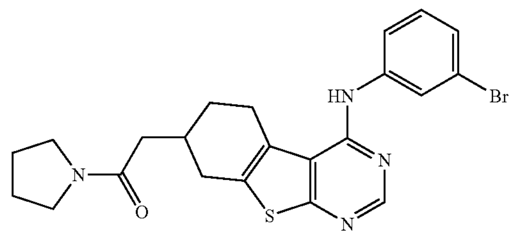 | 3.04 | 471 |
| 82 | 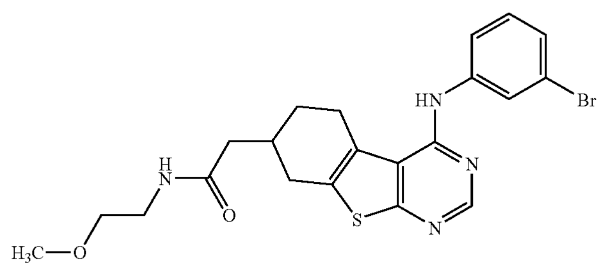 | 2.63 | 475 |
| 83 | 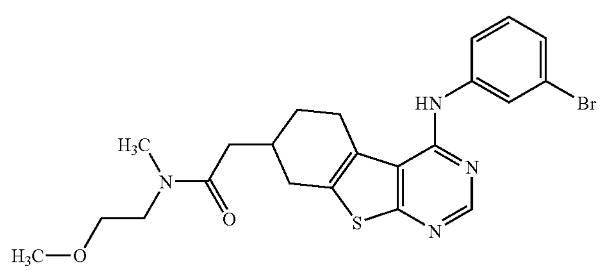 | 2.84 | 491 |
| 84 | 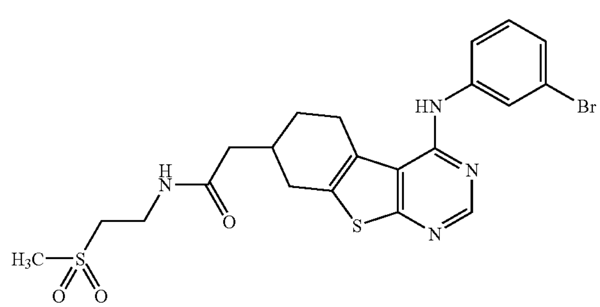 | 2.26 | 509 |
| 85 | 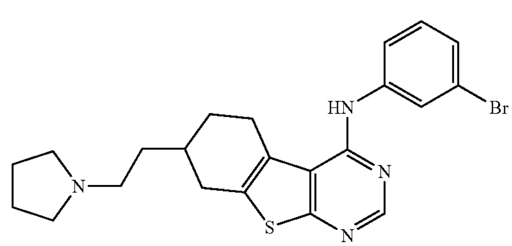 | 2.33 | 457 |

TABLE 1-continued

| Ex. No. | Structure | LCMS RT (min)[a] or TLC R$_f$ [solvent] | LCMS Ion [M + H]$^+$ |
|---|---|---|---|
| 86 | 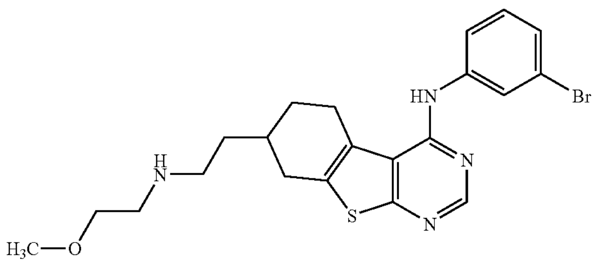 | 2.30 | 461 |
| 87 | 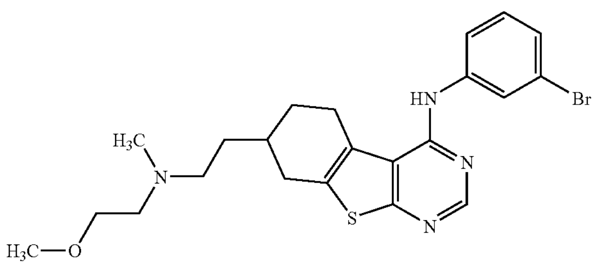 | 2.31 | 475 |
| 88 | 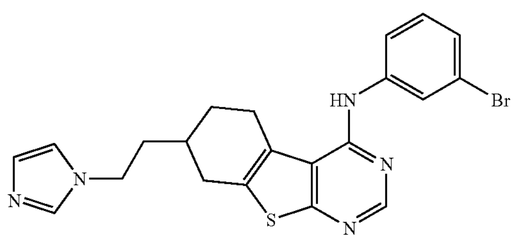 | 2.33 | 454 |
| 89 | 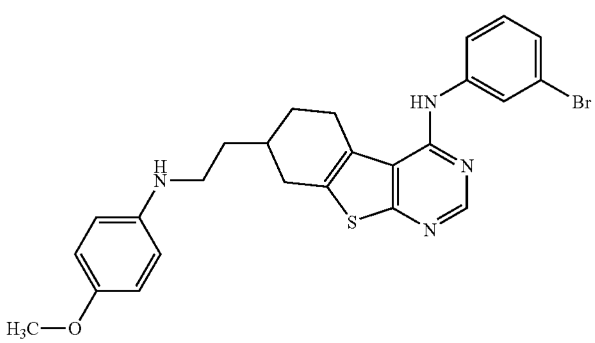 | 2.54 | 509 |
| 90 | 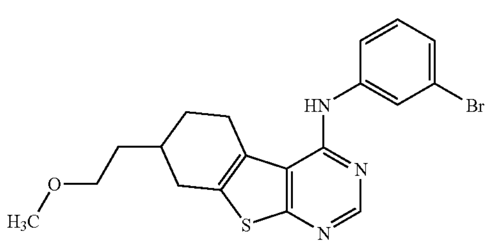 | 3.33 | 418 |

TABLE 1-continued

| Ex. No. | Structure | LCMS RT (min)[a] or TLC R_f [solvent] | LCMS Ion [M + H]+ |
|---|---|---|---|
| 91 | 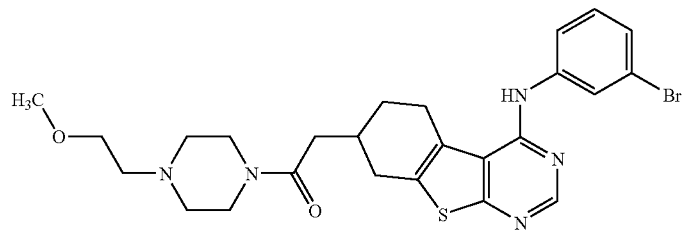 | 2.31 | 544 |
| 92 | 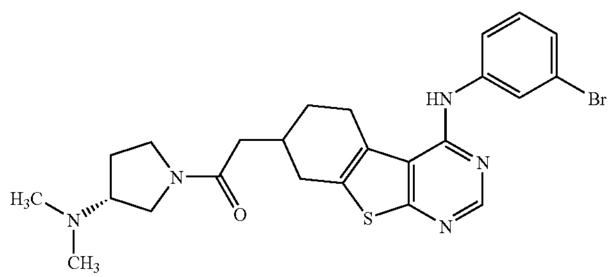 | 2.21 | 516 |
| 93 | 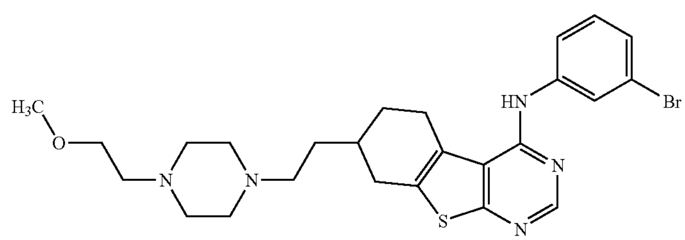 | 2.11 | 530 |
| 94 | 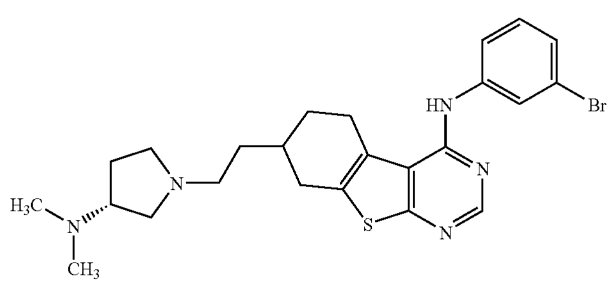 | 2.09 | 502 |
| 95 | 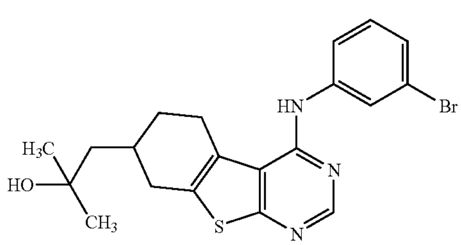 | 2.11 | 432 |

TABLE 1-continued
| Ex. No. | Structure | LCMS RT (min)[a] or TLC R_f [solvent] | LCMS Ion [M + H]+ |
|---|---|---|---|
| 96 | 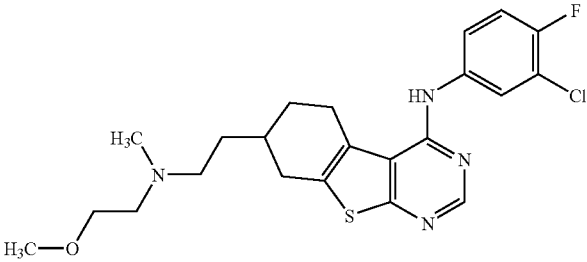 | 2.30 | 449 |
| 97 | 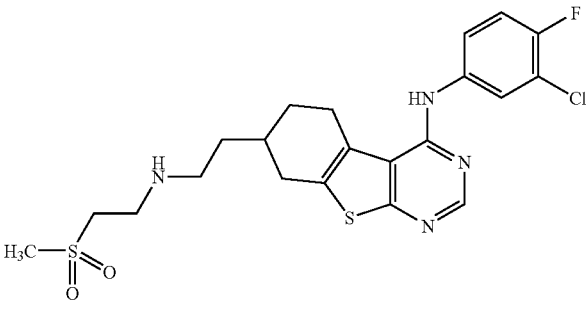 | 2.26 | 483 |
| 98 | 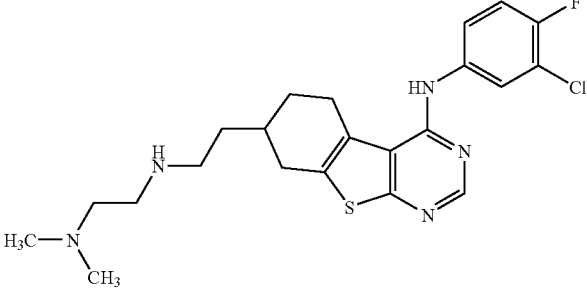 | 2.07 | 448 |
| 99 | 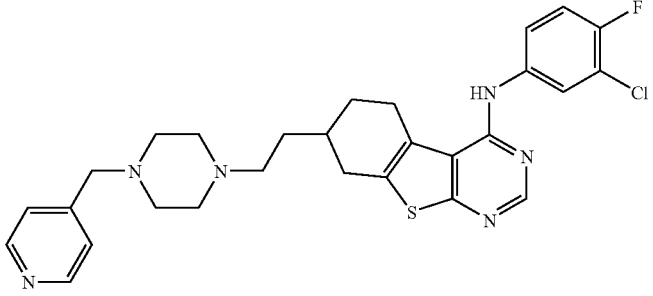 | 2.13 | 577 |
| 100 | 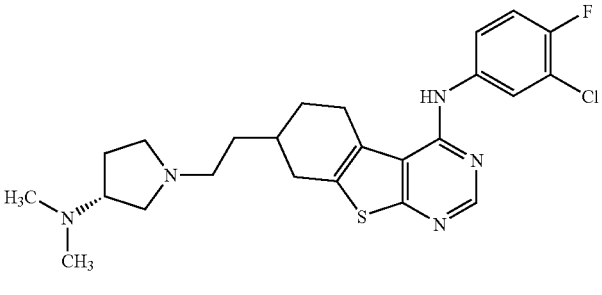 | 2.09 | 474 |

TABLE 1-continued

| Ex. No. | Structure | LCMS RT (min)[a] or TLC R_f [solvent] | LCMS Ion [M + H]+ |
|---|---|---|---|
| 101 | 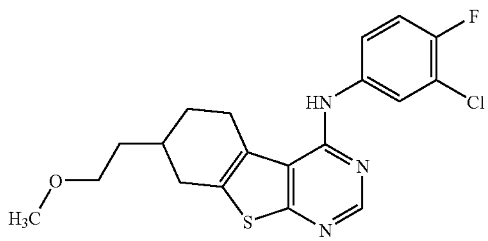 | 3.27 | 392 |
| 102 | 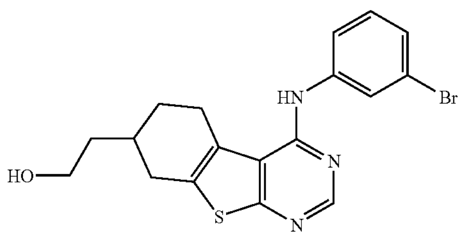 | 2.91 | 404 |
| 103 | 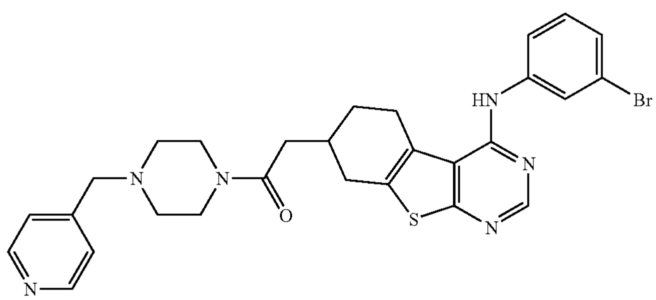 | 2.17 | 577 |
| 104 | 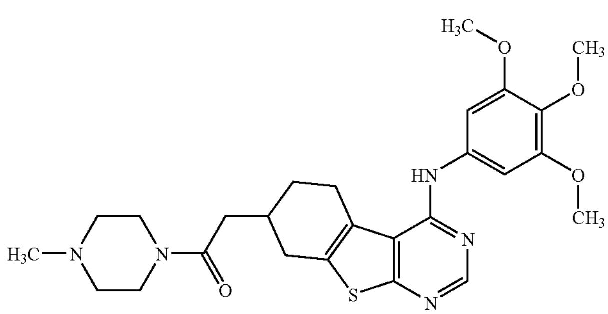 | 1.72 | 512 |
| 105 | 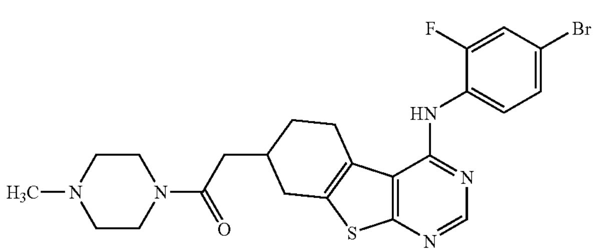 | 2.33 | 518 |

TABLE 1-continued

| Ex. No. | Structure | LCMS RT (min)[a] or TLC R$_f$ [solvent] | LCMS Ion [M + H]$^+$ |
| --- | --- | --- | --- |
| 106 | 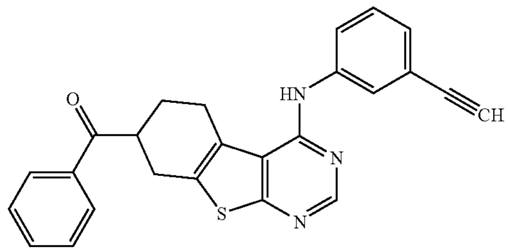 | | |
| 107 | 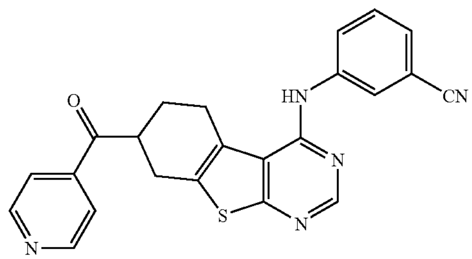 | | |
| 108 | 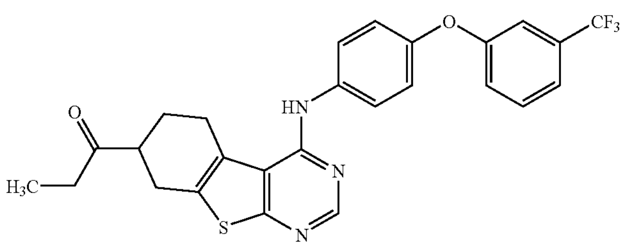 | | |
| 109 | 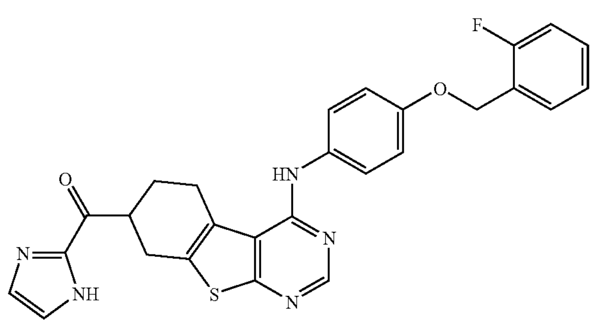 | | |
| 110 | 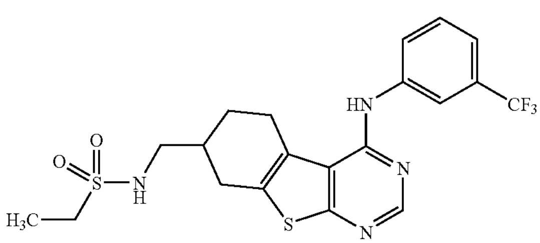 | | |

TABLE 1-continued

| Ex. No. | Structure | LCMS RT (min)[a] or TLC R_f [solvent] | LCMS Ion [M + H]+ |
|---|---|---|---|
| 111 | 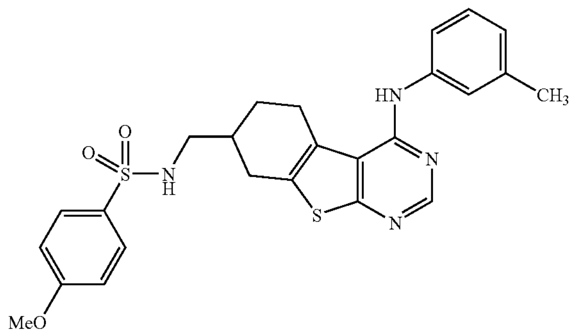 | | |
| 112 | 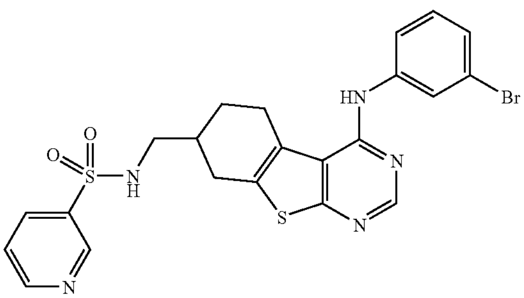 | | |
| 113 | 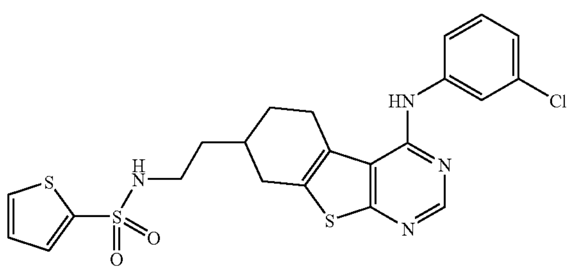 | | |
| 114 | 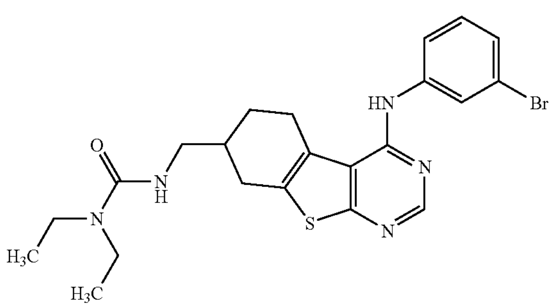 | | |
| 115 | 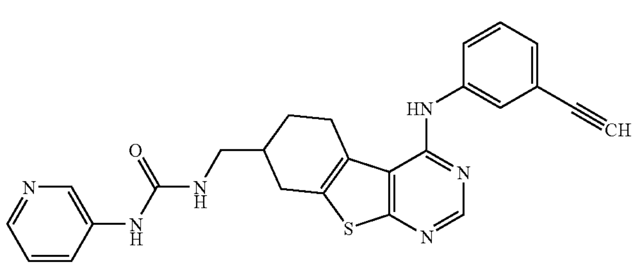 | | |

TABLE 1-continued
| Ex. No. | Structure | LCMS RT (min)[a] or TLC R$_f$ [solvent] | LCMS Ion [M + H]$^+$ |
|---|---|---|---|
| 116 | 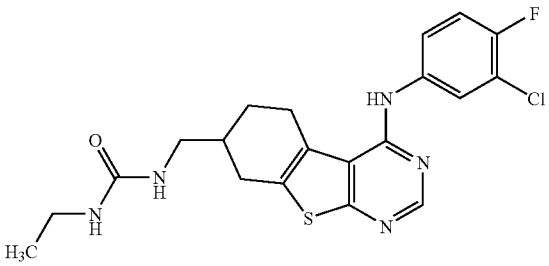 | | |
| 117 | 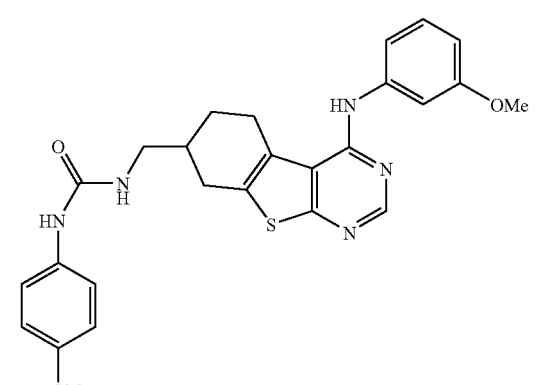 | | |
| 118 | 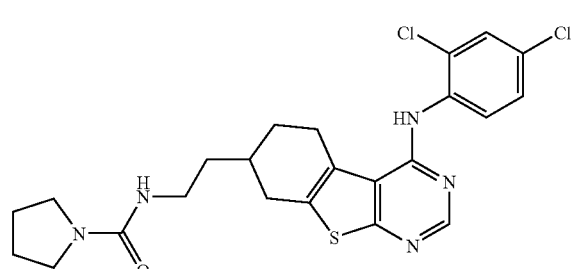 | | |
| 119 | 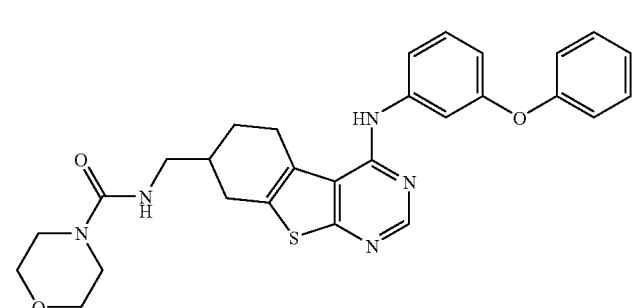 | | |

TABLE 1-continued
| Ex. No. | Structure | LCMS RT (min)[a] or TLC R_f [solvent] | LCMS Ion [M + H]+ |
|---|---|---|---|
| 120 | 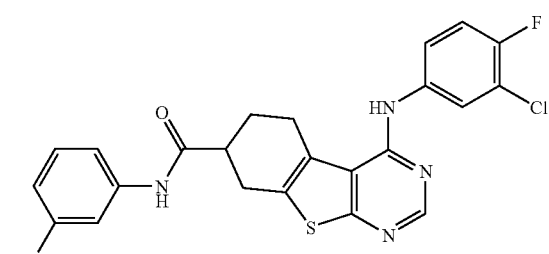 | | |
| 121 | 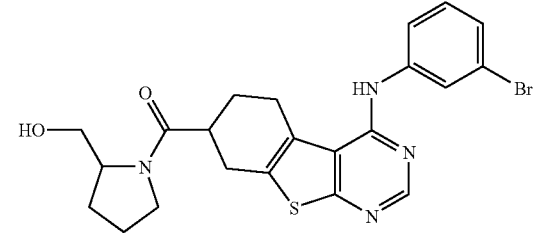 | | |
| 122 | 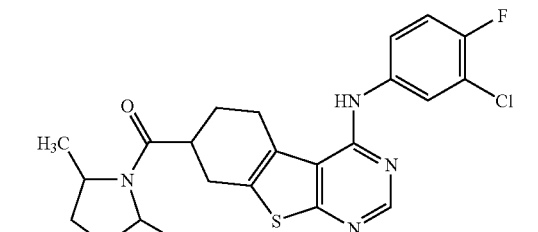 | | |
| 123 | 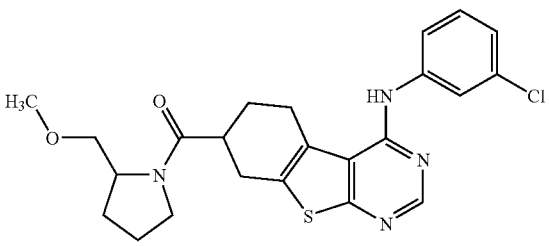 | | |
| 124 | 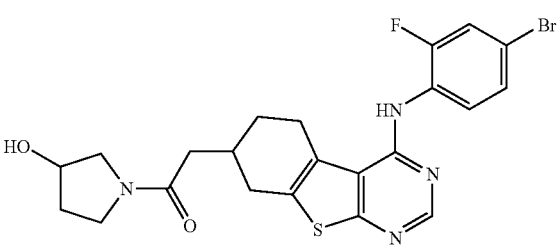 | | |

TABLE 1-continued

| Ex. No. | Structure | LCMS RT (min)ᵃ or TLC R_f [solvent] | LCMS Ion [M + H]⁺ |
|---|---|---|---|
| 125 | 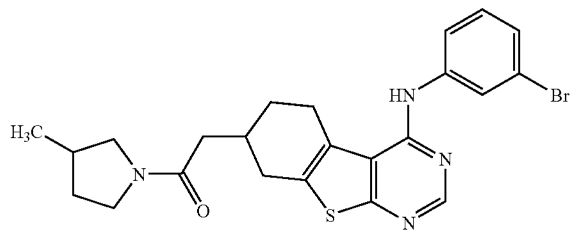 | | |
| 126 | 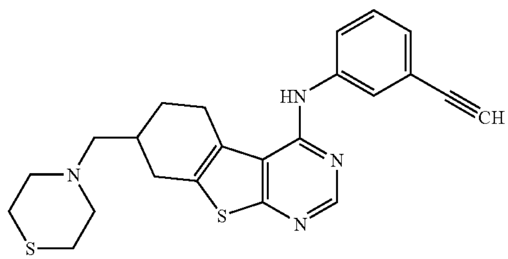 | | |
| 127 | 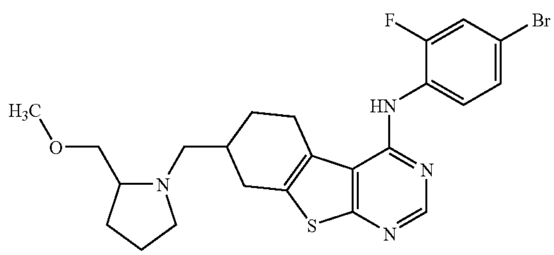 | | |
| 128 | 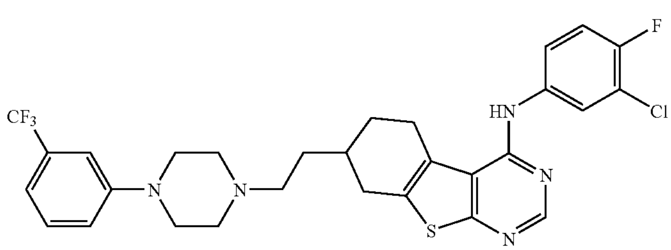 | | |
| 129 | 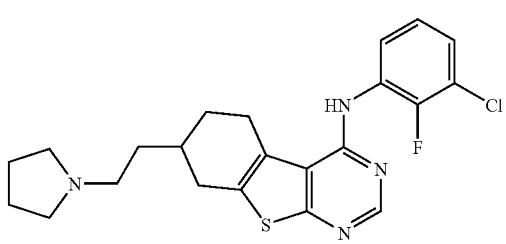 | | |

TABLE 1-continued

| Ex. No. | Structure | LCMS RT (min)[a] or TLC R_f [solvent] | LCMS Ion [M + H]+ |
|---|---|---|---|
| 130 | 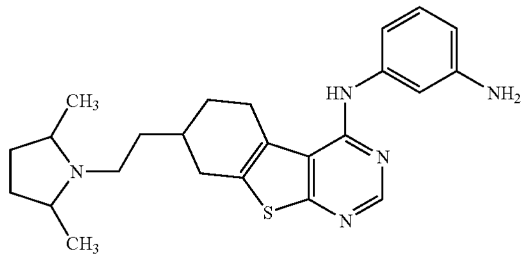 | | |
| 131 | 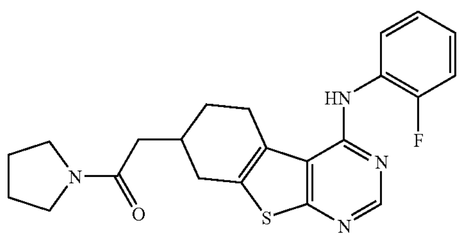 | | |
| 132 | 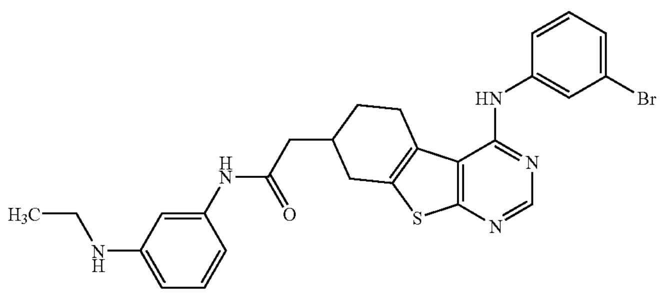 | | |
| 133 | 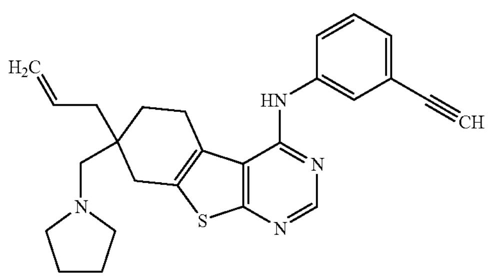 | | |
| 134 | 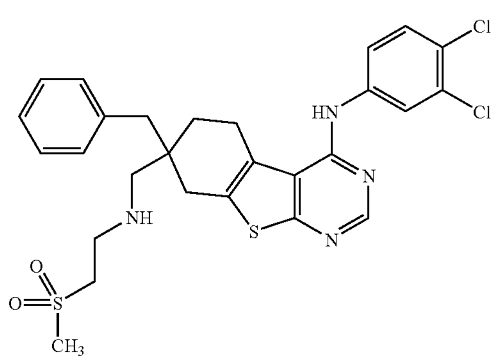 | | |

TABLE 1-continued

| Ex. No. | Structure | LCMS RT (min)[a] or TLC R$_f$ [solvent] | LCMS Ion [M + H]$^+$ |
|---|---|---|---|
| 135 | 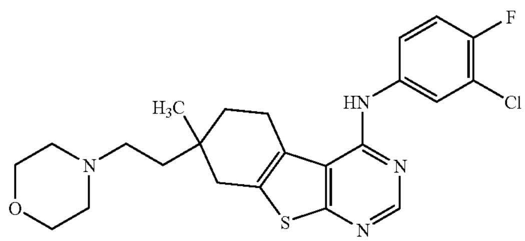 | | |
| 136 | 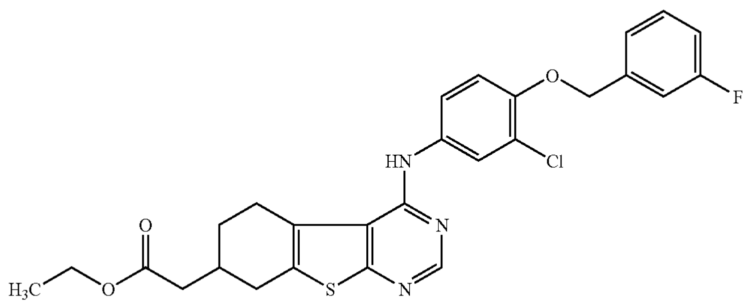 | R$_f$ = 0.3 [30% EtOAc/Hex] | 526.2 |
| 137 | 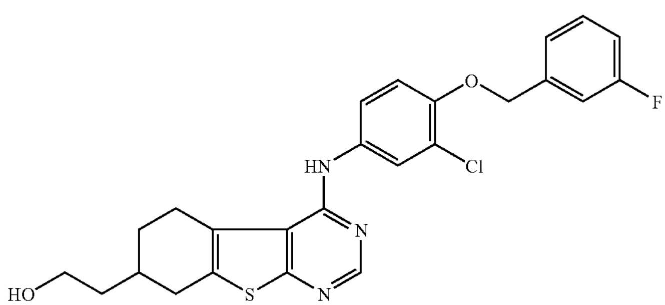 | 3.36 | 484 |
| 138 | 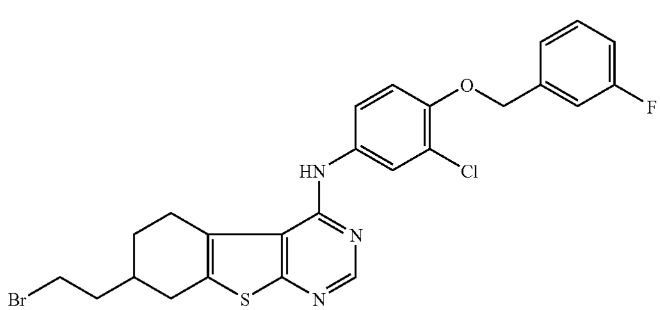 | R$_f$ = 0.9 [50% EtOAc/Hex] | 546.3 |

TABLE 1-continued

| Ex. No. | Structure | LCMS RT (min)[a] or TLC R$_f$ [solvent] | LCMS Ion [M + H]+ |
|---|---|---|---|
| 139 | 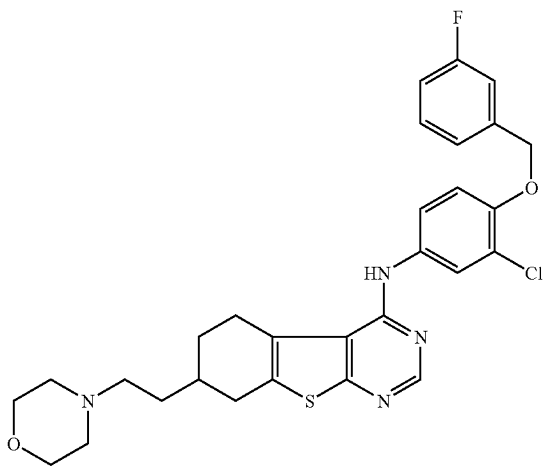 | 2.64 | 553 |
| 140 | 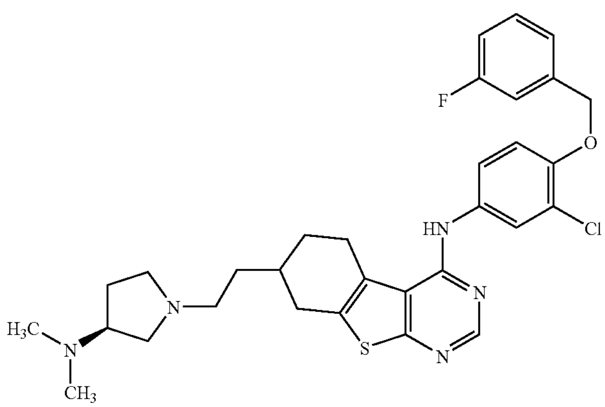 | 2.13 | 580/582 |
| 141 | 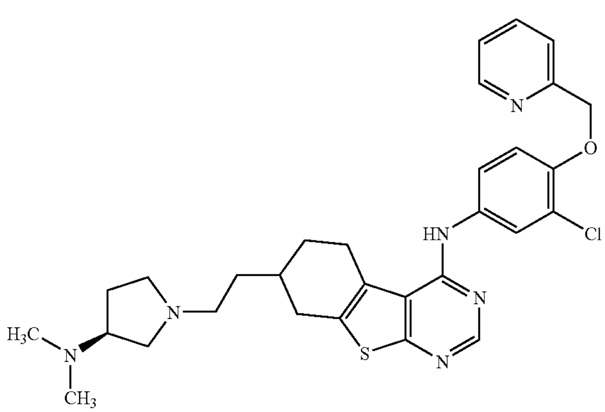 | 2.07 | 563/565 |

TABLE 1-continued

| Ex. No. | Structure | LCMS RT (min)[a] or TLC $R_f$ [solvent] | LCMS Ion [M + H]+ |
|---|---|---|---|
| 142 | 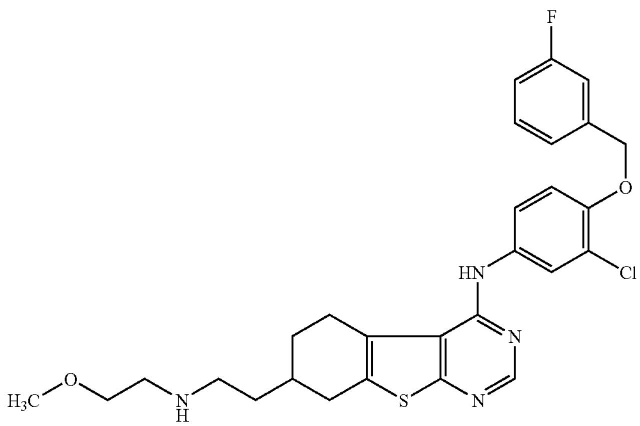 | $R_f$ = 0.1 [5% MeOH/ DCM] | 541.2 |
| 143 | 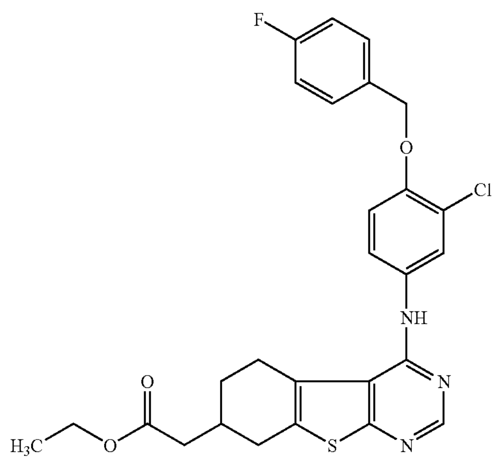 | $R_f$ = 0.2 [30% EtOAc/ Hex] | 526/528 |
| 144 | 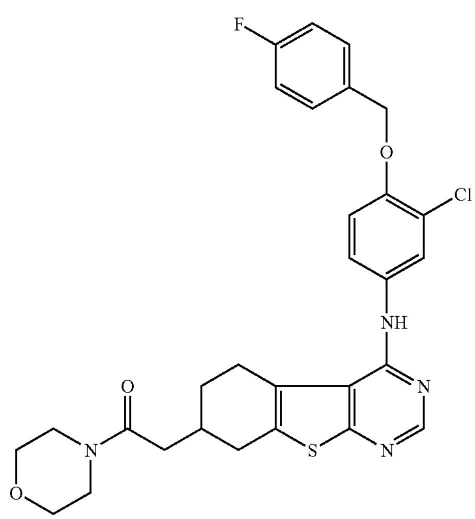 | $R_f$ = 0.2 [80% EtOAc/ Hex] | 567/569 |

TABLE 1-continued
| Ex. No. | Structure | LCMS RT (min)[a] or TLC R$_f$ [solvent] | LCMS Ion [M + H]+ |
|---|---|---|---|
| 145 | 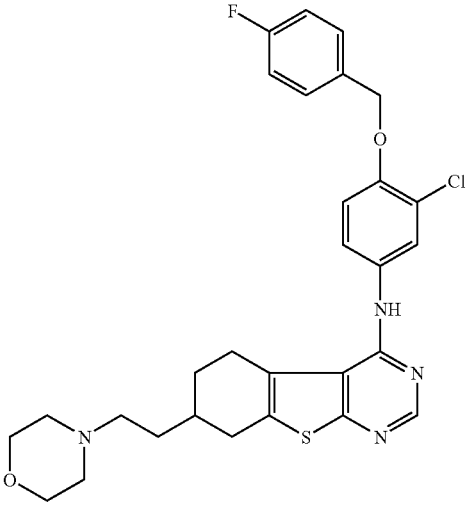 | R$_f$ = 0.27 [5:95 MeOH/DCM] | 553/555 |
| 146 | 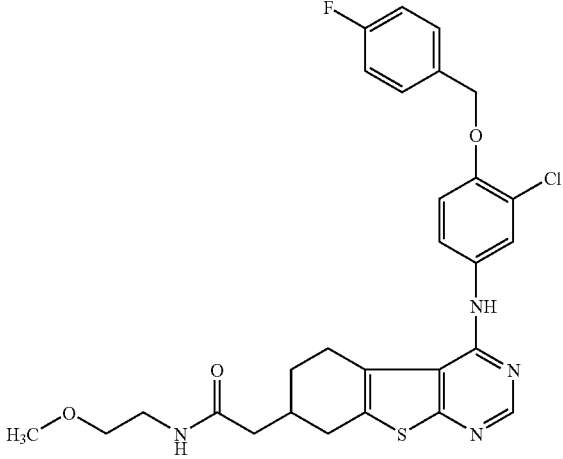 | R$_f$ = 0.2 [5:95 MeOH:DCM] | 555/557 |
| 147 | 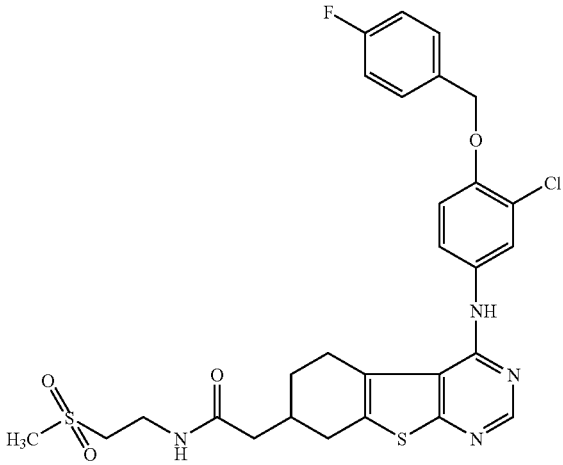 | 3.20 | 603/605 |

TABLE 1-continued
| Ex. No. | Structure | LCMS RT (min)[a] or TLC R$_f$ [solvent] | LCMS Ion [M + H]+ |
|---|---|---|---|
| 148 | 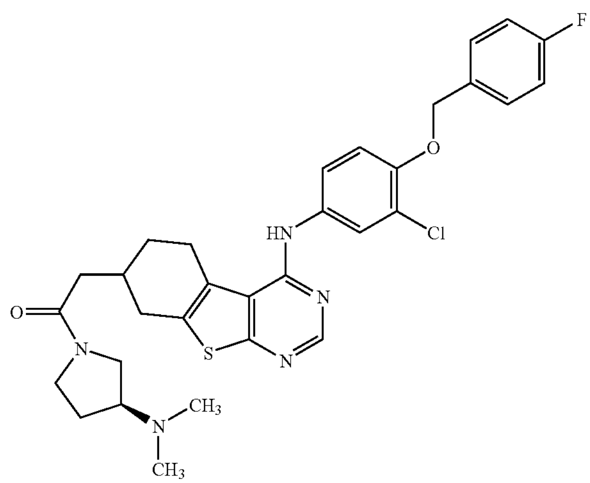 | 2.73 | 594/596 |
| 149 | 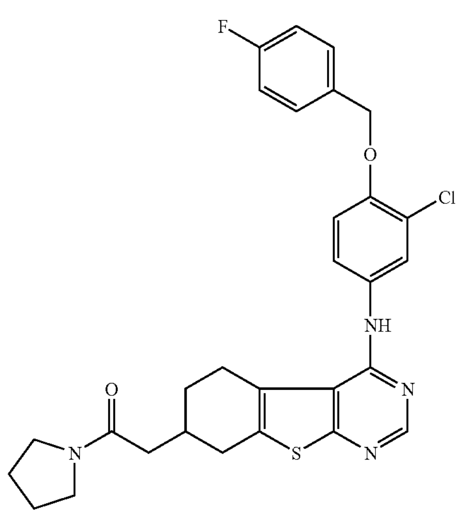 | R$_f$ = 0.23 [5:95 MeOH/ DCM] | 551/553 |
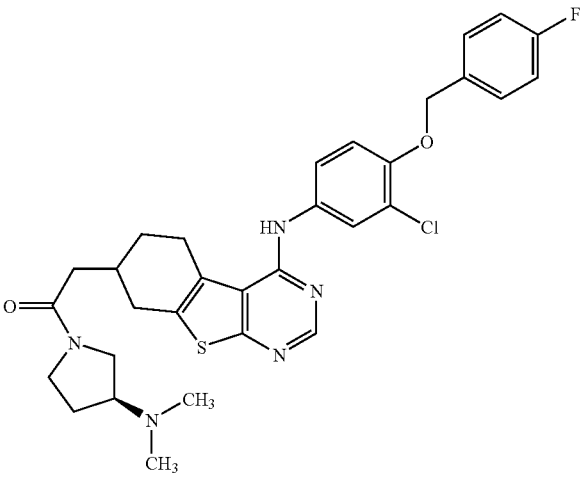

TABLE 1-continued

| Ex. No. | Structure | LCMS RT (min)[a] or TLC R$_f$ [solvent] | LCMS Ion [M + H]$^+$ |
|---|---|---|---|
| 150 | 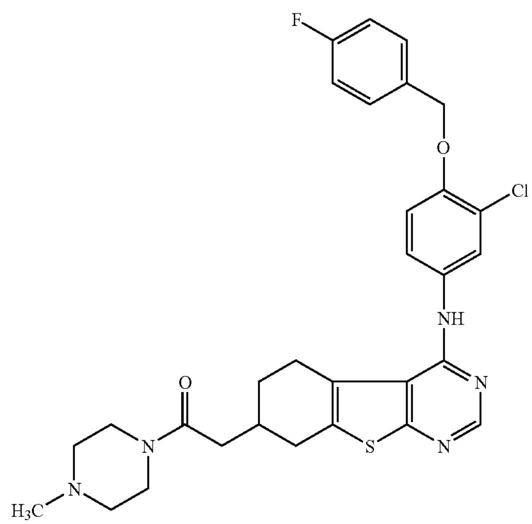 | R$_f$ = 0.1 [5:95 MeOH/ DCM] | 580/582 |
| 151 | 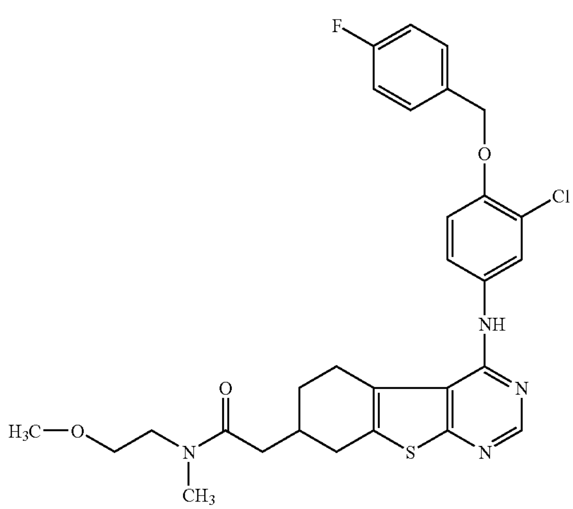 | R$_f$ = 0.16 [80:20 EtOAc: Hex] | 569/571 |

TABLE 1-continued
| Ex. No. | Structure | LCMS RT (min)[a] or TLC R$_f$ [solvent] | LCMS Ion [M + H]$^+$ |
| --- | --- | --- | --- |
| 152 | 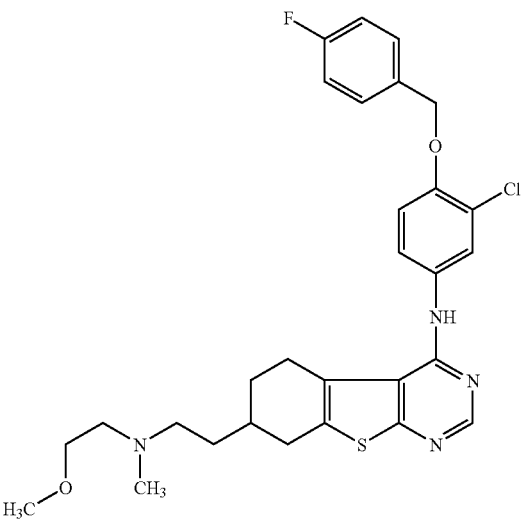 | R$_f$ = 0.3 [10:90 MeOH: DCM] | 555/557 |
| 153 | 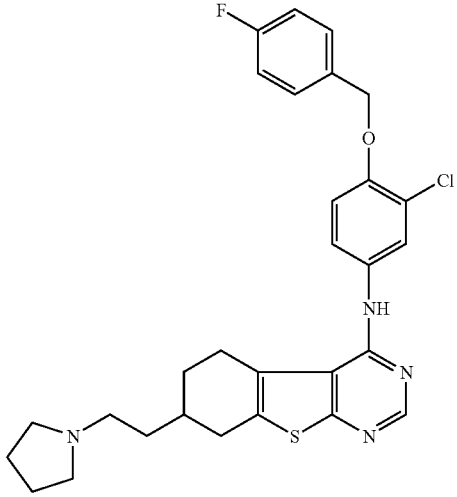 | R$_f$ = 0.25 [10:90 MeOH: DCM] | 537/539 |

TABLE 1-continued
| Ex. No. | Structure | LCMS RT (min)[a] or TLC $R_f$ [solvent] | LCMS Ion [M + H]+ |
|---|---|---|---|
| 154 | 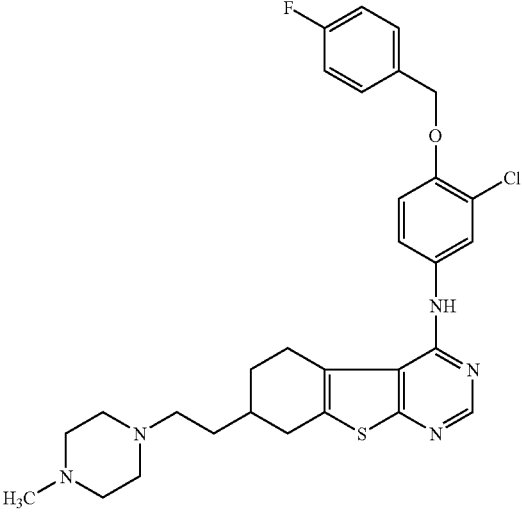 | $R_f$ = 0.2 [5:95 MeOH/ DCM] | 566/568 |
| 155 | 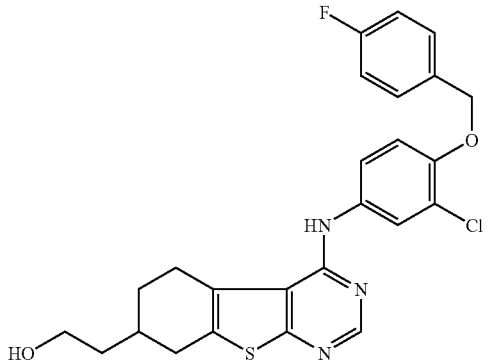 | $R_f$ = 0.1 [50:50 EtOAc: Hex] | 484/486 |
| 156 | 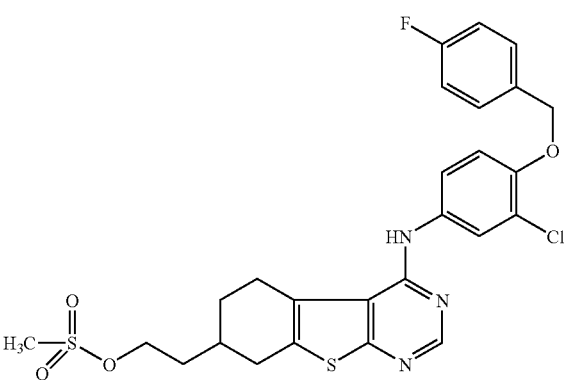 | $R_f$ = 0.1 [50:50 EtOAc: Hex] | 562/564 |

TABLE 1-continued
| Ex. No. | Structure | LCMS RT (min)ᵃ or TLC R_f [solvent] | LCMS Ion [M + H]⁺ |
|---|---|---|---|
| 157 | 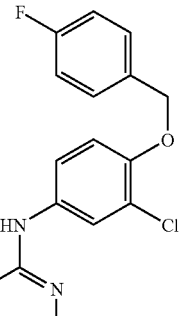 | 1.93 | 580 |
| 158 | 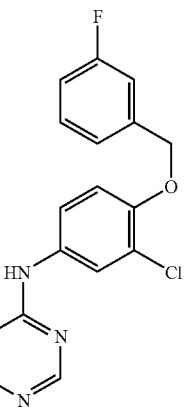 | 2.25 | 566 |
| 159 | 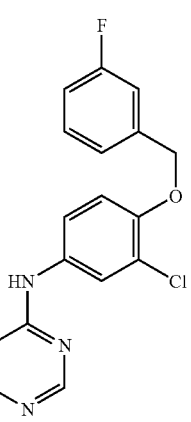 | 2.17 | 555 |

TABLE 1-continued
| Ex. No. | Structure | LCMS RT (min)[a] or TLC R_f [solvent] | LCMS Ion [M + H]+ |
|---|---|---|---|
| 160 | 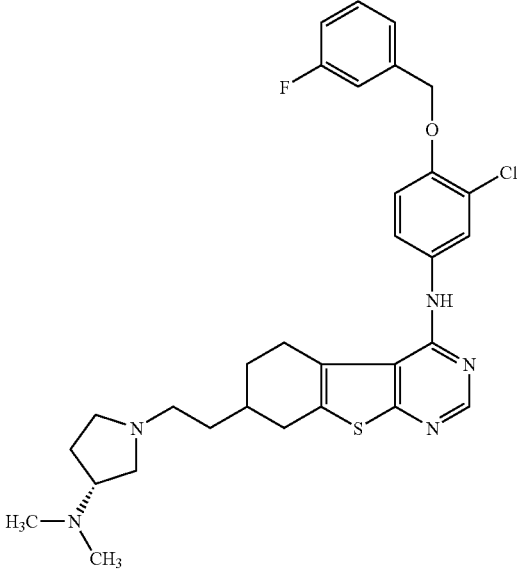 | 1.87 | 580 |
| 161 | 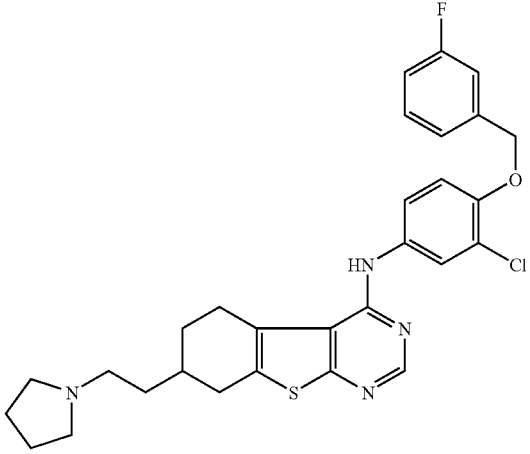 | 2.58 | 537 |
| 162 | 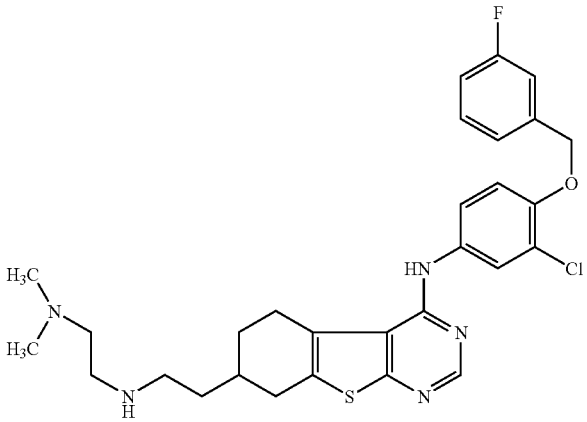 | 2.31 | 554 |

TABLE 1-continued

| Ex. No. | Structure | LCMS RT (min)[a] or TLC R_f [solvent] | LCMS Ion [M + H]+ |
|---|---|---|---|
| 163 | 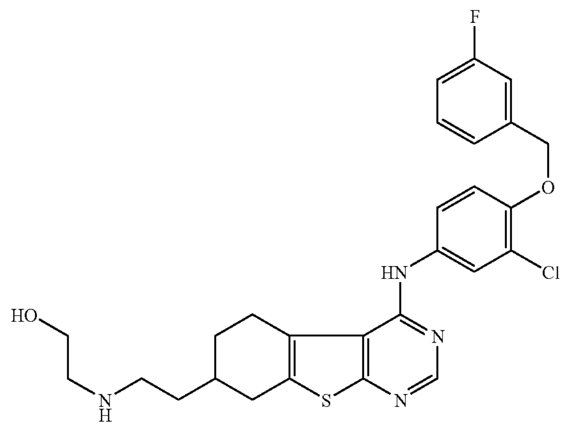 | 2.51 | 527 |
| 164 | 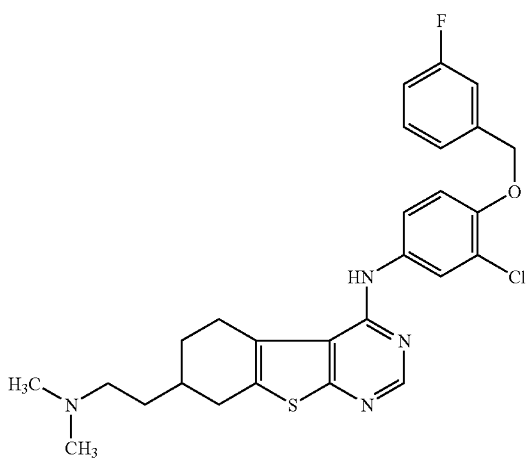 | 2.73 | 511 |
| 165 | 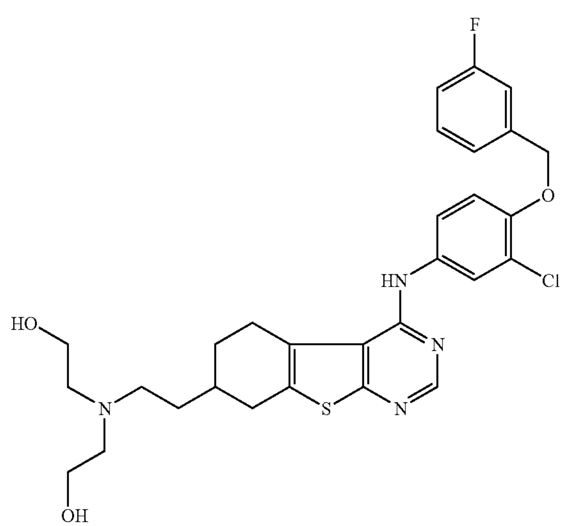 | 2.53 | 571 |

TABLE 1-continued
| Ex. No. | Structure | LCMS RT (min)[a] or TLC R_f [solvent] | LCMS Ion [M + H]+ |
|---|---|---|---|
| 166 | 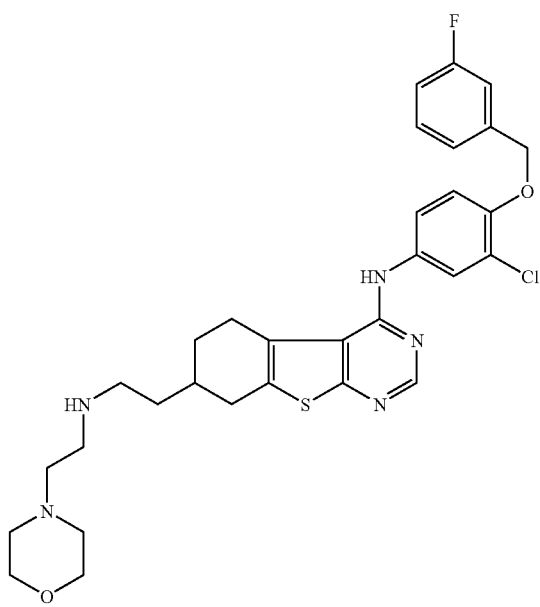 | 2.55 | 596 |
| 167 | 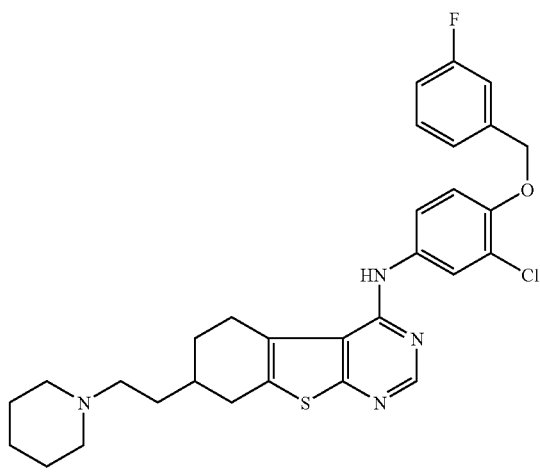 | 2.86 | 551 |

TABLE 1-continued
| Ex. No. | Structure | LCMS RT (min)[a] or TLC $R_f$ [solvent] | LCMS Ion [M + H]+ |
|---|---|---|---|
| 168 | 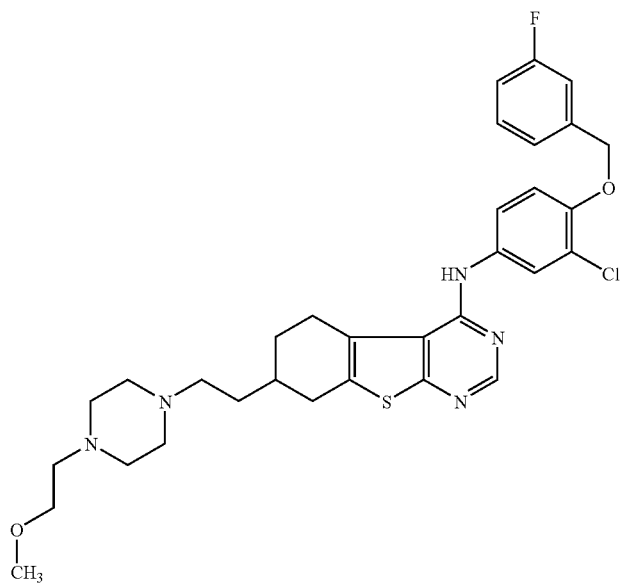 | 2.68 | 610 |
| 169 | 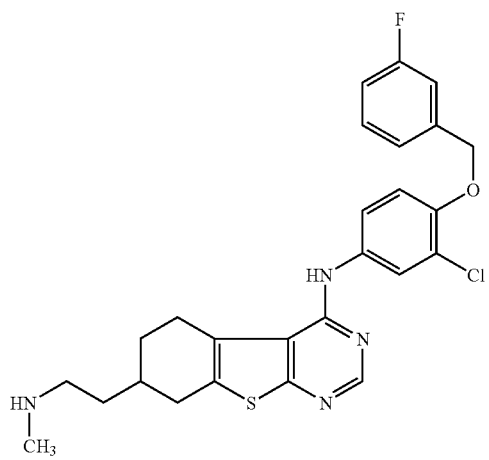 | 2.82 | 497 |

TABLE 1-continued
| Ex. No. | Structure | LCMS RT (min)[a] or TLC R_f [solvent] | LCMS Ion [M + H]+ |
|---|---|---|---|
| 170 | 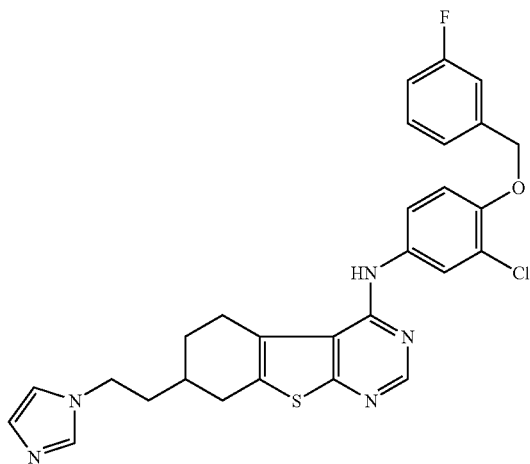 | 3.24 | 534 |
| 171 | 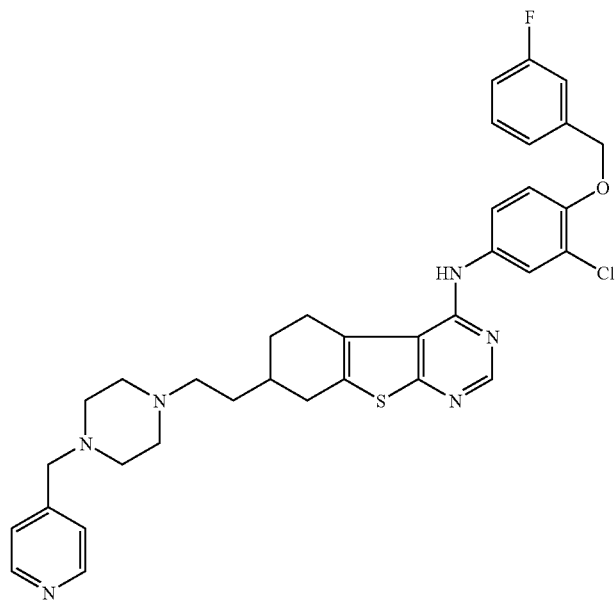 | 2.94 | 643 |

US 7,238,701 B2
TABLE 1-continued
| Ex. No. | Structure | LCMS RT (min)ª or TLC R_f [solvent] | LCMS Ion [M + H]+ |
|---|---|---|---|
| 172 | 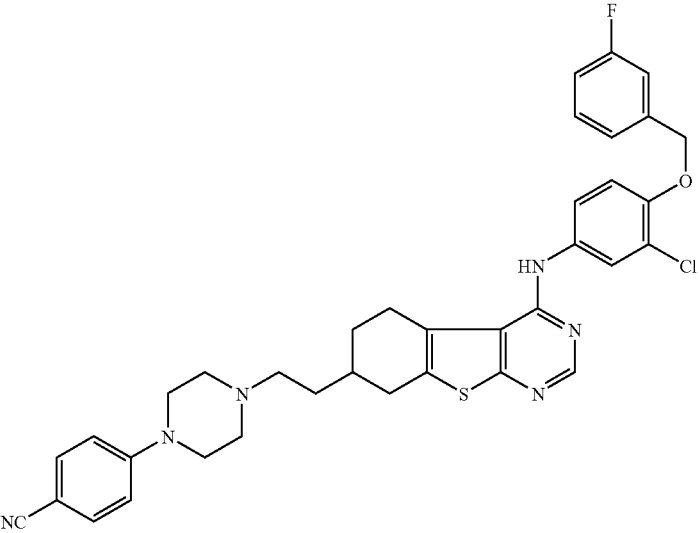 | 3.44 | 653 |
| 173 | 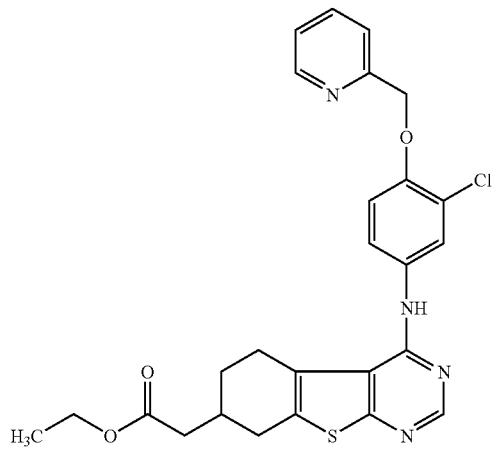 | 3.18 | 509 |
| 174 | 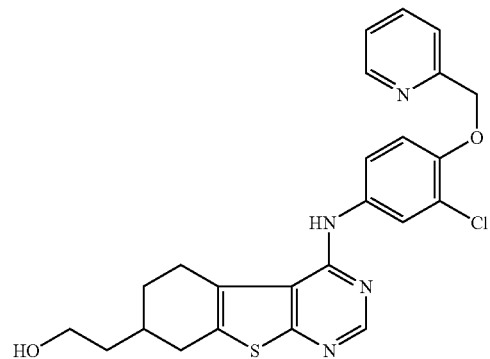 | 3.03 | 467 |

TABLE 1-continued
| Ex. No. | Structure | LCMS RT (min)[a] or TLC R_f [solvent] | LCMS Ion [M + H]+ |
|---|---|---|---|
| 175 | 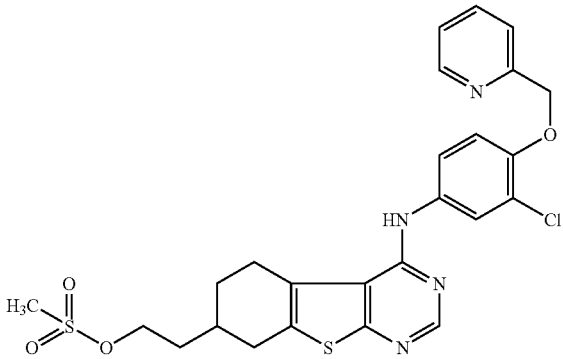 | 3.03 | 545 |
| 176 | 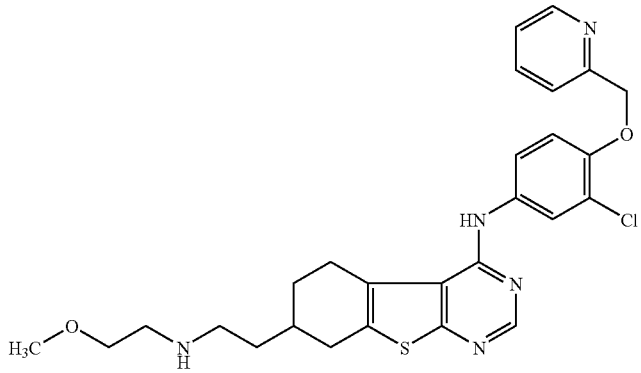 | 2.23 | 524 |
| 177 | 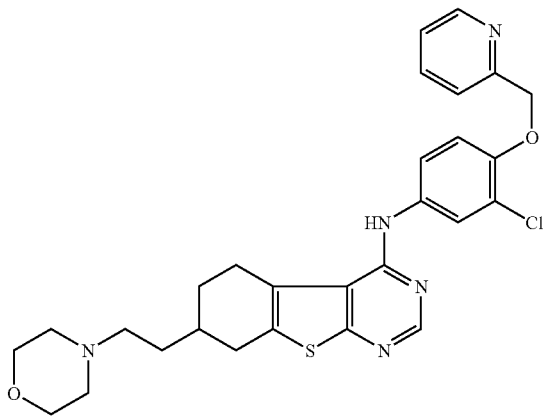 | 2.25 | 536 |

TABLE 1-continued

| Ex. No. | Structure | LCMS RT (min)a or TLC Rf [solvent] | LCMS Ion [M + H]+ |
|---|---|---|---|
| 178 | 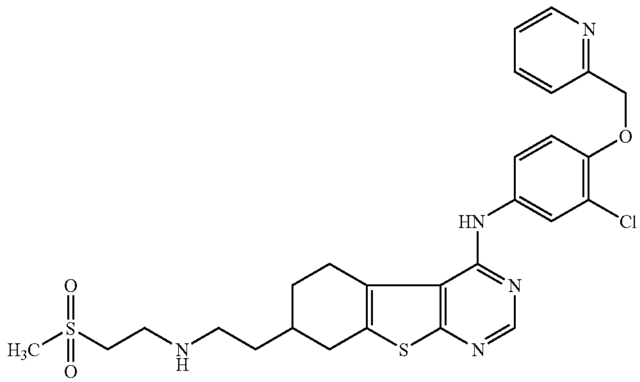 | 2.23 | 572 |
| 179 | 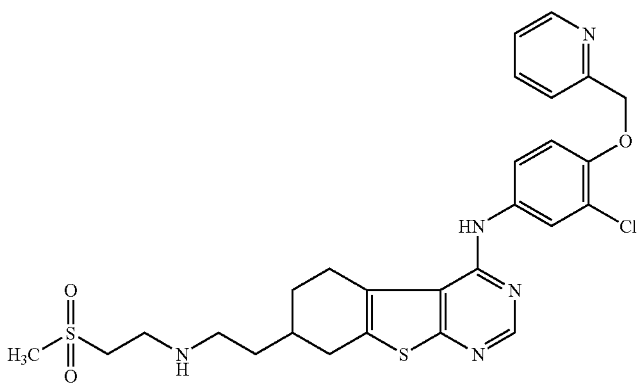 | 2.22 | 554 |
| 180 | 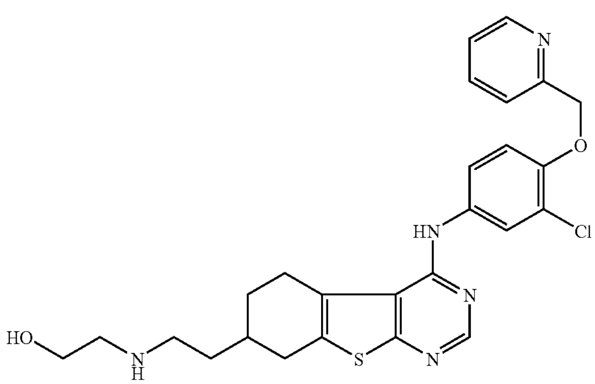 | 2.15 | 510 |

TABLE 1-continued

| Ex. No. | Structure | LCMS RT (min)[a] or TLC R$_f$ [solvent] | LCMS Ion [M + H]+ |
|---|---|---|---|
| 181 | 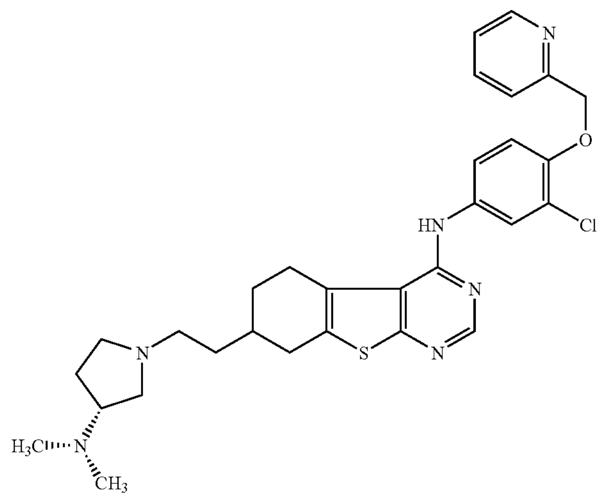 | 2.06 | 563 |
| 182 | 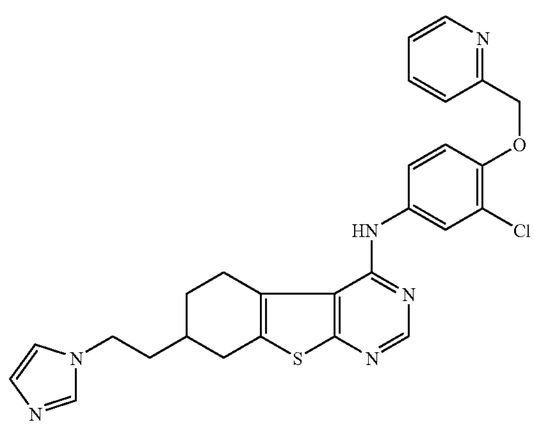 | 2.23 | 517 |
| 183 | 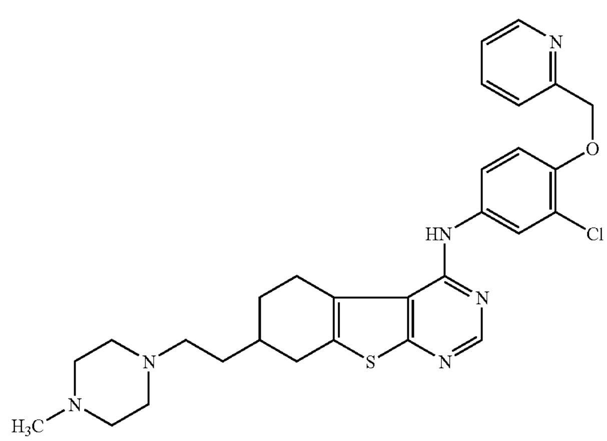 | 2.08 | 549 |

TABLE 1-continued
| Ex. No. | Structure | LCMS RT (min)ª or TLC R_f [solvent] | LCMS Ion [M + H]⁺ |
|---|---|---|---|
| 184 | 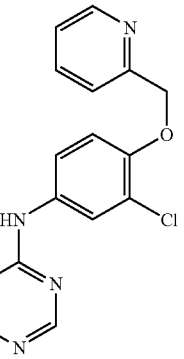 | 1.22 | 537 |
| 185 | 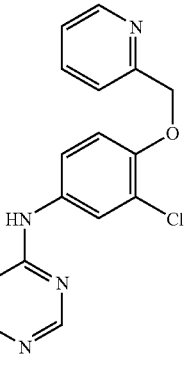 | 2.17 | 494 |
| 186 | 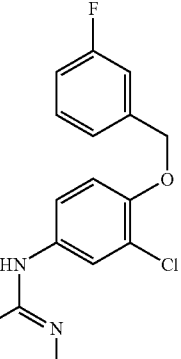 | 2.59 | 553 |

TABLE 1-continued
| Ex. No. | Structure | LCMS RT (min)ᵃ or TLC R_f [solvent] | LCMS Ion [M + H]⁺ |
|---|---|---|---|
| 187 | 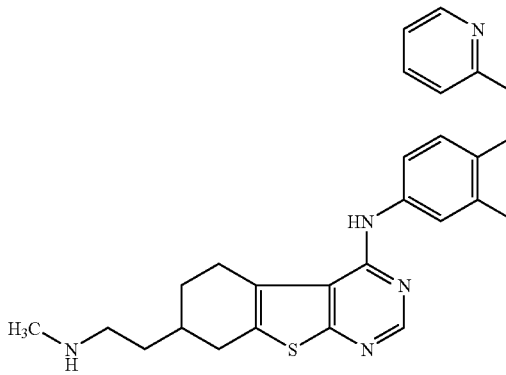 | 2.16 | 480 |
| 188 | 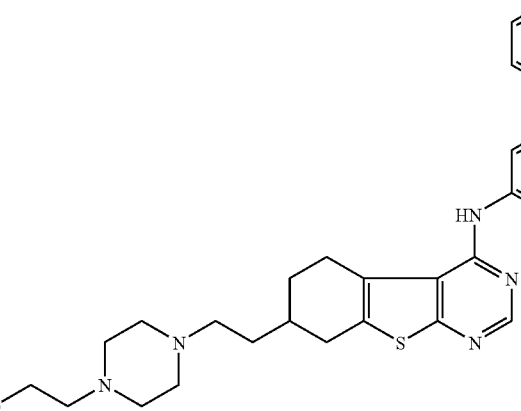 | 2.08 | 593 |
| 189 | 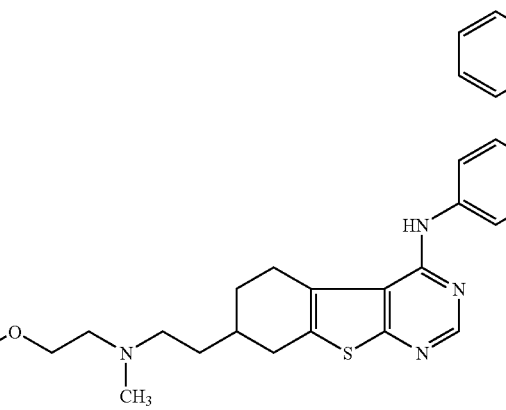 | 2.23 | 538 |

TABLE 1-continued

| Ex. No. | Structure | LCMS RT (min)[a] or TLC R_f [solvent] | LCMS Ion [M + H]+ |
|---|---|---|---|
| 190 | 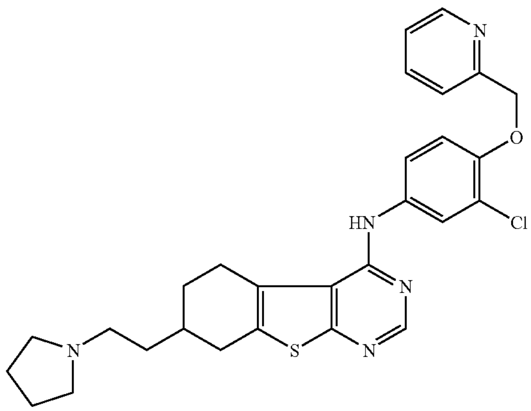 | 1.24 | 520 |
| 191 | 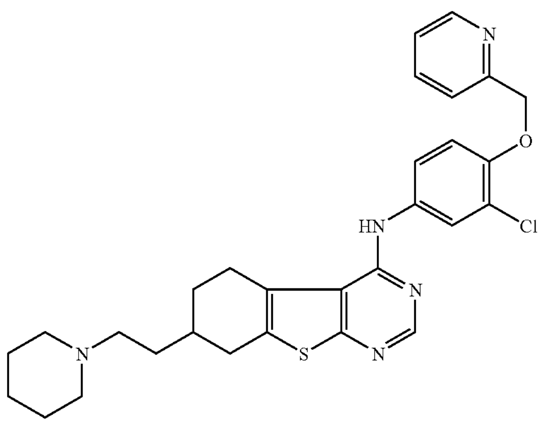 | 1.26 | 534 |
| 192 | 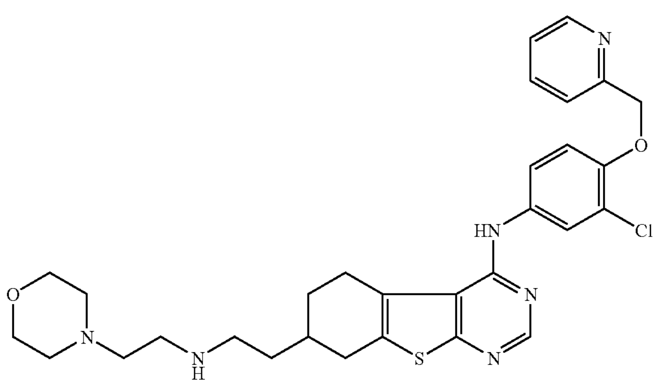 | 1.17 | 579 |

TABLE 1-continued
| Ex. No. | Structure | LCMS RT (min)[a] or TLC R_f [solvent] | LCMS Ion [M + H]+ |
|---|---|---|---|
| 193 | 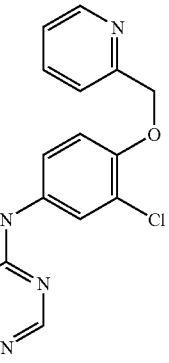 | 2.61 | 494 |
| 194 | 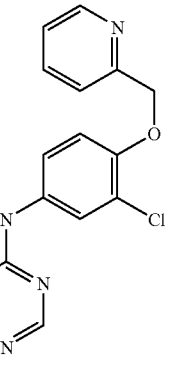 | 2.68 | 522 |
| 195 | 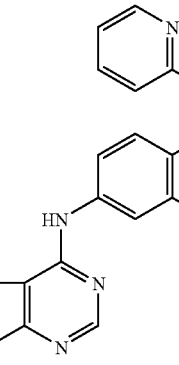 | 2.69 | 538 |

TABLE 1-continued

| Ex. No. | Structure | LCMS RT (min)[a] or TLC R_f [solvent] | LCMS Ion [M + H]+ |
|---|---|---|---|
| 196 | 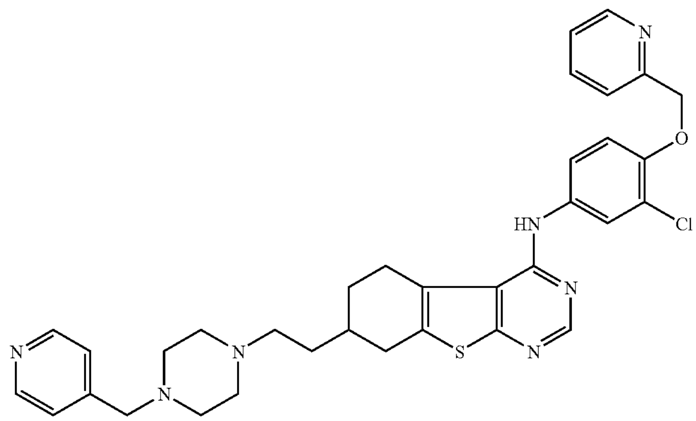 | 2.45 | 626 |
| 197 | 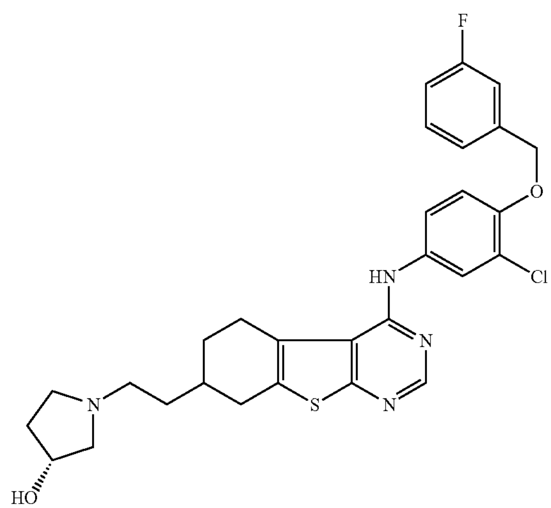 | 2.61 | 553 |
| 198 | 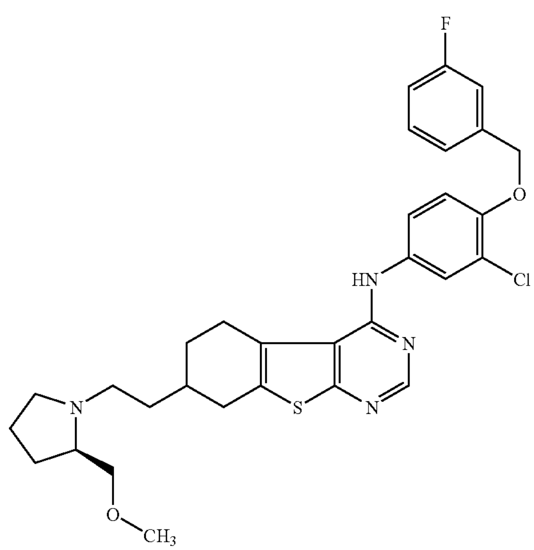 | 2.76 | 581 |

TABLE 1-continued
| Ex. No. | Structure | LCMS RT (min)[a] or TLC R$_f$ [solvent] | LCMS Ion [M + H]$^+$ |
|---|---|---|---|
| 199 | 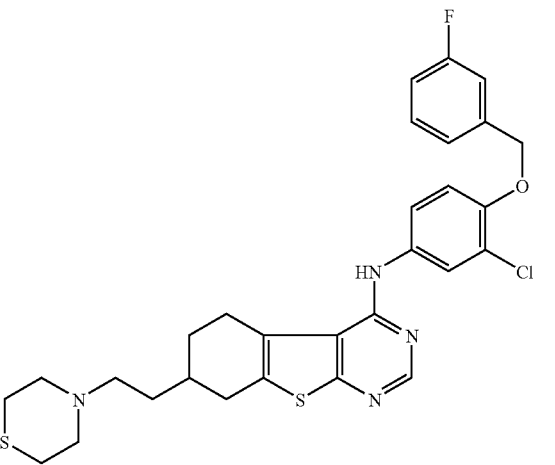 | 2.74 | 569 |
| 200 | 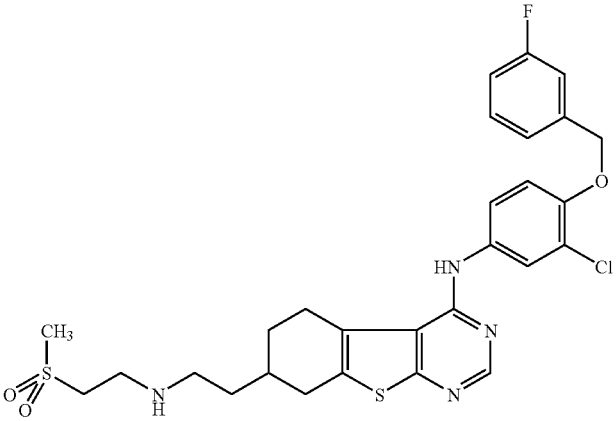 | R$_f$ = 0.25 [5% MeOH/ DCM] | 589.2 |
| 201 | 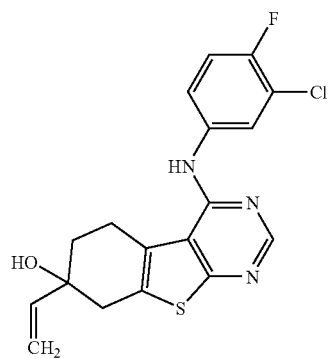 | 3.09 | 376 |

TABLE 1-continued

| Ex. No. | Structure | LCMS RT (min)[a] or TLC R_f [solvent] | LCMS Ion [M + H]+ |
| --- | --- | --- | --- |
| 202 | 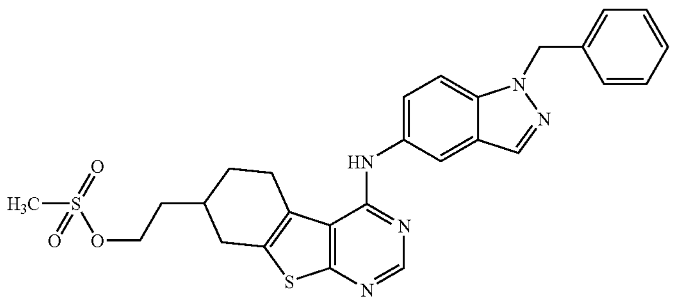 | R_f = 0.22 [5% MeOH/ DCM] | 534 |
| 203 | 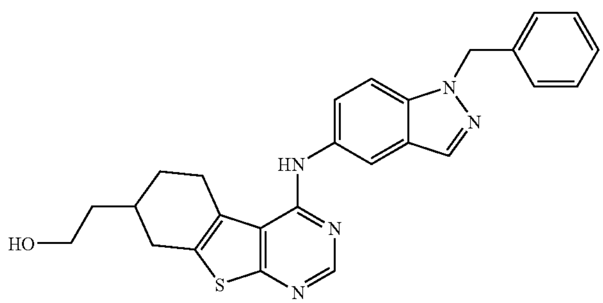 | R_f = 0.69 [10% MeOH/ DCM] | 456 |
| 204 | 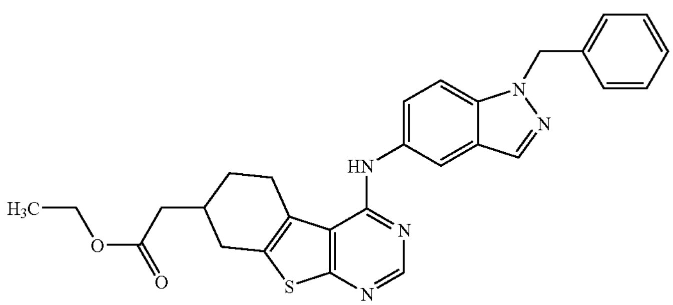 | R_f = 0.53 [5% MeOH/ DCM] | 498 |
| 205 | 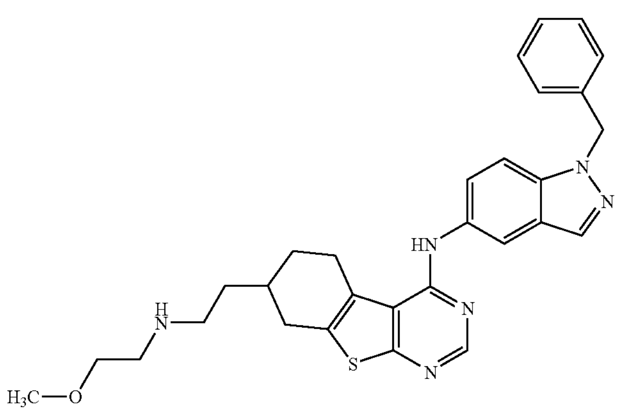 | R_f = 0.55 [15% MeOH/ DCM] | 513 |

TABLE 1-continued

| Ex. No. | Structure | LCMS RT (min)[a] or TLC R$_f$ [solvent] | LCMS Ion [M + H]+ |
|---|---|---|---|
| 206 | 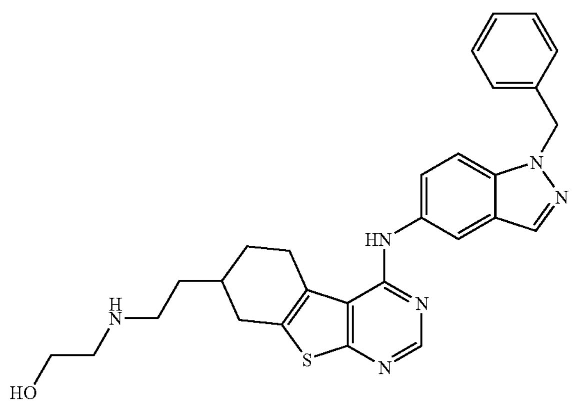 | R$_f$ = 0.23 [50% MeOH/ DCM] | 499 |
| 207 | 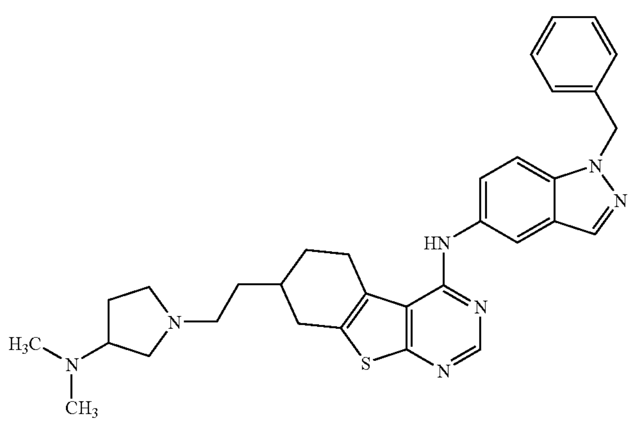 | R$_f$ = 0.14 [20% MeOH/ DCM] | 552 |
| 208 | 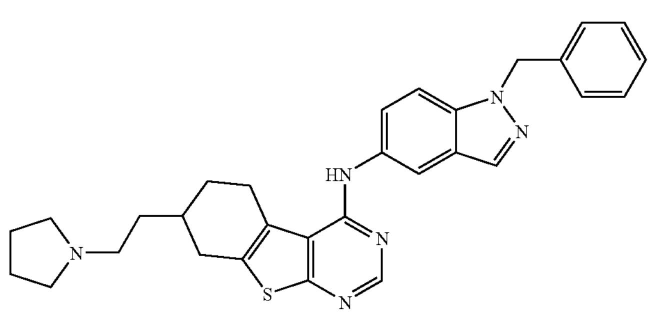 | R$_f$ = 0.59 [20% MeOH/ DCM] | 509 |

TABLE 1-continued

| Ex. No. | Structure | LCMS RT (min)[a] or TLC R$_f$ [solvent] | LCMS Ion [M + H]$^+$ |
|---|---|---|---|
| 209 | 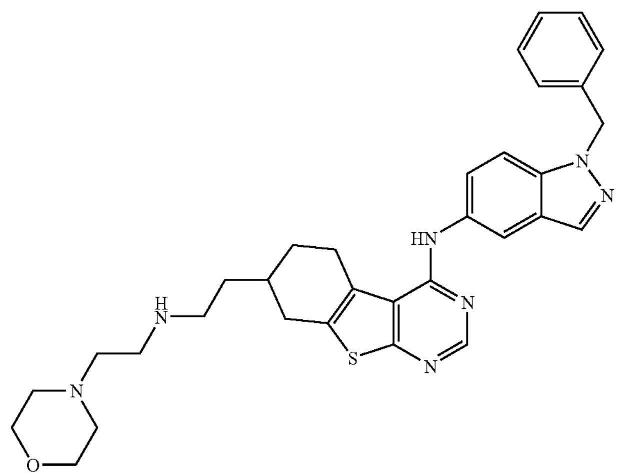 | R$_f$ = 0.51 [20% MeOH IN DCM] | 568 |
| 210 | 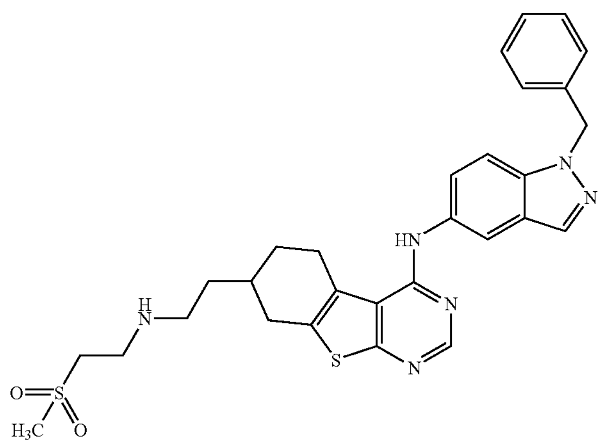 | R$_f$ = 0.68 [20% MeOH IN DCM] | 561 |
| 211 | 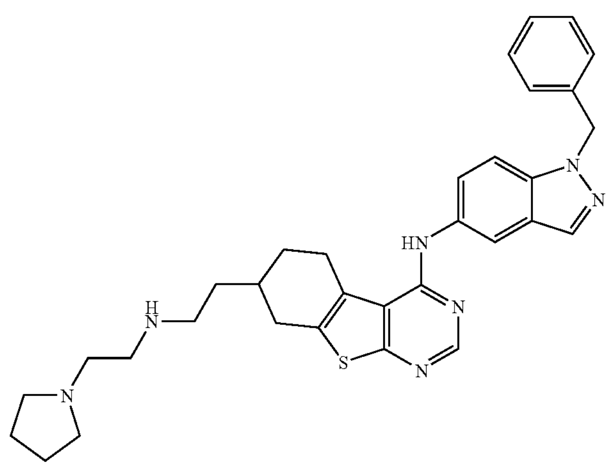 | R$_f$ = 0.24 [20% MeOH IN DCM] | 552 |

TABLE 1-continued

| Ex. No. | Structure | LCMS RT (min)[a] or TLC R_f [solvent] | LCMS Ion [M + H]+ |
| --- | --- | --- | --- |
| 212 | 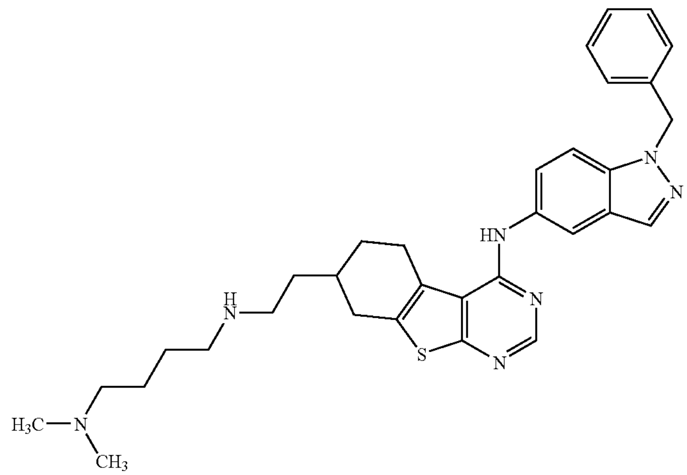 | R_f = 0.10 [20% MeOH IN DCM] | 554 |
| 213 | 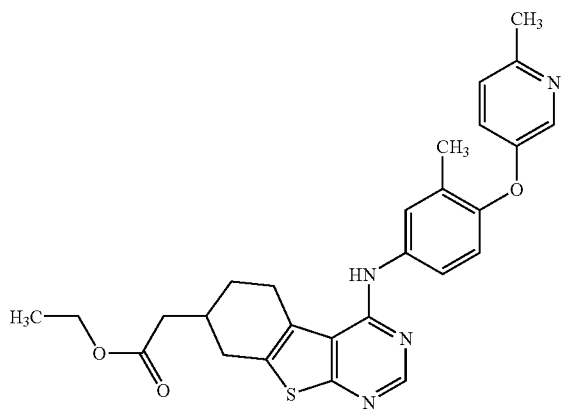 | R_f = 0.44 [2:1 EtOAc/ Hex] | 489 |
| 214 | 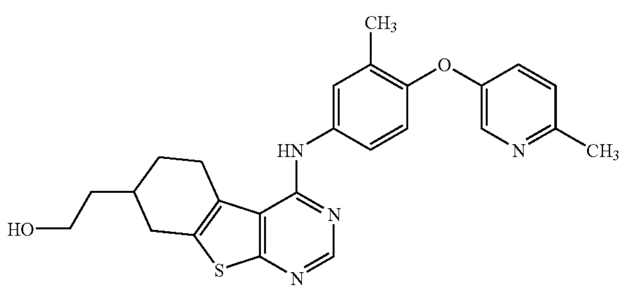 | R_f = 0.69 [10% MeOH IN DCM] | 447 |
| 215 | 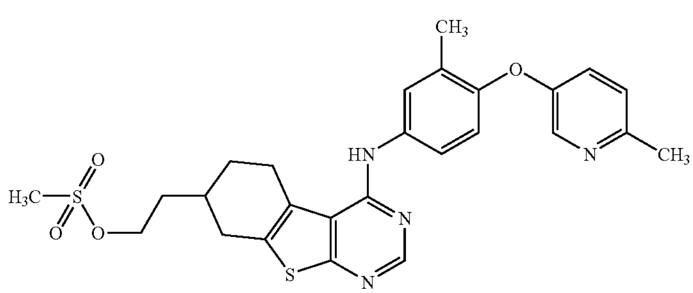 | R_f = 0.42 [EtOAc] | 525 |

TABLE 1-continued

| Ex. No. | Structure | LCMS RT (min)[a] or TLC R$_f$ [solvent] | LCMS Ion [M + H]$^+$ |
|---|---|---|---|
| 216 | 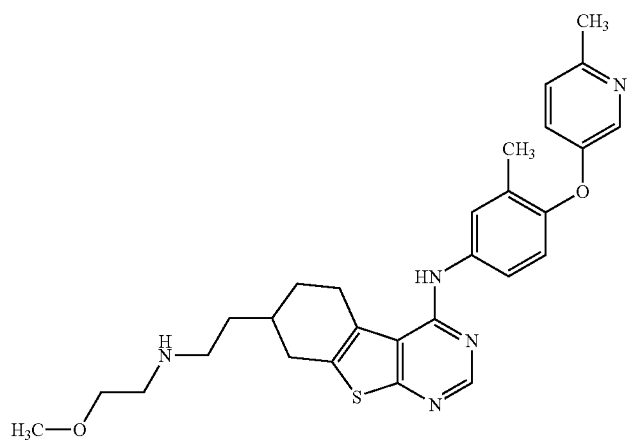 | 0.86 | 504 |
| 217 | 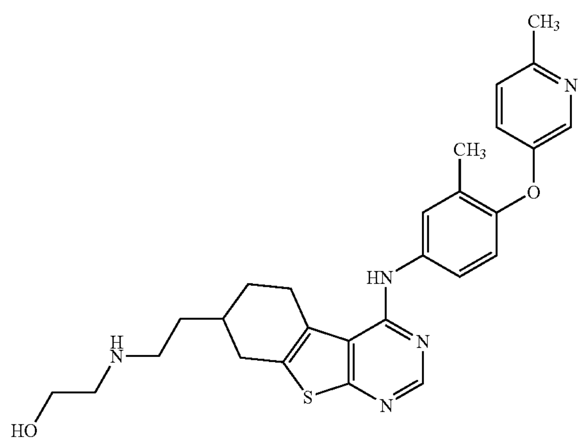 | 0.85 | 490 |
| 218 | 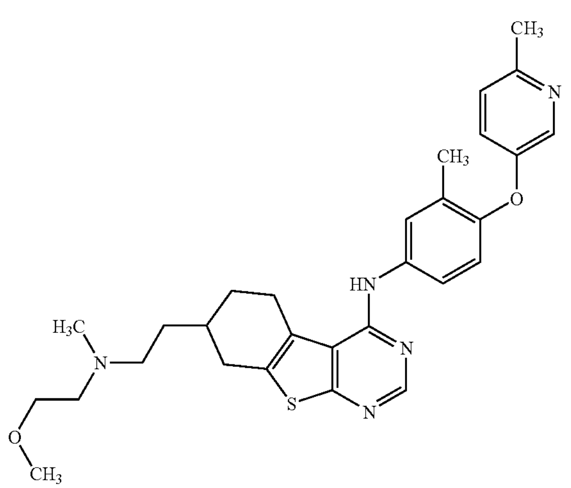 | R$_f$ = 0.76 [20:80 MeOH/ DCM] | 518 |

TABLE 1-continued

| Ex. No. | Structure | LCMS RT (min)ᵃ or TLC R_f [solvent] | LCMS Ion [M + H]⁺ |
|---|---|---|---|
| 219 | 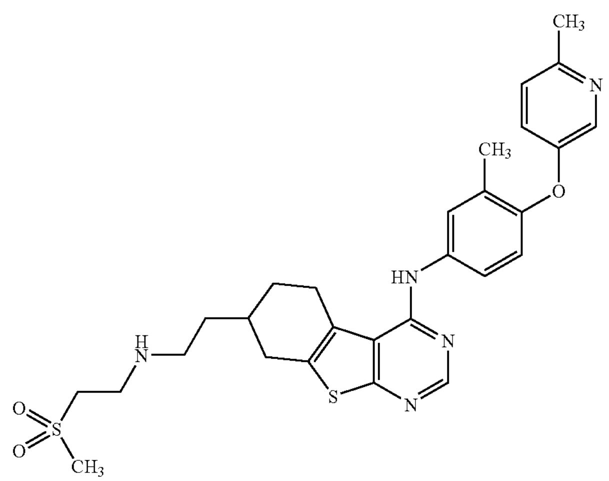 | 0.87 | 552 |
| 220 | 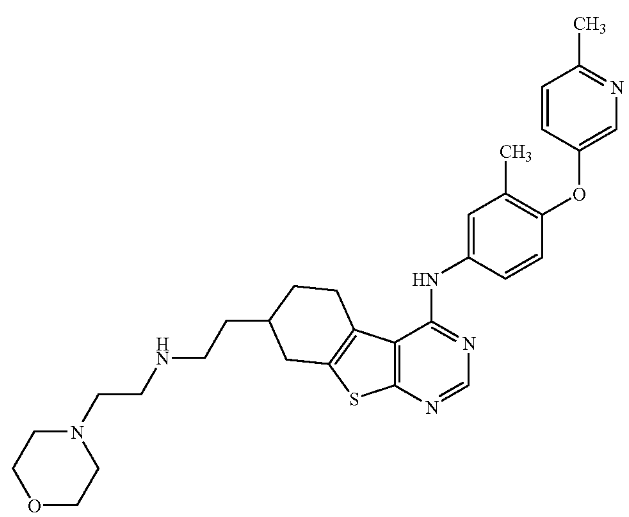 | 1.01 | 559 |
| 221 | 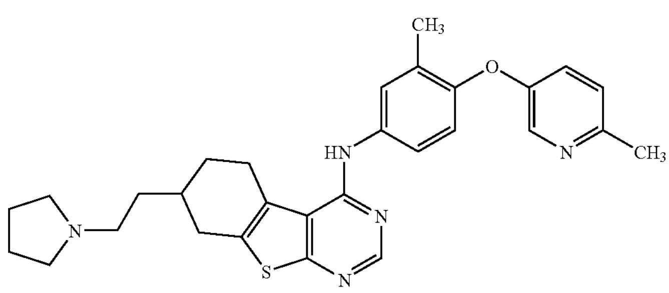 | 0.93 | 500 |

TABLE 1-continued

| Ex. No. | Structure | LCMS RT (min)ᵃ or TLC R_f [solvent] | LCMS Ion [M + H]⁺ |
|---|---|---|---|
| 222 | 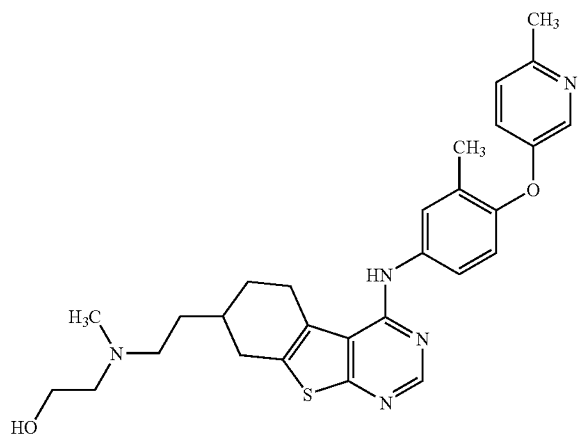 | 0.84 | 504 |
| 223 | 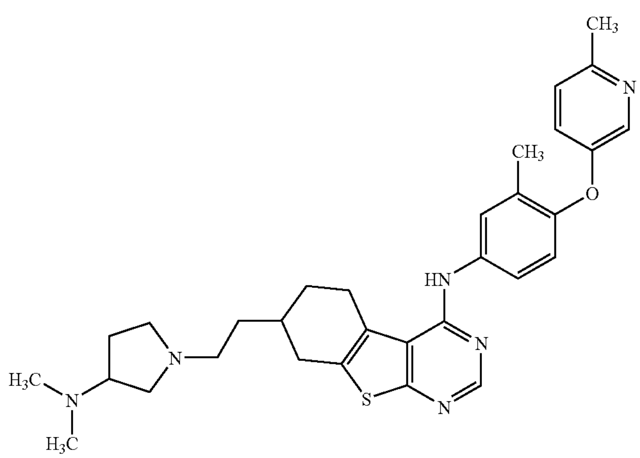 | 0.87 | 543 |
| 224 | 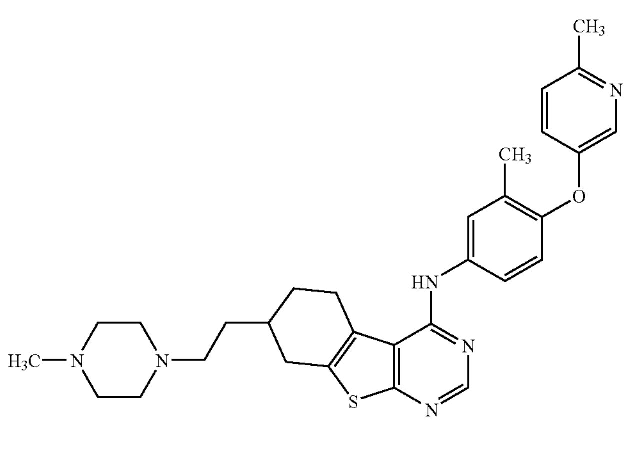 | 0.83 | 529 |

TABLE 1-continued

| Ex. No. | Structure | LCMS RT (min)[a] or TLC R$_f$ [solvent] | LCMS Ion [M + H]$^+$ |
|---|---|---|---|
| 225 | 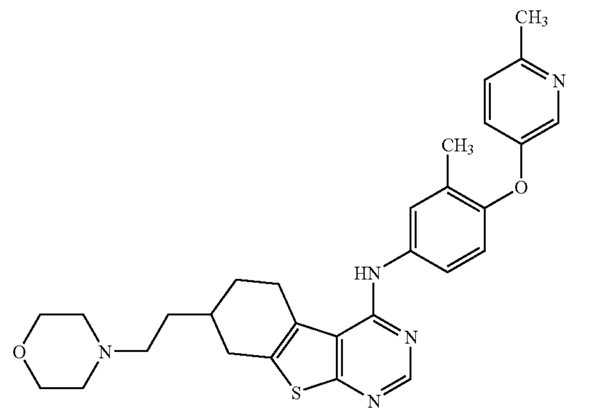 | 0.83 | 516 |
| 226 | 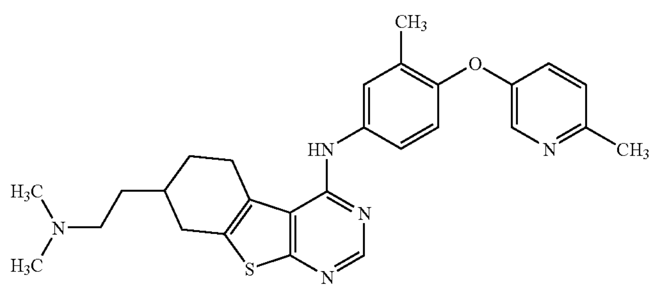 | 0.83 | 474 |
| 227 | 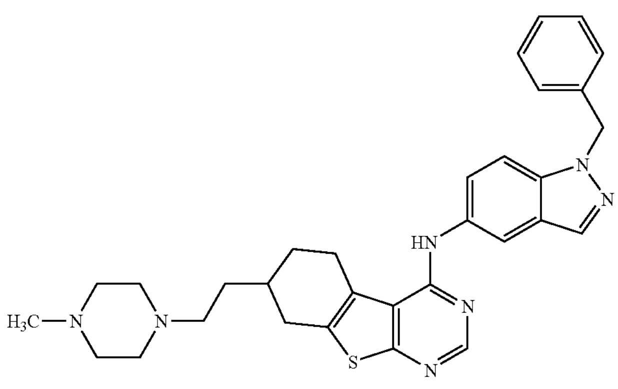 | 2.59 | 538 |
| 228 | 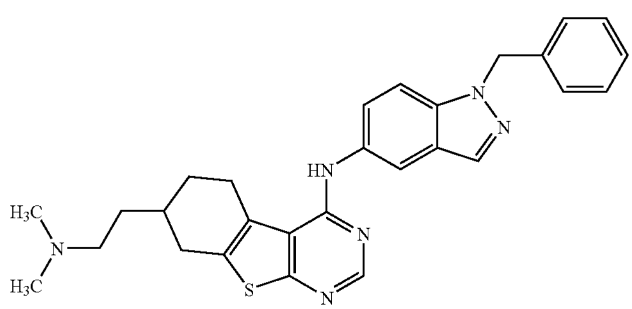 | R$_f$ = 0.25 [20:80 MeOH/DCM] | 483 |

TABLE 1-continued

| Ex. No. | Structure | LCMS RT (min)[a] or TLC R_f [solvent] | LCMS Ion [M + H]+ |
|---|---|---|---|
| 229 | 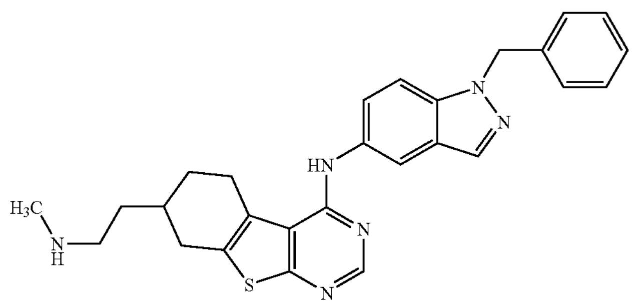 | 2.74 | 469 |
| 230 | 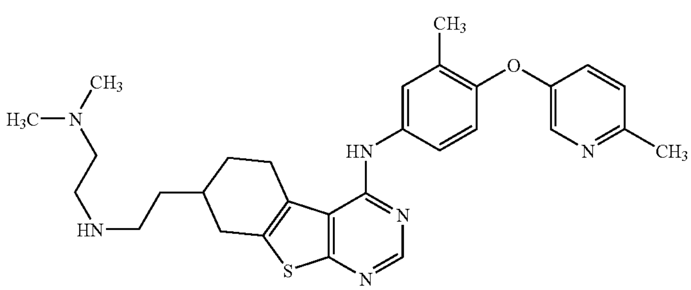 | 1.09 | 517 |
| 231 | 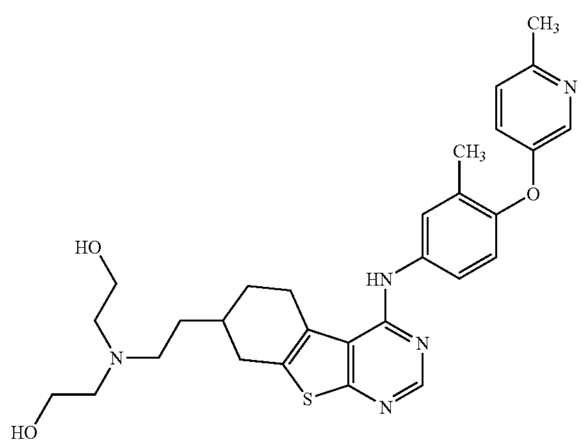 | 2.26 | 534 |
| 232 | 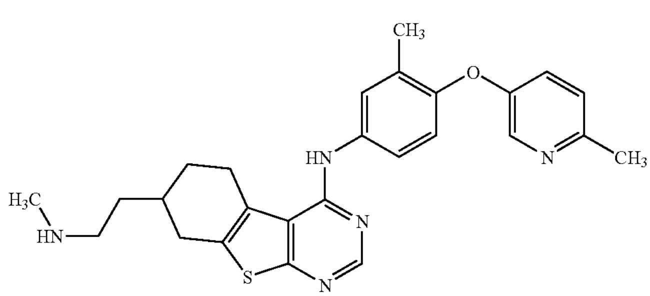 | 1.20 | 460 |

TABLE 1-continued

| Ex. No. | Structure | LCMS RT (min)[a] or TLC R_f [solvent] | LCMS Ion [M + H]+ |
|---|---|---|---|
| 233 | 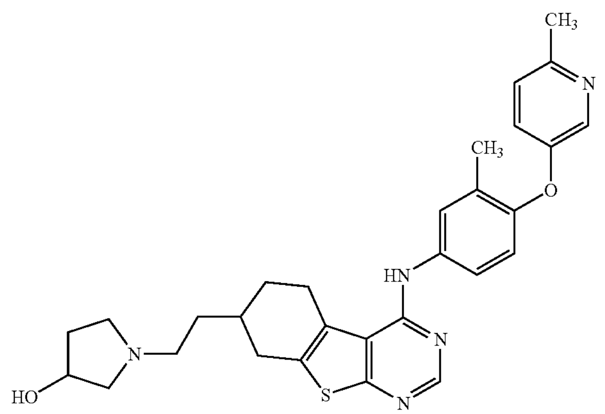 | 1.00 | 516 |
| 234 | 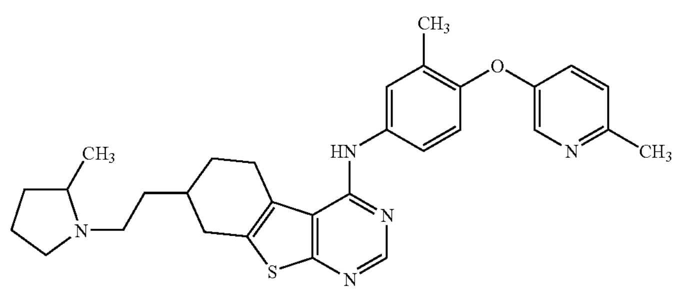 | 1.39 | 514 |
| 235 | 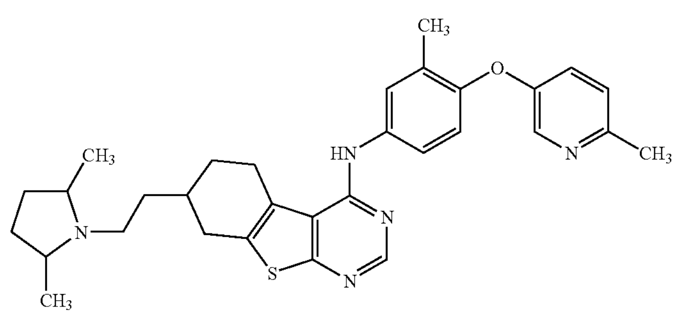 | 1.97 | 528 |
| 236 | 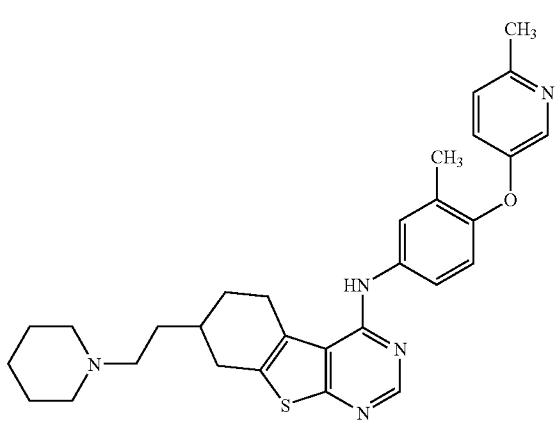 | 1.38 | 514 |

TABLE 1-continued

| Ex. No. | Structure | LCMS RT (min)[a] or TLC R_f [solvent] | LCMS Ion [M + H]+ |
|---|---|---|---|
| 237 | 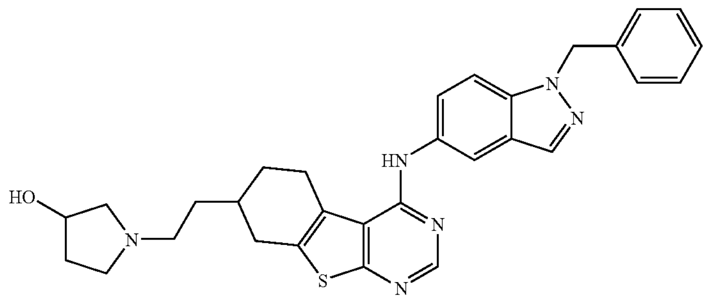 | 2.04 | 525 |
| 238 | 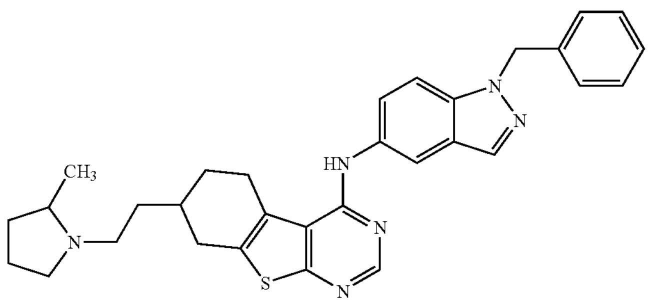 | 2.50 | 523 |
| 239 | 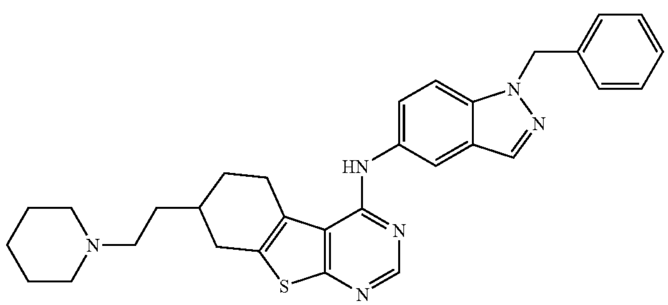 | 2.47 | 523 |
| 240 | 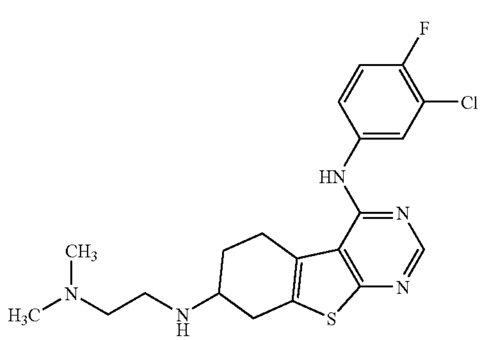 | 2.06 | 420 |

TABLE 1-continued

| Ex. No. | Structure | LCMS RT (min)[a] or TLC R$_f$ [solvent] | LCMS Ion [M + H]$^+$ |
|---|---|---|---|
| 241 | 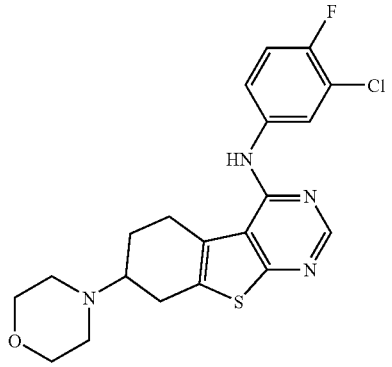 | 2.61 | 419 |
| 242 | 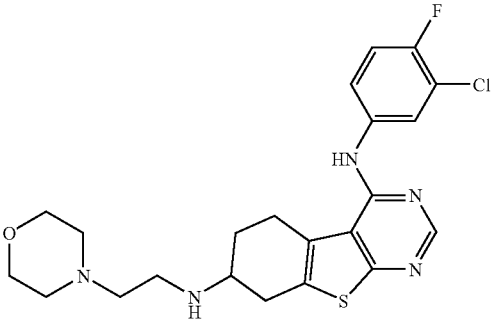 | 1.89 | 462 |
| 243 | 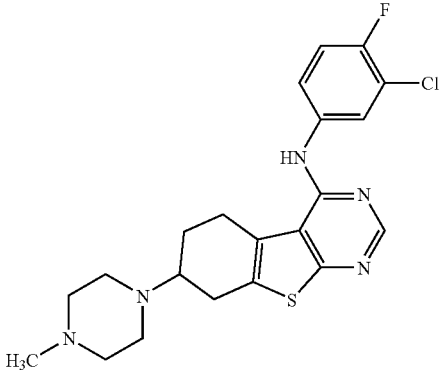 | 2.55 | 432 |

[a] Analytical HPLC were obtained using a Gilson HPLC equipped with a quaternary pump, a variable wavelength detector set at 254 nm, a YMC pro C-18 column (50 × 4.6 mm, 12 μm). The eluents were A: acetonitrile w/0.1% TEA and B: H$_2$O w/0.1% TFA. Gradient elution from 10% B to 90% over 4 mm at a flowrate of 4.0 mL/min was used with an initial hold of 0.5 min and a final hold at 90% B of 0.5 minutes. Total run time was 5 min.

The compound structures of Table 1 correspond to the IUPAC compound names in Table 2 below.

TABLE 2

| Entry No. | IUPAC Name |
|---|---|
| 1 | 4-[(3-bromophenyl)amino]-5,6,7,8-tetrahydro[1]benzothieno[2,3-d]pyrimidine-7-carboxylic acid |
| 2 | 4-[(4-bromo-2-fluorophenyl)amino]-5,6,7,8-tetrahydro[1]benzothieno[2,3-d]pyrimidine-7-carboxylic acid |
| 3 | N-(3-chloro-4-fluorophenyl)-7-(1-piperidinylcarbonyl)-5,6,7,8-tetrahydro[1]benzothieno[2,3-d]pyrimidin-4-amine |
| 4 | N-(3-chloro-4-fluorophenyl)-7-(1-piperidinylmethyl)-5,6,7,8-tetrahydro[1]benzothieno[2,3-d]pyrimidin-4-amine |
| 5 | N-(3-chloro-4-fluorophenyl)-7-(4-morpholinylcarbonyl)-5,6,7,8-tetrahydro[1]benzothieno[2,3-d]pyrimidin-4-amine |
| 6 | N-(4-bromo-2-fluorophenyl)-7-(1-piperidinylcarbonyl)-5,6,7,8-tetrahydro[1]benzothieno[2,3-d]pyrimidin-4-amine |
| 7 | N-(4-bromo-2-fluorophenyl)-7-(1-piperidinylmethyl)-5,6,7,8-tetrahydro[1]benzothieno[2,3-d]pyrimidin-4-amine |
| 8 | 4-[(3-chloro-4-fluorophenyl)amino]-N-(2-methoxyethyl)-N-methyl-5,6,7,8-tetrahydro[1]benzothieno[2,3-d]pyrimidine-7-carboxamide |
| 9 | N-(4-bromo-2-fluorophenyl)-7-(4-morpholinylcarbonyl)-5,6,7,8-tetrahydro[1]benzothieno[2,3-d]pyrimidin-4-amine |
| 10 | 4-[(4-bromo-2-fluorophenyl)amino]-N-(2-methoxyethyl)-N-methyl-5,6,7,8-tetrahydro[1]benzothieno[2,3-d]pyrimidin-7-carboxamide |
| 11 | N-(3-chloro-4-fluorophenyl)-7-{[(2-methoxyethyl)(methyl)amino]methyl}-5,6,7,8-tetrahydro[1]benzothieno[2,3-d]pyrimidin-4-amine |
| 12 | N-(3-chloro-4-fluorophenyl)-7-(4-morpholinylmethyl)-5,6,7,8-tetrahydro[1]benzothieno[2,3-d]pyrimidin-4-amine |
| 13 | N-(3-chloro-4-fluorophenyl)-7-[(4-methyl-1-piperazinyl)carbonyl]-5,6,7,8-tetrahydro[1]benzothieno[2,3-d]pyrimidin-4-amine |
| 14 | Ethyl 4-[(3-bromophenyl)amino]-5,6,7,8-tetrahydro[1]benzothieno[2,3-d]pyrimidine-7-carboxylate |
| 15 | N-(3-chloro-4-fluorophenyl)-7-[(4-methyl-1-piperazinyl)methyl]-5,6,7,8-tetrahydro[1]benzothieno[2,3-d]pyrimidin-4-amine |
| 16 | 4-[(3-chloro-4-fluorophenyl)amino]-N-(2-methoxyethyl)-5,6,7,8-tetrahydro[1]benzothieno[2,3-d]pyrimidine-7-carboxamide |
| 17 | N-(3-chloro-4-fluorophenyl)-7-{[(2-methoxyethyl)amino]methyl}-5,6,7,8-tetrahydro[1]benzothieno[2,3-d]pyrimidin-4-amine |
| 18 | N-(3-bromophenyl)-7-(4-morpholinylcarbonyl)-5,6,7,8-tetrahydro[1]benzothieno[2,3-d]pyrimidin-4-amine |
| 19 | N-(4-bromo-2-fluorophenyl)-7-[(4-methyl-piperazinyl)carbonyl]-5,6,7,8-tetrahydro[1]benzothieno[2,3-d]pyrimidin-4-amine |
| 20 | 4-[(3-chloro-4-fluorophenyl)amino]-5,6,7,8-tetrahydro[1]benzothieno[2,3-d]pyrimidine-7-carboxylic acid |
| 21 | 4-[(3-bromphenyl)amino]-5,6,7,8-tetrahydro[1]benzothieno[2,3-d]pyrimidine-7-carboxylic acid |
| 22 | N-(3-bromophenyl)-7-[(4-methyl-1-piperazinyl)carbonyl]-5,6,7,8-tetrahydro[1]benzothieno[2,3-d]pyrimidin-4-amine |
| 23 | 4-[(4-bromo-2-fluorophenyl)amino]-N-(2-methoxyethyl)-5,6,7,8-tetrahydro[1]benzothieno[2,3-d]pyrimidin-7-carboxamide |
| 24 | ethyl 4-[(3-chloro-4-fluorophenyl)amino]-5,6,7,8-tetrahydro[1]benzothieno[2,3-d]pyrimidine-7-carboxylate |
| 25 | N-(3-bromophenyl)-7-(4-morpholinylmethyl)-5,6,7,8-tetrahydro[1]benzothieno[2,3-d]pyrimidin-4-amine |
| 26 | N-(3-bromophenyl)-7-[(4-methyl-1-piperazinyl)methyl]-5,6,7,8-tetrahydro[1]benzothieno[2,3-d]pyrimidin-4-amine |
| 27 | N-(3-bromophenyl)-7-(1-piperidinylcarbonyl)-5,6,7,8-tetrahydro[1]benzothieno[2,3-d]pyrimidin-4-amine |
| 28 | 4-[(3-chloro-4-fluorophenyl)amino]-N-(3-methoxypropyl)-5,6,7,8-tetrahydro[1]benzothieno[2,3-d]pyrimidine-7-carboxamide |
| 29 | 4-[(3-bromophenyl)amino]-N-(2-methoxyethyl)-5,6,7,8-tetrahydro[1]benzothieno[2,3-d]pyrimidine-7-carboxamide |
| 30 | N-(3-bromophenyl)-7-(1-piperidinylmethyl)-5,6,7,8-tetrahydro[1]benzothieno[2,3-d]pyrimidin-4-amine |
| 31 | 4-[(3-bromophenyl)amino]-N-(2-methoxyethyl)-N-methyl-5,6,7,8-tetrahydro[1]benzothieno[2,3-d]pyrimidine-7-carboxamide |
| 32 | Ethyl 4-{[4-(benzyloxy)phenyl]amino}-5,6,7,8-tetrahydro[1]benzothieno[2,3-d]pyrimidine-7-carboxylate |
| 33 | N-(3-chloro-4-fluorophenyl)-7-{[(3-methoxypropyl)amino]methyl}-5,6,7,8-tetrahydro[1]benzothieno[2,3-d]pyrimidin-4-amine |
| 34 | N-(4-bromo-2-fluorophenyl)-7-{[(2-methoxyethyl)amino]methyl}-5,6,7,8-tetrahydro[1]benzothieno[2,3-d]pyrimidin-4-amine |
| 35 | N-(4-bromo-2-fluorophenyl)-7-(4-morpholinylmethyl)-5,6,7,8-tetrahydro[1]benzothieno[2,3-d]pyrimidin-4-amine |
| 36 | N-(3-bromophenyl)-7-{[(2-methoxyethyl)(methyl)amino]methyl}-5,6,7,8-tetrahydro[1]benzothieno[2,3-d]pyrimidin-4-amine |

TABLE 2-continued

| Entry No. | IUPAC Name |
|---|---|
| 37 | N-(3-bromophenyl)-7-{[(2-methoxyethyl)amino]methyl}-5,6,7,8-tetrahydro[1]benzothieno[2,3-d]pyrimidin-4-amine |
| 38 | N-(3-bromophenyl)-7-({[2-(4-morpholinyl)ethyl]amino}methyl)-5,6,7,8-tetrahydro[1]benzothieno[2,3-d]pyrimidin-4-amine |
| 39 | Ethyl 4-[(3-hydroxy-4-methylphenyl)amino]-5,6,7,8-tetrahydro[1]benzothieno[2,3-d]pyrimidine-7-carboxylate |
| 40 | Ethyl 4-[(3-hydroxyphenyl)amino]-5,6,7,8-tetrahydro[1]benzothieno[2,3-d]pyrimidine-7-carboxylate |
| 41 | Ethyl 4-[(2-fluoro-4-iodophenyl)amino]-5,6,7,8-tetrahydro[1]benzothieno[2,3-d]pyrimidine-7-carboxylate |
| 42 | Ethyl 4-[(4-chloro-2-fluorophenyl)amino]-5,6,7,8-tetrahydro[1]benzothieno[2,3-d]pyrimidine-7-carboxylate |
| 43 | N-[4-(benzyloxy)phenyl]-7-[(4-methyl-1-piperazinyl)carbonyl]-5,6,7,8-tetrahydro[1]benzothieno[2,3-d]pyrimidin-4-amine |
| 44 | Ethyl 4-[(2-fluoro-4-methylphenyl)amino]-5,6,7,8-tetrahydro[1]benzothieno[2,3-d]pyrimidine-7-carboxylate |
| 45 | N-(3-bromophenyl)-7-[2-(4-morpholinyl)ethyl]-5,6,7,8-tetrahydro[1]benzothieno[2,3-d]pyrimidin-4-amine |
| 46 | 4-[(3-hydroxy-4-methylphenyl)amino]-5,6,7,8tetrahydro[1]benzothieno[2,3-d]pyrimidine-7-carboxylic acid |
| 47 | 4-[(3-hydroxyphenyl)amino]-5,6,7,8-tetrahydro[1]benzothieno[2,3-d]pyrimidine-7-carboxylic acid |
| 48 | 4-[4-({4-[(3-bromophenyl)amino]-5,6,7,8-tetrahydro[1]benzothieno[2,3-d]pyrimidin-7-yl}carbonyl)-1-piperazinyl]benzonitrile |
| 49 | N-(3-bromophenyl)-7-{[4-(4-methoxyphenyl)-1-piperazinyl]carbonyl}-5,6,7,8-tetrahydro[1]benzothieno[2,3-d]pyrimidin-4-amine |
| 50 | 4-[(2-fluoro-4-iodophenyl)amino]-5,6,7,8-tetrahydro[1]benzothieno[2,3-d]pyrimidine-7-carboxylic acid |
| 51 | 4-[(4-chloro-2-fluorophenyl)amino]-5,6,7,8-tetrahydro[1]benzothieno[2,3-d]pyrimidine-7-carboxylic acid |
| 52 | 4-[(3-chloro-4-fluorophenyl)amino]-N-[2-(methylsulfonyl)ethyl]-5,6,7,8-tetrahydro[1]benzothieno[2,3-d]pyrimidine-7-carboxamide |
| 53 | 4-[(2-fluoro-4-methylphenyl)amino]-5,6,7,8-tetrahydro[1]benzothieno[2,3-d]pyrimidine-7-carboxylic acid |
| 54 | N-(3-chloro-4-fluorophenyl)-7-[2-(4-morpholinyl)ethyl]-5,6,7,8-tetrahydro[1]benzothieno[2,3-d]pyrimidin-4-amine |
| 55 | N-(3-chloro-4-fluorophenyl)-7-({[2-(methylsulfonyl)ethyl]amino}methyl)-5,6,7,8-tetrahydro[1]benzothieno[2,3-d]pyrimidin-4-amine |
| 56 | N-allyl-4-[(3-bromophenyl)amino]-5,6,7,8-tetrahydro[1]benzothieno[2,3-d]pyrimidine-7-carboxamide |
| 57 | ethyl {4-[(3-chloro-4-fluorophenyl)amino]-5,6,7,8-tetrahydro[1]benzothieno[2,3-d]pyrimidin-7-yl}acetate |
| 58 | N-(3-chloro-4-fluorophenyl)-7-[2-(4-methyl-1-piperazinyl)-2-oxoethyl]-5,6,7,8-tetrahydro[1]benzothieno[2,3-d]pyrimidin-4-amine |
| 59 | N-(3-chloro-4-fluorophenyl)-7-[2-(4-methyl-1-piperazinyl)ethyl]-5,6,7,8-tetrahydro[1]benzothieno[2,3-d]pyrimidin-4-amine |
| 60 | N-(3-bromophenyl)-7-{[(3R)-3-(dimethylamino)-1-pyrrolidinyl]carbonyl}-5,6,7,8-tetrahydro[1]benzothieno[2,3-d]pyrimidin-4-amine |
| 61 | N-(3-chloro-4-fluorophenyl)-7-[2-(4-morpholinyl)-2-oxoethyl]-5,6,7,8-tetrahydro[1]benzothieno[2,3-d]pyrimidin-4-amine |
| 62 | 2-{4-[(3-chloro-4-fluorophenyl)amino]-5,6,7,8-tetrahydro[1]benzothieno[2,3-d]pyrimidin-7-yl}-N-(2-methoxyethyl)acetamide |
| 63 | Ethyl {4-[(3-bromophenyl)amino]-5,6,7,8-tetrahydro[1]benzothieno[2,3-d]pyrimidin-7-yl}acetate |
| 64 | 2-{4-[(3-chloro-4-fluorophenyl)amino]-5,6,7,8-tetrahydro[1]benzothieno[2,3-d]pyrimidin-7-yl}ethanol |
| 65 | {4-[(3-bromophenyl)amino]-5,6,7,8-tetrahydro[1]benzothieno[2,3-d]pyrimidin-7-yl}acetic acid |
| 66 | N-(3-bromophenyl)-7-{[(3R)-3-(dimethylamino)-1-pyrrolidinyl]methyl}-5,6,7,8-tetrahydro[1]benzothieno[2,3-d]pyrimidin-4-amine |
| 67 | N-(3-chloro-4-fluorophenyl)-7-[2-oxo-2-(1-piperidinyl)ethyl]-5,6,7,8-tetrahydro[1]benzothieno[2,3-d]pyrimidin-4-amine |
| 68 | N-(3-bromophenyl)-7-[2-(4-methyl-1-piperazinyl)-2-oxoethyl]-5,6,7,8-tetrahydro[1]benzothieno[2,3-d]pyrimidin-4-amine |
| 69 | 2-{4-[(3-bromophenyl)amino]-5,6,7,8-tetrahydro[1]benzothieno[2,3-d]pyrimidin-7-yl}-N-[3-(4-morpholinyl)propyl]acetamide |
| 70 | N-(3-bromophenyl)-7-[2-(4-morpholinyl)-2-oxoethyl]-5,6,7,8-tetrahydro[1]benzothieno[2,3-d]pyrimidin-4-amine |
| 71 | N-(3-bromophenyl)-7-[2-oxo-2-(1-piperidinyl)ethyl]-5,6,7,8-tetrahydro[1]benzothieno[2,3-d]pyrimidin-4-amine |
| 72 | 4-[(3-chloro-4-fluorophenyl)amino]-5,6,7,8-tetrahydro[1]benzothieno[2,3-d]pyrimidin-7-yl}acetic acid |
| 73 | N-(3-chloro-4-fluorophenyl)-7-[2-(1-piperidinyl)ethyl]-5,6,7,8-tetrahydro[1]benzothieno[2,3-d]pyrimidin-4-amine |
| 74 | N-(3-chloro-4-fluorophenyl)-7-[2-(1-pyrrolidinyl)ethyl]-5,6,7,8-tetrahydro[1]benzothieno[2,3-d]pyrimidin-4-amine |

TABLE 2-continued

| Entry No. | IUPAC Name |
|---|---|
| 75 | N-(3-chloro-4-fluorophenyl)-7-{2-[(2-methoxyethyl)amino]ethyl}-5,6,7,8-tetrahydro[1]benzothieno[2,3-d]pyrimidin-4-amine |
| 76 | N-(3-chloro-4-fluorophenyl)-7-{2-[(4-methoxyphenyl)amino]ethyl}-5,6,7,8-tetrahydro[1]benzothieno[2,3-d]pyrimidin-4-amine |
| 77 | 2-{4-[(3-bromophenyl)amino]-5,6,7,8-tetrahydro[1]benzothieno[2,3-d]pyrimidin-7-yl}-N-[2-(methylsulfonyl)ethyl]acetamide |
| 78 | N-(3-bromophenyl)-7-(2-{[2-(4-morpholinyl)ethyl]amino}ethyl)-5,6,7,8-tetrahydro[1]benzothieno[2,3-d]pyrimidin-4-amine |
| 79 | N-(3-bromophenyl)-7-[2-(1-piperidinyl)ethyl]-5,6,7,8-tetrahydro[1]benzothieno[2,3-d]pyrimidin-4-amine |
| 80 | N-(3-bromophenyl)-7-[2-(4-methyl-1-piperazinyl)ethyl]-5,6,7,8-tetrahydro[1]benzothieno[2,3-d]pyrimidin-4-amine |
| 81 | N-(3-bromophenyl)-7-[2-oxo-2-(1-pyrrolidinyl)ethyl]-5,6,7,8-tetrahydro[1]benzothieno[2,3-d]pyrimidin-4-amine |
| 82 | 2-{4-[(3-bromophenyl)amino]-5,6,7,8-tetrahydro[1]benzothieno[2,3-d]pyrimidin-7-yl}-N-(2-methoxyethyl)acetamide |
| 83 | 2-{4-[(3-bromophenyl)amino]-5,6,7,8-tetrahydro[1]benzothieno[2,3-d]pyrimidin-7-yl}-N-(2-methoxyethyl)-N-methylacetamide |
| 84 | N-(3-bromophenyl)-7-(2-{[2-(methylsulfonyl)ethyl]amino}ethyl)-5,6,7,8-tetrahydro[1]benzothieno[2,3-d]pyrimidin-4-amine |
| 85 | N-(3-bromophenyl)-7-[2-(1-pyrrolidinyl)ethyl]-5,6,7,8-tetrahydro[1]benzothieno[2,3-d]pyrimidin-4-amine |
| 86 | N-(3-bromophenyl)-7-{2-[(2-methoxyethyl)amino]ethyl}-5,6,7,8-tetrahydro[1]benzothieno[2,3-d]pyrimidin-4-amine |
| 87 | N-(3-bromophenyl)-7-{2-[(2-methoxyethyl)(methyl)amino]ethyl}-5,6,7,8-tetrahydro[1]benzothieno[2,3-d]pyrimidin-4-amine |
| 88 | N-(3-bromophenyl)-7-[2-(1H-emidazol-1-yl)ethyl]-5,6,7,8-tetrahydro[1]benzothieno[2,3-d]pyrimidin-4-amine |
| 89 | N-(3-bromophenyl)-7-{2-[(4-methoxyphenyl)amino]ethyl}-5,6,7,8-tetrahydro[1]benzothieno[2,3-d]pyrimidin-4-amine |
| 90 | N-(3-bromophenyl)-7-(2-methoxyethyl)-5,6,7,8-tetrahydro[1]benzothieno[2,3-d]pyrimidin-4-amine |
| 91 | N-(3-bromophenyl)-7-{2-[4-(2-methoxyethyl)-1-piperazinyl]-2-oxoethyl}-5,6,7,8-tetrahydro[1]benzothieno[2,3-d]pyrimidin-4-amine |
| 92 | N-(3-bromophenyl)-7-{2-[(3R)-3-(dimethylamino)-1-pyrrolidinyl]-2-oxoethyl}-5,6,7,8-tetrahydro[1]benzothieno[2,3-d]pyrimidin-4-amine |
| 93 | N-(3-bromophenyl)-7-{2-[4-(2-methoxyethyl)-1-piperazinyl]ethyl}-5,6,7,8-tetrahydro[1]benzothieno[2,3-d]pyrimidin-4-amine |
| 94 | N-(3-bromophenyl)-7-{2-[(3R)-3-(dimethylamino)-1-pyrrolidinyl]ethyl}-5,6,7,8-tetrahydro[1]benzothieno[2,3-d]pyrimidin-4-amine |
| 95 | 1-{4-[(3-bromophenyl)amino]-5,6,7,8-tetrahydro[1]benzothieno[2,3-d]pyrimidin-7-yl}-2-methyl-2-propanol |
| 96 | N-(3-chloro-4-fluorophenyl)-7-{2-[(2-methoxyethyl)(methyl)amino]ethyl}-5,6,7,8-tetrahydro[1]benzothieno[2,3-d]pyrimidin-4-amine |
| 97 | N-(3-chloro-4-fluorophenyl)-7-(2-{[(2-methylsulfonyl)ethyl]amino}ethyl)-5,6,7,8-tetrahydro[1]benzothieno[2,3-d]pyrimidin-4-amine |
| 98 | $N^1$-(2-{4-[(3-chloro-4-fluorophenyl)amino]-5,6,7,8-tetrahydro[1]benzothieno[2,3-d]pyrimidin-7-yl}ethyl)-$N^2$,$N^2$-dimethyl-1,2-ethanediamine |
| 99 | N-(3-chloro-4-fluorophenyl)-7-{2-[4-(4-pyridinylmethyl)-1-piperazinyl]ethyl}-5,6,7,8-tetrahydro[1]benzothieno[2,3-d]pyrimidin-4-amine |
| 100 | N-(3-chloro-4-fluorophenyl)-7-{2-[(3R)-3-(dimethylamino)-1-pyrrolidinyl]ethyl}-5,6,7,8-tetrahydro[1]benzothieno[2,3-d]pyrimidin-4-amine |
| 101 | N-(3-chloro-4-fluorophenyl)-7-(2-methoxyethyl)-5,6,7,8-tetrahydro[1]benzothieno[2,3-d]pyrimidin-4-amine |
| 102 | 2-{4-[(3-bromophenyl)amino]-5,6,7,8-tetrahydro[1]benzothieno[2,3-d]pyrimidin-7-yl}ethanol |
| 103 | N-(3-bromophenyl)-7-{2-oxo-2-[4-(4-pyridinylmethyl)-1-piperazinyl]ethyl}-5,6,7,8-tetrahydro[1]benzothieno[2,3-d]pyrimidin-4-amine |
| 104 | N-{7-[2-(4-methyl-1-piperazinyl)-2-oxoethyl]-5,6,7,8-tetrahydro[1]benzothieno[2,3-d]pyrimidin-4-yl}-N-(3,4,5-trimethoxyphenyl)amine |
| 105 | N-(4-bromo-2-fluorophenyl)-7-[2-(4-methyl-1-piperazinyl)-2-oxoethyl]-5,6,7,8-tetrahydro[1]benzothieno[2,3-d]pyrimidin-4-amine |
| 106 | N-(2-{4-[(3-chlorophenyl)amino]-5,6,7,8-tetrahydro[1]benzothieno[2,3-d]pyrimidin-7-yl}ethyl)-2-thiophenesulfonamide |
| 107 | N-({4-[(3-bromophenyl)amino]-5,6,7,8-tetrahydro[1]benzothieno[2,3-d]pyrimidin-7-yl}methyl)-N,N-diethylurea |
| 108 | N-({4-[(3-ethynylphenyl)amino]-5,6,7,8-tetrahydro[1]benzothieno[2,3-d]pyrimidin-7-yl}methyl)-N'-(3-pyridinyl)urea |
| 109 | N-({4-[(3-chloro-4-fluoropheny)amino]-5,6,7,8-tetrahydro[1]benzothieno[2,3-d]pyrimidin-7-yl}methyl)-N'-ethylurea |
| 110 | N-(4-methoxyphenyl)-N'-({4-[(3-methoxyphenyl)amino]-5,6,7,8-tetrahydro[1]benzothieno[2,3-d]pyrimidin-7-yl}methyl)urea |
| 111 | N-(2-{4-[(2,4-dichlorophenyl)amino]-5,6,7,8-tetrahydro[1]benzothieno[2,3-d]pyrimidin-7-yl}ethyl)-1-pyrrolidinecarboxamide |

TABLE 2-continued

| Entry No. | IUPAC Name |
|---|---|
| 112 | N-({4-[(3-phenoxyphenyl)amino]-5,6,7,8-tetrahydro[1]benzothieno[2,3-d]pyrimidin-7-yl}methyl)-4-morpholinecarboxamide |
| 113 | 4-[(3-chloro-4-fluorophenyl)amino]-N-(3-methoxyphenyl)-5,6,7,8-tetrahydro[1]benzothieno[2,3-d]pyrimidine-7-carboxamide |
| 114 | [1-({4-[(3-bromophenyl)amino]-5,6,7,8-tetrahydro[1]benzothieno[2,3-d]pyrimidin-7-yl}carbonyl)-2-pyrrolidinyl]methanol |
| 115 | N-(3-chloro-4-fluorophenyl)-7-[(2,5-dimethyl-1-pyrrolidinyl)carbonyl]-5,6,7,8-tetrahydro[1]benzothieno[2,3-d]pyrimidin-4-amine |
| 116 | N-(3-chlorophenyl)-7-{[2-(methoxymethyl)-1-pyrrolidinyl]carbonyl}-5,6,7,8-tetrahydro[1]benzothieno[2,3-d]pyrimidin-4-amine |
| 117 | 1-({4-[(4-bromo-2-fluorophenyl)amino]-5,6,7,8-tetrahydro[1]benzothieno[2,3-d]pyrimidin-7-yl}acetyl)-3-pyrrolidinol |
| 118 | N-(3-bromophenyl)-7-[2-(3-methyl-1-pyrrolidinyl)-2-oxoethyl]-5,6,7,8-tetrahydro[1]benzothieno[2,3-d]pyrimidin-4-amine |
| 119 | N-(3-ethynylphenyl)-7-(4-thiomorpholinylmethyl)-5,6,7,8-tetrahydro[1]benzothieno[2,3-d]pyrimidin-4-amine |
| 120 | N-(4-bromo-2-fluorophenyl)-7-{[2-(methoxymethyl)-1-pyrrolidinyl]methyl}-5,6,7,8-tetrahydro[1]benzothieno[2,3-d]pyrimidin-4-amine |
| 121 | N-(3-chloro-4-fluorophenyl)-7-{2-[4-(3-methylphenyl)-1-piperazinyl]ethyl}-5,6,7,8-tetrahydro[1]benzothieno[2,3-d]pyrimidin-4-amine |
| 122 | N-(3-chloro-2-fluorophenyl)-7-(2-pyrrolidin-1-ylethyl)-5,6,7,8-tetrahydro[1]benzothieno[2,3-d]pyrimidin-4-amine |
| 123 | N-{7-[2-(2,5-dimethylpyrrolidin-1-yl)ethyl]-5,6,7,8-tetrahydro[1]benzothieno[2,3-d]pyrimidin-4-yl}benzene-1,3-diamine |
| 124 | N-(2-fluorophenyl)-7-(2-oxo-2-pyrrolidin-1-ylethyl)-5,6,7,8-tetrahydro[1]benzothieno[2,3-d]pyrimidin-4-amine |
| 125 | 2-{4-[(3-bromophenyl)amino]-5,6,7,8-tetrahydro[1]benzothieno[2,3-d]pyrimidin-7-yl}-N-[3-(ethylamino)phenyl]acetamide |
| 126 | 7-allyl-N-(3-ethynylphenyl)-7-(pyrrolidin-1-ylmethyl)-5,6,7,8-tetrahydro[1]benzothieno[2,3-d]pyrimidin-4-amine |
| 127 | 7-benzyl-N-(3,4-dichlorophenyl)-7-({[2-(methylsulfonyl)ethyl]amino}methyl)-5,6,7,8-tetrahydro[1]benzothieno[2,3-d]pyrimidin-4-amine |
| 128 | N-(3-chloro-4-fluorophenyl)-7-methyl-7-(2-morpholin-4-ylethyl)-5,6,7,8-tetrahydro[1]benzothieno[2,3-d]pyrimidin-4-amine |
| 129 | ethyl [4-({3-chloro-4-[(3-fluorobenzyl)oxy]phenyl}amino)-5,6,7,8-tetrahydro[1]benzothieno[2,3-d]pyrimidin-7-yl]acetate |
| 130 | 2-[4-({3-chloro-4-[(3-fluorobenzyl)oxy]phenyl}amino)-5,6,7,8-tetrahydro[1]benzothieno[2,3-d]pyrimidin-7-yl]ethanol |
| 131 | 7-(2-bromoethyl)-N-{3-chloro-4-[(3-fluorobenzyl)oxy]phenyl}-5,6,7,8-tetrahydro[1]benzothieno[2,3-d]pyrimidin-4-amine |
| 132 | N-{3-chloro-4-[(3-fluorobenzyl)oxy]phenyl}-7-(2-morpholin-4-ylethyl)-5,6,7,8-tetrahydro[1]benzothieno[2,3-d]pyrimidin-4-amine |
| 133 | N-{3-chloro-4-[(3-fluorobenzyl)oxy]phenyl}-7-{2-[(3S)-3-(dimethylamino)pyrrolidin-1-yl]ethyl}-5,6,7,8-tetrahydro[1]benzothieno[2,3-d]pyrimidin-4-amine |
| 134 | N-[3-chloro-4-(pyridin-2-ylmethoxy)phenyl]-7-{2-[(3S)-3-(dimethylamino)pyrrolidin-1-yl]ethyl}-5,6,7,8-tetrahydro[1]benzothieno[2,3-d]pyrimidin-4-amine |
| 135 | N-{3-chloro-4-[(3-fluorobenzyl)oxy]phenyl}-7-{2-[(2-methoxyethyl)amino]ethyl}-5,6,7,8-tetrahydro[1]benzothieno[2,3-d]pyrimidin-4-amine |
| 136 | ethyl [4-({3-chloro-4-[(4-fluorobenzyl)oxy]phenyl}amino)-5,6,7,8-tetrahydro[1]benzothieno[2,3-d]pyrimidin-7-yl]acetate |
| 137 | N-{3-chloro-4-[(4-fluorobenzyl)oxy]phenyl}-7-(2-morpholin-4-yl-2-oxoethyl)-5,6,7,8-tetrahydro[1]benzothieno[2,3-d]pyrimidin-4-amine |
| 138 | N-{3-chloro-4-[(4-fluorobenzyl)oxy]phenyl}-7-(2-morpholin-4-ylethyl)-5,6,7,8-tetrahydro[1]benzothieno[2,3-d]pyrimidin-4-amine |
| 139 | 2-[4-({3-chloro-4-[(4-fluorobenzyl)oxy]phenyl}amino)-5,6,7,8-tetrahydro[1]benzothieno[2,3-d]pyrimidin-7-yl]-N-(2-methoxyethyl)acetamide |
| 140 | 2-[4-({3-chloro-4-[(4-fluorobenzyl)oxy]phenyl}amino)-5,6,7,8-tetrahydro[1]benzothieno[2,3-d]pyrimidin-7-yl]-N-[2-(methylsulfonyl)ethyl]acetamide |
| 141 | N-{3-chloro-4-[(4-fluorobenzyl)oxy]phenyl}-7-{2-[(3S)-3-(dimethylamino)pyrrolidin-1-yl]-2-oxoethyl}-5,6,7,8-tetrahydro[1]benzothieno[2,3-d]pyrimidin-4-amine |
| 142 | N-{3-chloro-4-[(4-fluorobenzyl)oxy]phenyl}-7-(2-oxo-2-pyrrolidin-1-ylethyl)-5,6,7,8-tetrahydro[1]benzothieno[2,3-d]pyrimidin-4-amine |
| 143 | N-{3-chloro-4-[(4-fluorobenzyl)oxy]phenyl}-7-[2-(4-methylpiperazin-1-yl)-2-oxoethyl]-5,6,7,8-tetrahydro[1]benzothieno[2,3-d]pyrimidin-4-amine |
| 144 | 2-[4-({3-chloro-4-[(4-fluorobenzyl)oxy]phenyl}amino)-5,6,7,8-tetrahydro[1]benzothieno[2,3-d]pyrimidin-7-yl]-N-(2-methoxyethyl)-N-methylacetamide |
| 145 | N-{3-chloro-4-[(4-fluorobenzyl)oxy]phenyl}-7-{2-[(2-methoxyethyl)(methyl)amino]ethyl}-5,6,7,8-tetrahydro[1]benzothieno[2,3-d]pyrimidin-4-amine |

TABLE 2-continued

| Entry No. | IUPAC Name |
|---|---|
| 146 | N-{3-chloro-4-[(4-fluorobenzyl)oxy]phenyl}-7-(2-pyrrolidin-1-ylethyl)-5,6,7,8-tetrahydro[1]benzothieno[2,3-d]pyrimidin-4-amine |
| 147 | N-{3-chloro-4-[(4-fluorobenzyl)oxy]phenyl}-7-[2-(4-methylpiperazin-1-yl)ethyl]-5,6,7,8-tetrahydro[1]benzothieno[2,3-d]pyrimidin-4-amine |
| 148 | 2-[4-({3-chloro-4-[(4-fluorobenzyl)oxy]phenyl}amino)-5,6,7,8-tetrahydro[1]benzothieno[2,3-d]pyrimidin-7-yl]ethanol |
| 149 | 2-[4-({3-chloro-4-[(4-fluorobenzyl)oxy]phenyl}amino)-5,6,7,8-tetrahydro[1]benzothieno[2,3-d]pyrimidin-7-yl]ethyl methanesulfonate |
| 150 | N-{3-chloro-4-[(4-fluorobenzyl)oxy]phenyl}-7-{2-[(3S)-3-(dimethylamino)pyrrolidin-1-yl]ethyl}-5,6,7,8-tetrahydro[1]benzothieno[2,3-d]pyrimidin-4-amine |
| 151 | N-{3-chloro-4-[(3-fluorobenzyl)oxy]phenyl}-7-[2-(4-methylpiperazin-1-yl)ethyl]-5,6,7,8-tetrahydro[1]benzothieno[2,3-d]pyrimidin-4-amine |
| 152 | N-{3-chloro-4-[(3-fluorobenzyl)oxy]phenyl}-7-{2-[(2-methoxyethyl)(methyl)amino]ethyl}-5,6,7,8-tetrahydro[1]benzothieno[2,3-d]pyrimidin-4-amine |
| 153 | N-{3-chloro-4-[(3-fluorobenzyl)oxy]phenyl}-7-{2-[(3R)-3-(dimethylamino)pyrrolidin-1-yl]ethyl}-5,6,7,8-tetrahydro[1]benzothieno[2,3-d]pyrimidin-4-amine |
| 154 | N-{3-chloro-4-[(3-fluorobenzyl)oxy]phenyl}-7-(2-pyrrolidin-1-ylethyl)-5,6,7,8-tetrahydro[1]benzothieno[2,3-d]pyrimidin-4-amine |
| 155 | N'-{2-[4-({3-chloro-4-[(3-fluorobenzyl)oxy]phenyl}amino)-5,6,7,8-tetrahydro[1]benzothieno[2,3-d]pyrimidin-7-yl]ethyl}-N,N-dimethylethane-1,2-diamine |
| 156 | 2-({2-[4-({3-chloro-4-[(3-fluorobenzyl)oxy]phenyl}amino)-5,6,7,8-tetrahydro[1]benzothieno[2,3-d]pyrimidin-7-yl]ethyl}amino)ethanol |
| 157 | N-{3-chloro-4-[(3-fluorobenzyl)oxy]phenyl}-7-[2-(dimethylamino)ethyl]-5,6,7,8-tetrahydro[1]benzothieno[2,3-d]pyrimidin-4-amine |
| 158 | 2,2'-({2-[4-({3-chloro-4-[(3-fluorobenzyl)oxy]phenyl}amino)-5,6,7,8-tetrahydro[1]benzothieno[2,3-d]pyrimidin-7-yl]ethyl}imino)diethanol |
| 159 | N-{3-chloro-4-[(3-fluorobenzyl)oxy]phenyl}-7-{2-[(2-morpholin-4-ylethyl)amino]ethyl}-5,6,7,8-tetrahydro[1]benzothieno[2,3-d]pyrimidin-4-amine |
| 160 | N-{3-chloro-4-[(3-fluorobenzyl)oxy]phenyl}-7-(2-piperidin-1-ylethyl)-5,6,7,8-tetrahydro[1]benzothieno[2,3-d]pyrimidin-4-amine |
| 161 | N-{3-chloro-4-[(3-fluorobenzyl)oxy]phenyl}-7-{2-[4-(2-methoxyethyl)piperazin-1-yl]ethyl}-5,6,7,8-tetrahydro[1]benzothieno[2,3-d]pyrimidin-4-amine |
| 162 | N-{3-chloro-4-[(3-fluorobenzyl)oxy]phenyl}-7-[2-(methylamino)ethyl]-5,6,7,8-tetrahydro[1]benzothieno[2,3-d]pyrimidin-4-amine |
| 163 | N-{3-chloro-4-[(3-fluorobenzyl)oxy]phenyl}-7-[2-(1H-imidazol-1-yl)ethyl]-5,6,7,8-tetrahydro[1]benzothieno[2,3-d]pyrimidin-4-amine |
| 164 | N-{3-chloro-4-[(3-fluorobenzyl)oxy]phenyl}-7-{2-[4-(pyridin-4-ylmethyl)piperazin-1-yl]ethyl}-5,6,7,8-tetrahydro[1]benzothieno[2,3-d]pyrimidin-4-amine |
| 165 | 4-(4-{2-[4-({3-chloro-4-[(3-fluorobenzyl)oxy]phenyl}amino)-5,6,7,8-tetrahydro[1]benzothieno[2,3-d]pyrimidin-7-yl]ethyl}piperazin-1-yl)benzonitrile |
| 166 | ethyl (4-{[3-chloro-4-(pyridin-2-ylmethoxy)phenyl]amino}-5,6,7,8-tetrahydro[1]benzothieno[2,3-d]pyrimidin-7-yl)acetate |
| 167 | 2-(4-{[3-chloro-4-(pyridin-2-ylmethoxy)phenyl]amino}-5,6,7,8-tetrahydro[1]benzothieno[2,3-d]pyrimidin-7-yl)ethanol |
| 168 | 2-(4-{[3-chloro-4-(pyridin-2-ylmethoxy)phenyl]amino}-5,6,7,8-tetrahydro[1]benzothieno[2,3-d]pyrimidin-7-yl)ethyl methanesulfonate |
| 169 | N-[3-chloro-4-(pyridin-2-ylmethoxy)phenyl]-7-{2-[(2-methoxyethyl)amino]ethyl}-5,6,7,8-tetrahydro[1]benzothieno[2,3-d]pyrimidin-4-amine |
| 170 | N-[3-chloro-4-(pyridin-2-ylmethoxy)phenyl]-7-(2-morpholin-4-ylethyl)-5,6,7,8-tetrahydro[1]benzothieno[2,3-d]pyrimidin-4-amine |
| 171 | N-[3-chloro-4-(pyridin-2-ylmethoxy)phenyl]-7-(2-{[2-(methylsulfonyl)ethyl]amino}ethyl)-5,6,7,8-tetrahydro[1]benzothieno[2,3-d]pyrimidin-4-amine |
| 172 | 2,2'-{[2-(4-{[3-chloro-4-(pyridin-2-ylmethoxy)phenyl]amino}-5,6,7,8-tetrahydro[1]benzothieno[2,3-d]pyrimidin-7-yl)ethyl]imino}diethanol |
| 173 | 2-{[2-(4-{[3-chloro-4-(pyridin-2-ylmethoxy)phenyl]amino}-5,6,7,8-tetrahydro[1]benzothieno[2,3-d]pyrimidin-7-yl)ethyl]amino}ethanol |
| 174 | N-[3-chloro-4-(pyridin-2-ylmethoxy)phenyl]-7-{2-[(3R)-3-(dimethylamino)pyrrolidin-1-yl]ethyl}-5,6,7,8-tetrahydro[1]benzothieno[2,3-d]pyrimidin-4-amine |
| 175 | N-[3-chloro-4-(pyridin-2-ylmethoxy)phenyl]-7-[2-(1H-imidazol-1-yl)ethyl]-5,6,7,8-tetrahydro[1]benzothieno[2,3-d]pyrimidin-4-amine |
| 176 | N-[3-chloro-4-(pyridin-2-ylmethoxy)phenyl]-7-[2-(4-methylpiperazin-1-yl)ethyl]-5,6,7,8-tetrahydro[1]benzothieno[2,3-d]pyrimidin-4-amine |
| 177 | N'-[2-(4-{[3-chloro-4-(pyridin-2-ylmethoxy)phenyl]amino}-5,6,7,8-tetrahydro[1]benzothieno[2,3-d]pyrimidin-7-yl)ethyl]-N,N-dimethylethane-1,2-diamine |

TABLE 2-continued

| Entry No. | IUPAC Name |
|---|---|
| 178 | N-[3-chloro-4-(pyridin-2-ylmethoxy)phenyl]-7-[2-(dimethylamino)ethyl]-5,6,7,8-tetrahydro[1]benzothieno[2,3-d]pyrimidin-4-amine |
| 179 | (3S)-1-{2-[4-({3-chloro-4-[(3-fluorobenzyl)oxy]phenyl}amino)-5,6,7,8-tetrahydro[1]benzothieno[2,3-d]pyrimidin-7-yl]ethyl}pyrrolidin-3-ol |
| 180 | N-[3-chloro-4-(pyridin-2-ylmethoxy)phenyl]-7-[2-(methylamino)ethyl]-5,6,7,8-tetrahydro[1]benzothieno[2,3-d]pyrimidin-4-amine |
| 181 | N-[3-chloro-4-(pyridin-2-ylmethoxy)phenyl]-7-{2-[4-(2-methoxyethyl)piperazin-1-yl]ethyl}-5,6,7,8-tetrahydro[1]benzothieno[2,3-d]pyrimidin-4-amine |
| 182 | N-[3-chloro-4-(pyridin-2-ylmethoxy)phenyl]-7-{2-[(2-methoxyethyl)(methyl)amino]ethyl}-5,6,7,8-tetrahydro[1]benzothieno[2,3-d]pyrimidin-4-amine |
| 183 | N-[3-chloro-4-(pyridin-2-ylmethoxy)phenyl]-7-(2-pyrrolidin-1-ylethyl)-5,6,7,8-tetrahydro[1]benzothieno[2,3-d]pyrimidin-4-amine |
| 184 | N-[3-chloro-4-(pyridin-2-ylmethoxy)phenyl]-7-(2-piperidin-1-ylethyl)-5,6,7,8-tetrahydro[1]benzothieno[2,3-d]pyrimidin-4-amine |
| 185 | N-[3-chloro-4-(pyridin-2-ylmethoxy)phenyl]-7-{2-[(2-morpholin-4-ylethyl)amino]ethyl}-5,6,7,8-tetrahydro[1]benzothieno[2,3-d]pyrimidin-4-amine |
| 186 | N-[3-chloro-4-(pyridin-2-ylmethoxy)phenyl]-7-[2-(ethylamino)ethyl]-5,6,7,8-tetrahydro[1]benzothieno[2,3-d]pyrimidin-4-amine |
| 187 | N-[3-chloro-4-(pyridin-2-ylmethoxy)phenyl]-7-[2-(diethylamino)ethyl]-5,6,7,8-tetrahydro[1]benzothieno[2,3-d]pyrimidin-4-amine |
| 188 | N-[3-chloro-4-(pyridin-2-ylmethoxy)phenyl]-7-{2-[(3-methoxypropyl)amino]ethyl}-5,6,7,8-tetrahydro[1]benzothieno[2,3-d]pyrimidin-4-amine |
| 189 | N-[3-chloro-4-(pyridin-2-ylmethoxy)phenyl]-7-{2-[4-(pyridin-4-ylmethyl)piperazin-1-yl]ethyl}-5,6,7,8-tetrahydro[1]benzothieno[2,3-d]pyrimidin-4-amine |
| 190 | (3R)-1-{2-[4-({3-chloro-4-[(3-fluorobenzyl)oxy]phenyl}amino)-5,6,7,8-tetrahydro[1]benzothieno[2,3-d]pyrimidin-7-yl]ethyl}pyrrolidin-3-ol |
| 191 | N-{3-chloro-4-[(3-fluorobenzyl)oxy]phenyl}-7-{2-[(2R)-2-(methoxymethyl)pyrrolidin-1-yl]ethyl}-5,6,7,8-tetrahydro[1]benzothieno[2,3-d]pyrimidin-4-amine |
| 192 | N-{3-chloro-4-[(3-fluorobenzyl)oxy]phenyl}-7-(2-thiomorpholin-4-ylethyl)-5,6,7,8-tetrahydro[1]benzothieno[2,3-d]pyrimidin-4-amine |
| 193 | N-{3-chloro-4-[(3-fluorobenzyl)oxy]phenyl}-7-(2-{[2-(methylsulfonyl)ethyl]amino}ethyl)-5,6,7,8-tetrahydro[1]benzothieno[2,3-d]pyrimidin-4-amine |
| 194 | 4-[(3-chloro-4-fluorophenyl)amino]-7-vinyl-5,6,7,8-tetrahydro[1]benzothieno[2,3-d]pyrimidin-7-ol |
| 195 | 2-{4-[(1-benzyl-1H-indazol-5-yl)amino]-5,6,7,8-tetrahydro[1]benzothieno[2,3-d]pyrimidin-7-yl}ethyl methanesulfonate |
| 196 | 2-{4-[(1-benzyl-1H-indazol-5-yl)amino]-5,6,7,8-tetrahydro[1]benzothieno[2,3-d]pyrimidin-7-yl}ethanol |
| 197 | ethyl {4-[(1-benzyl-1H-indazol-5-yl)amino]-5,6,7,8-tetrahydro[1]benzothieno[2,3-d]pyrimidin-7-yl}acetate |
| 198 | N-(1-benzyl-1H-indazol-5-yl)-7-{2-[(2-methoxyethyl)amino]ethyl}-5,6,7,8-tetrahydro[1]benzothieno[2,3-d]pyrimidin-4-amine |
| 199 | 2-[(2-{4-[(1-benzyl-1H-indazol-5-yl)amino]-5,6,7,8-tetrahydro[1]benzothieno[2,3-d]pyrimidin-7-yl}ethyl)amino]ethanol |
| 200 | N-(1-benzyl-1H-indazol-5-yl)-7-{2-[3-(dimethylamino)pyrrolidin-1-yl]ethyl}-5,6,7,8-tetrahydro[1]benzothieno[2,3-d]pyrimidin-4-amine |
| 201 | N-(1-benzyl-1H-indazol-5-yl)-7-(2-pyrrolidin-1-ylethyl)-5,6,7,8-tetrahydro[1]benzothieno[2,3-d]pyrimidin-4-amine |
| 202 | N-(1-benzyl-1H-indazol-5-yl)-7-{2-[(2-morpholin-4-ylethyl)amino]ethyl}-5,6,7,8-tetrahydro[1]benzothieno[2,3-d]pyrimidin-4-amine |
| 203 | N-(1-benzyl-1H-indazol-5-yl)-7-(2-{[2-(methylsulfonyl)ethyl]amino}ethyl)-5,6,7,8-tetrahydro[1]benzothieno[2,3-d]pyrimidin-4-amine |
| 204 | N-(1-benzyl-1H-indazol-5-yl)-7-{2-[(2-pyrrolidin-1-ylethyl)amino]ethyl}-5,6,7,8-tetrahydro[1]benzothieno[2,3-d]pyrimidin-4-amine |
| 205 | N'-(2-{4-[(1-benzyl-1H-indazol-5-yl)amino]-5,6,7,8-tetrahydro[1]benzothieno[2,3-d]pyrimidin-7-yl}ethyl)-N,N-dimethylbutane-1,4-diamine |
| 206 | ethyl [4-({3-methyl-4-[(6-methylpyridin-3-yl)oxy]phenyl}amino)-5,6,7,8-tetrahydro[1]benzothieno[2,3-d]pyrimidin-7-yl]acetate |
| 207 | 2-[4-({3-methyl-4-[(6-methylpyridin-3-yl)oxy]phenyl}amino)-5,6,7,8-tetrahydro[1]benzothieno[2,3-d]pyrimidin-7-yl]ethanol |
| 208 | 2-[4-({3-methyl-4-[(6-methylpyridin-3-yl)oxy]phenyl}amino)-5,6,7,8-tetrahydro[1]benzothieno[2,3-d]pyrimidin-7-yl]ethyl methanesulfonate |
| 209 | 7-{2-[(2-methoxyethyl)amino]ethyl}-N-{3-methyl-4-[(6-methylpyridin-3-yl)oxy]phenyl}-5,6,7,8-tetrahydro[1]benzothieno[2,3-d]pyrimidin-4-amine |
| 210 | 2-({2-[4-({3-methyl-4-[(6-methylpyridin-3-yl)oxy]phenyl}amino)-5,6,7,8-tetrahydro[1]benzothieno[2,3-d]pyrimidin-7-yl]ethyl}amino)ethanol |
| 211 | 7-{2-[(2-methoxyethyl)(methyl)amino]ethyl}-N-{3-methyl-4-[(6-methylpyridin-3-yl)oxy]phenyl}-5,6,7,8-tetrahydro[1]benzothieno[2,3-d]pyrimidin-4-amine |

TABLE 2-continued

| Entry No. | IUPAC Name |
|---|---|
| 212 | N-{3-methyl-4-[(6-methylpyridin-3-yl)oxy]phenyl}-7-(2-{[2-(methylsulfonyl)ethyl]amino}ethyl)-5,6,7,8-tetrahydro[1]benzothieno[2,3-d]pyrimidin-4-amine |
| 213 | N-{3-methyl-4-[(6-methylpyridin-3-yl)oxy]phenyl}-7-{2-[(2-morpholin-4-ylethyl)amino]ethyl}-5,6,7,8-tetrahydro[1]benzothieno[2,3-d]pyrimidin-4-amine |
| 214 | N-{3-methyl-4-[(6-methylpyridin-3-yl)oxy]phenyl}-7-(2-pyrrolidin-1-ylethyl)-5,6,7,8-tetrahydro[1]benzothieno[2,3-d]pyrimidin-4-amine |
| 215 | 2-(methyl{2-(4-({3-methyl-4-[(6-methylpyridin-3-yl)oxy]phenyl}amino)-5,6,7,8-tetrahydro[1]benzothieno[2,3-d]pyrimidin-7-yl]ethyl}amino)ethanol |
| 216 | 7-{2-[3-(dimethylamino)pyrrolidin-1-yl]ethyl}-N-{3-methyl-4-[(6-methylpyridin-3-yl)oxy]phenyl}-5,6,7,8-tetrahydro[1]benzothieno[2,3-d]pyrimidin-4-amine |
| 217 | N-{3-methyl-4-[(6-methylpyridin-3-yl)oxy]phenyl}-7-[2-(4-methylpiperazin-1-yl)ethyl]-5,6,7,8-tetrahydro[1]benzothieno[2,3-d]pyrimidin-4-amine |
| 218 | N-{3-methyl-4-[(6-methylpyridin-3-yl)oxy]phenyl}-7-(2-morpholin-4-ylethyl)-5,6,7,8-tetrahydro[1]benzothieno[2,3-d]pyrimidin-4-amine |
| 219 | 7-[2-dimethylamino)ethyl]-N-{3-methyl-4-[(6-methylpyridin-3-yl)oxy]phenyl}-5,6,7,8-tetrahydro[1]benzothieno[2,3-d]pyrimidin-4-amine |
| 220 | N-(1-benzyl-1H-indazol-5-yl)-7-[2-(4-methylpiperazin-1-yl)ethyl]-5,6,7,8-tetrahydro[1]benzothieno[2,3-d]pyrimidin-4-amine |
| 221 | N-(1-benzyl-1H-indazol-5-yl)-7-[2-(dimethylamino)ethyl]-5,6,7,8-tetrahydro[1]benzothieno[2,3-d]pyrimidin-4-amine |
| 222 | N-(1-benzyl-1H-indazol-5-yl)-7-[2-(methylamino)ethyl]-5,6,7,8-tetrahydro[1]benzothieno[2,3-d]pyrimidin-4-amine |
| 223 | N,N-dimethyl-N'-{2-[4-({3-methyl-4-[(6-methylpyridin-3-yl)oxy]phenyl}amino)-5,6,7,8-tetrahydro[1]benzothieno[2,3-d]pyrimidin-7-yl]ethyl}ethane-1,2-diamine |
| 224 | 2,2'-({2-[4-({3-methyl-4-[(6-methylpyridin-3-yl)oxy]phenyl}amino)-5,6,7,8-tetrahydro[1]benzothieno[2,3-d]pyrimidin-7-yl]ethyl}imino)diethanol |
| 225 | 7-[2-(methylamino)ethyl]-N-{3-methyl-4-[(6-methylpyridin-3-yl)oxy]phenyl}-5,6,7,8-tetrahydro[1]benzothieno[2,3-d]pyrimidin-4-amine |
| 226 | 1-{2-[4-({3-methyl-4-[(6-methylpyridin-3-yl)oxy]phenyl}amino)-5,6,7,8-tetrahydro[1]benzothieno[2,3-d]pyrimidin-7-yl]ethyl}pyrrolidin-3-ol |
| 227 | N-{3-methyl-4-[(6-methylpyridin-3-yl)oxy]phenyl}-7-[2-(2-methylpyrrolidin-1-yl)ethyl]-5,6,7,8-tetrahydro[1]benzothieno[2,3-d]pyrimidin-4-amine |
| 228 | 7-[2-(2,5-dimethylpyrrolidin-1-yl)ethyl]-N-{3-methyl-4-[(6-methylpyridin-3-yl)oxy]phenyl}-5,6,7,8-tetrahydro[1]benzothieno[2,3-d]pyrimidin-4-amine |
| 229 | N-{3-methyl-4-[(6-methylpyridin-3-yl)oxy]phenyl}-7-(2-piperidin-1-ylethyl)-5,6,7,8-tetrahydro[1]benzothieno[2,3-d]pyrimidin-4-amine |
| 230 | 1-(2-{4-[(1-benzyl-1H-indazol-5-yl)amino]-5,6,7,8-tetrahydro[1]benzothieno[2,3-d]pyrimidin-7-yl}ethyl)pyrrolidin-3-ol |
| 231 | N-(1-benzyl-1H-indazol-5-yl)-7-[2-(2-methylpyrrolidin-1-yl)ethyl]-5,6,7,8-tetrahydro[1]benzothieno[2,3-d]pyrimidin-4-amine |
| 232 | N-(1-benzyl-1H-indazol-5-yl)-7-(2-piperidin-1-ylethyl)-5,6,7,8-tetrahydro[1]benzothieno[2,3-d]pyrimidin-4-amine |
| 233 | N-(3-chloro-4-fluorophenyl)-N-7-[2-(dimethylamino)ethyl]-5,6,7,8-tetrahydro[1]benzothieno[2,3-d]pyrimidine-4,7-diamine |
| 234 | N-(3-chloro-4-fluorophenyl)-7-morpholin-4-yl-5,6,7,8-tetrahydro[1]benzothieno[2,3-d]pyrimidin-4-amine |
| 235 | N-(3-chloro-4-fluorophenyl)-N-7-(2-morpholin-4-ylethyl)-5,6,7,8-tetrahydro[1]benzothieno[2,3-d]pyrimidine-4,7-diamine |
| 236 | N-(3-chloro-4-fluorophenyl)-7-(4-methylpiperazin-1-yl)-5,6,7,8-tetrahydro[1]benzothieno[2,3-d]pyrimidin-4-amine |

Asymmetry, i.e., where a compound's mirror image cannot be super-imposed on the compound, may be present in a compound of Formula I due to the inherent structure of the molecule. Examples of such asymmetric molecules include certain allenes. The compounds of this invention may also contain one or more asymmetric centers, depending upon the location and nature of the various substituents selected. A molecule with a single asymmetric center may be a mixture of enantiomers (R,S), or may be a single (R) or (S) enantiomer. A molecule with more than one asymmetric center may be a mixture of diastereomers, or may be a single diastereomer. Additionally, a compound may exhibit asymmetry due to restricted rotation about a given bond, for example, the central bond adjoining two substituted aromatic rings of the specified compounds. It is intended that all such configurations and conformations (including enantiomers, diastereomers, and other optical isomers) are included within the scope of the present invention. Separated, pure or partially purified stereoisomers of the compounds of Formula I are each included within the scope of the present invention. Preferred compounds are those with the absolute configuration or conformation which produces the more desirable biological activity.

Pharmaceutically acceptable salts of the compounds of this invention are also within the scope of this invention. The term "pharmaceutically acceptable salt" refers to an inorganic or organic salt of a compound of the present invention that has properties acceptable for therapeutic use. For example, see S. M. Berge, et al. "Pharmaceutical Salts," *J. Pharm. Sci.* 1977, 66, 1–19.

Representative salts of the compounds of this invention include the conventional non-toxic salts and the quaternary ammonium salts that are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, sulfate, and undecanoate. The term acid addition salts also comprises the hydrates and the solvent addition forms which the compounds of this invention are able to form. Examples of such forms are, for example, hydrates, alcoholates and the like.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates including dimethyl, diethyl, and dibutyl sulfate; and diamyl sulfates, long chain halides such as decyl, lauryl, myristyl and strearyl chlorides, bromides and iodides, aralkyl halides including benzyl and phenethyl bromides, and others.

The esters of appropriate compounds of this invention are pharmaceutically acceptable esters such as $(C_1-C_6)$alkyl esters, including methyl, ethyl, propyl, isopropyl, butyl, isobutyl or pentyl esters, and the like. Additional esters such as $(C_1-C_6)$alkyl-phenyl may be used, although methyl ester is preferred.

Unless the context clearly indicates to the contrary, whenever the term "compounds of this invention," "a compound of the present invention", and the like, are used herein, they are intended to include the chemically feasible pharmaceutically acceptable salts and/or esters as well as all stereoisomeric forms of the referenced compounds.

Method of Making the Compounds of the Present Invention

In general, the compounds used in this invention may be prepared by standard techniques known in the art, by known processes analogous thereto, and/or by the processes described herein, using starting materials which are either commercially available or producible according to routine, conventional chemical methods.

Generic Schemes

The following Reaction Schemes 1–4 illustrate a preferred synthetic route for synthesizing the compounds of Formula I.

Reaction Scheme 1 depicts the synthesis of the compounds of Formula I.

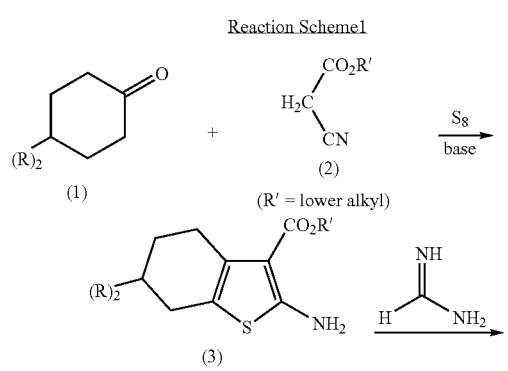

Reaction Scheme 1

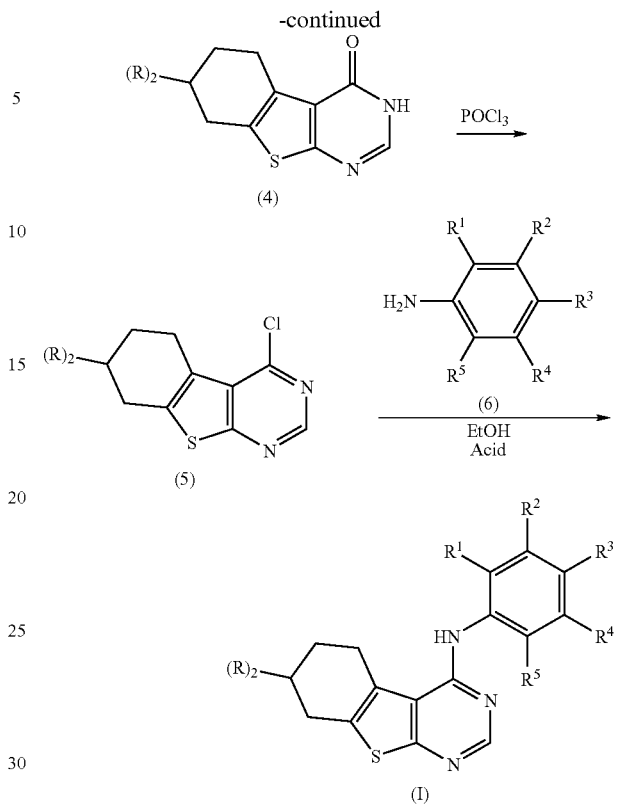

The cyclohexanone (1) of Reaction Scheme I, where each R of $(R)_2$ may be the same or may be different, (that is, one R may be H and the other R is other than H, or both R's may be other than H where each R is the same or different), is commercially available or may be prepared according to one of the following schemes: Jaen et al, *Bio. Org. Med. Chem. Lett.*, 1993, 3 (4), 639–644, *Tetrahedron* 1997, 53 (13), 4693–4702.; *Tetrahedron: Asym.* 1994, 5 (3), 339–342.; *Tetrahedron: Asym.* 1995, 6 (11), 2647–2650.; *Aust. J. Chem.* 1994, 47(10), 1833–1842.; *Tetrahedron* 1999, 55, 11095–11108.), each of which is incorporated herein by reference. Cyclohexanone (1) is coupled with an appropriate cyanoacetic ester (2) in the presence of elemental sulfur and a base such as morpholine, preferably at room temperature, to yield the aminothiophene ester of formula (3) according to the procedure of Gewald, *J. Heterocyclic Chem.*, 1999, 36, 333–345, which is incorporated herein by reference. The aminothiophene ester (3) is then converted to a compound of formula (4) by reaction with a formamide-containing reagent such as neat formamide, or formamidine acetate, in a polar solvent such as DMF, with heat, preferably to 100° C. or above. Heating the compound of formula (4) with a reagent such as phosphorous oxychloride provides compound (5). Finally, compound (5) may be reacted with a variety of substituted anilines (6), each of which is readily available or can be synthesized by means well known in the art, in the presence of a catalytic amount of concentrated acid, such as HCl, and a protic solvent, such as ethanol, to yield a compound of Formula I.

Reaction Scheme 2 outlines the synthesis of certain compounds of Formula I where one R is H (not shown) and the other R is $(C_1-C_6)$alkyl substituted with OH or halo, or with $C(O)R^6$ where $R^6$ is $NR^8R^8$.

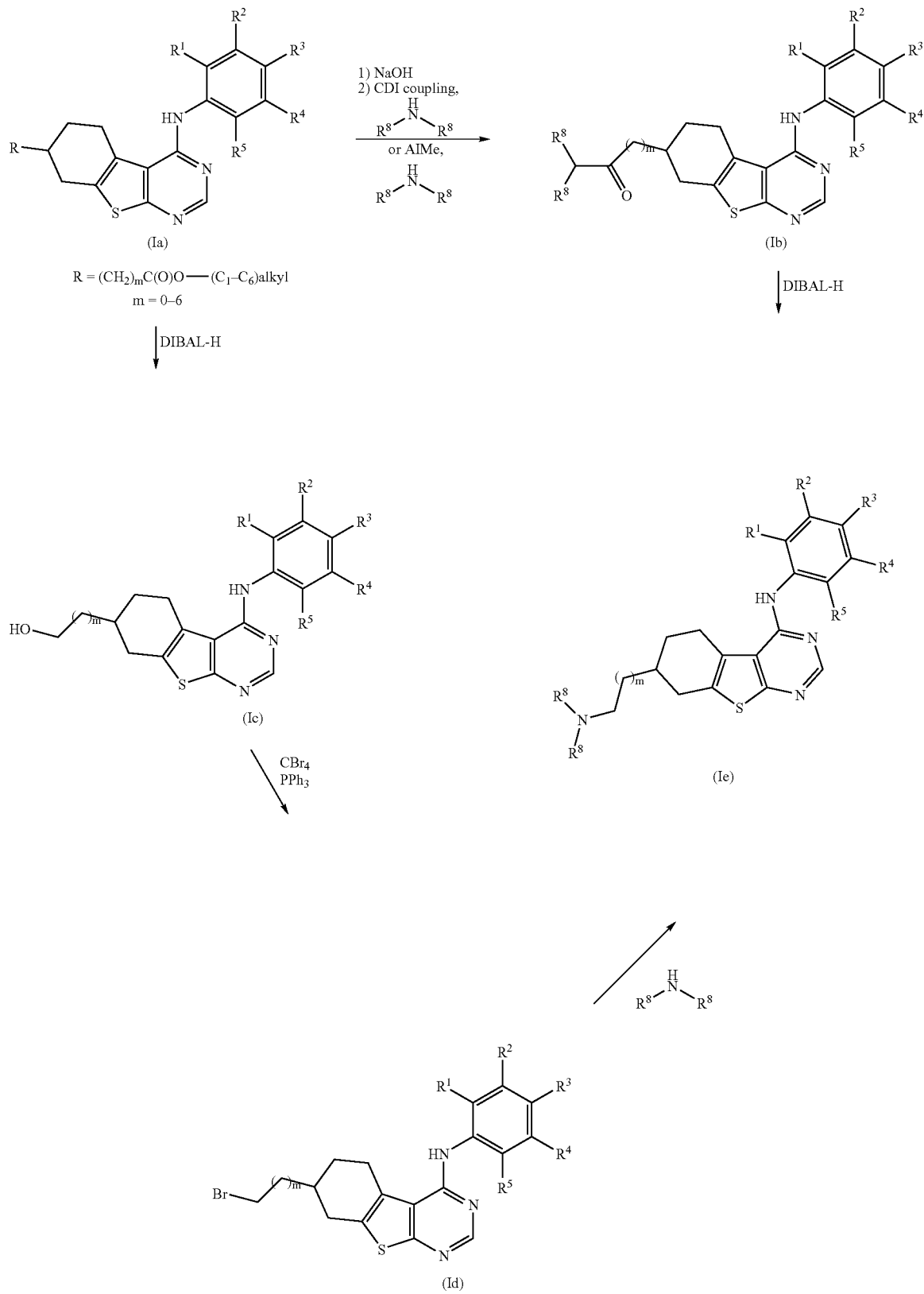

The starting material (Ia), where one R is H (not shown) and the other R is (CH$_2$)$_m$C(O)O(C$_1$–C$_3$)alkoxy, and m is 0, 1, 2, 3, 4, 5 or 6 may be made according to Reaction Scheme 1. Compound (Ia) is either saponified to its corresponding carboxylic acid under basic conditions (such as 1N NaOH in an appropriate solvent) and subsequently coupled with 1,1'-carbonyldiimidazole and an amine (HNR$^8$R$^8$) to yield the amide (Ib), or alternatively, (Ia) is converted to the amide (Ib) by a Weinreb (*Tetrahedron Lett.* 1981, 22 (39), 3815–3818) amidation with a reagent such as trimethyl aluminum and a nucleophilic amine such as piperidine (as shown in Example 3). If desired, (Ib) is reduced to its corresponding amine (Ie) in one step via a reducing reagent such as DIBAL-H in a protic solvent such as THF. Compound (Ia) may also be reduced to its corresponding alcohol (Ic) with a reducing agent such as DIBAL-H in a protic solvent such as THF. The alcohol (Ic) may be further transformed into the bromoalkyl (Id) by bromination with a reagent such as CBr$_4$ in the presence of PPh$_3$. Reaction of the bromoalkyl (Id) with an amine (NHR$^8$R$^8$) such as piperidine (such as in Example 4) also yields compounds of formula (Ie).

Reaction Scheme 3 outlines the synthesis of the compounds of Formula I where one R is H (not shown) and the other R is (C$_1$–C$_6$)alkyl R$^7$ and R$^7$ is NH S(O)$_2$R$^9$ (If), or NH(C(O)NR$^8$R$^8$ (Ig).

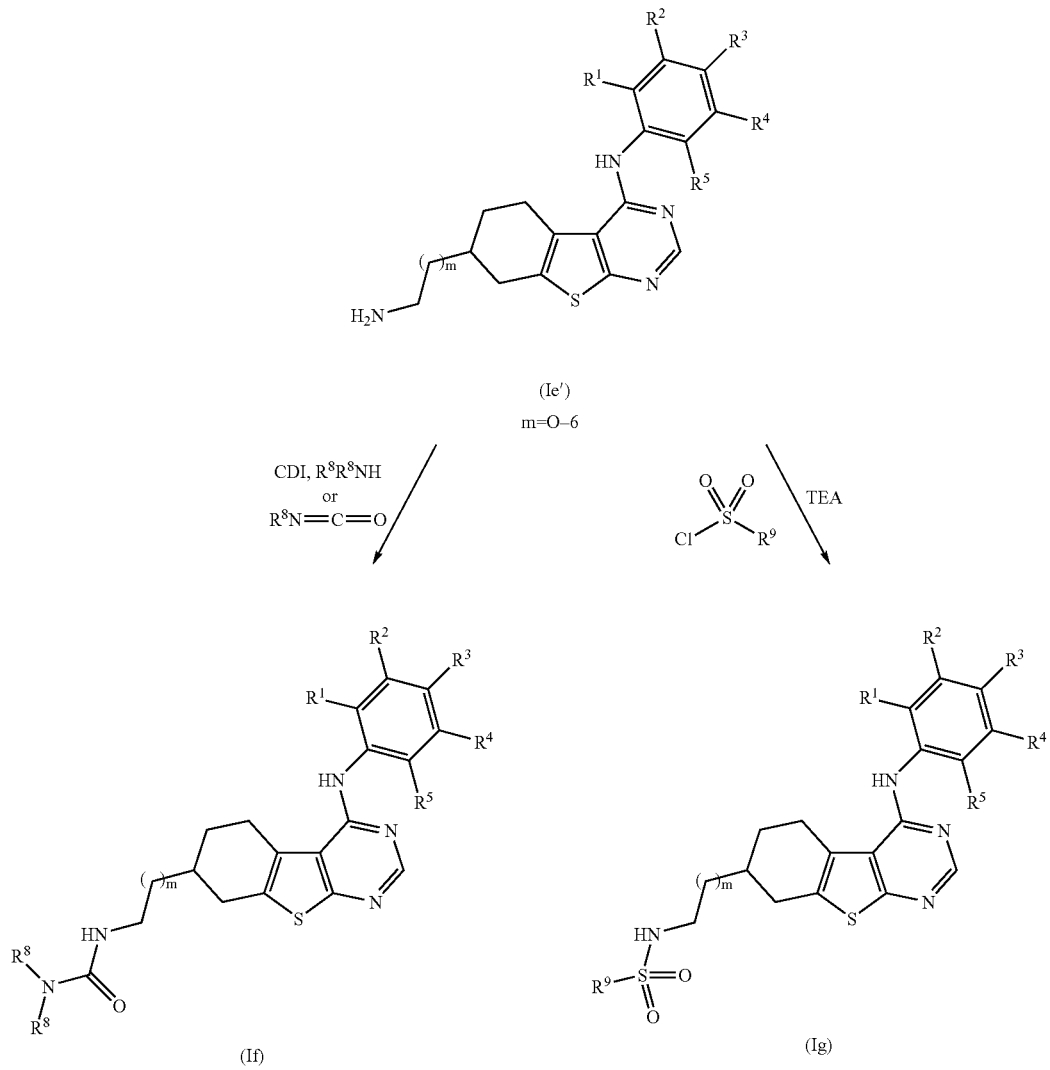

Compound (Ie') (where R$^8$ of (Ie)'s NR$^8$R$^8$ group is H in both instances) of Reaction Scheme 2 is reacted with an amine HNR$^8$R$^8$ in the presence of a coupling reagent such as 1,1'-carbonyldiimidazole, or (Ie) is reacted with an isocyanate R$^8$N=C=O. Compounds of formula (Ie) can also be reacted with sulfonyl chlorides and a mild base such as TEA in a solvent such as CH$_2$Cl$_2$ to yield the compounds of Formula (Ig).

Reaction Scheme 4 outlines the synthesis of the compounds of Formula (Ih), and of Formula (Ii) where one R is H (not shown) and the other R is (CH$_2$)$_m$C(O)R$^6$, m is 0, 1, 2, 3, 4, 5 or 6, and R$^6$ is (C$_1$–C$_6$)alkyl, pyridyl or phenyl.

Reaction Scheme 4

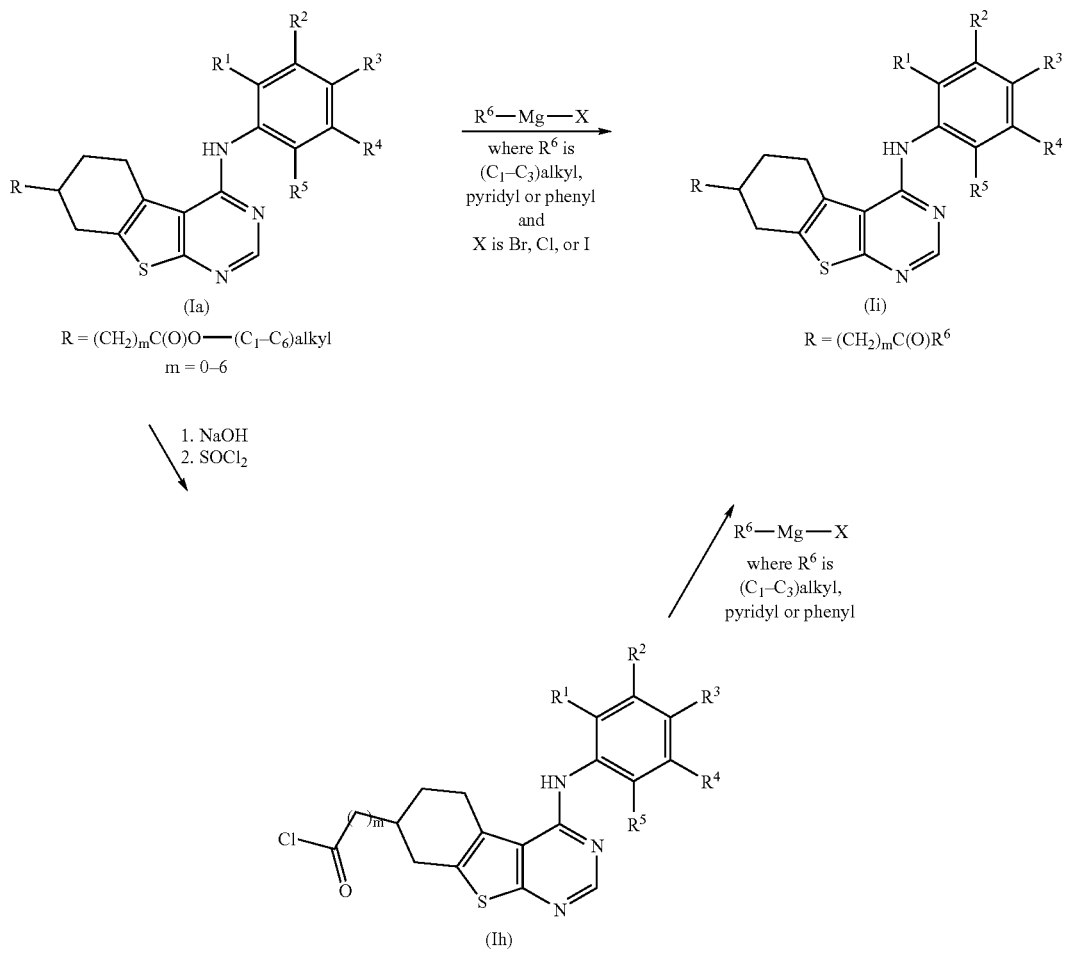

In one pathway of Reaction Scheme 4, the compound of formula (Ia), as previously described above in Reaction Scheme 2, is reacted in an inert solvent such as THF, with an alkyl or aryl Grignard reagent of formula $R^6MgX$, where $R^6$ is a $(C_1-C_6)$alkyl, phenyl or pyridyl group and X is Br, Cl, or I, to provide a ketone of formula (Ii). In the alternative pathway, the formula (Ia) compound is first saponified to the corresponding carboxylic acid, the convert to an acid chloride of formula (Ih), which is then subjected to the same Grignard reaction conditions to provide compound (Ii).

The following specific examples are presented to aid the reader in the synthesis of the compounds of the present invention, but are not intended to limit the scope of the invention in any way.

Abbreviations and Acronyms

When the following abbreviations are used throughout the disclosure, they have the following meaning:
ACN acetonitrile
anhyd anhydrous
$CDCl_3$-d chloroform-d
$CD_2Cl_2$-$d_4$ methylene chloride-$d_4$
CDI 1,1'-dicarbonyldimidazole
Celite® registered trademark of Celite Corp. brand of diatomaceous earth
DIBAL-H diisobutylaluminum hydride
DMF N,N-dimethyl formamide
DMSO-$d_6$ dimethylsulfoxide-$d_6$
EtOAc ethyl acetate
equiv equivalent(s)
h hour(s)
$^1$H NMR proton nuclear magnetic resonance
HCl hydrochloric acid
Hex hexanes
HPLC high performance liquid chromatography
LCMS liquid chromatography/mass spectroscopy
LiH lithium hydride
MeOH methanol
min minute(s)
MS mass spectrometry
Pd/C palladium on carbon
$R_f$ TLC retention factor
Rochelle's salt sodium potassium tartrate
rt room temperature
RT retention time (HPLC)
satd saturated
TFA trifluoroacetic acid
THF tetrahydrofuran
TLC thin layer chromatography General Analytical Procedures The structure of representative compounds of this invention were confirmed using the following procedures.

Electron impact mass spectra (EI-MS) were obtained with a Hewlett Packard 5989A mass spectrometer equipped with a Hewlett Packard 5890 Gas Chromatograph with a J & W DB-5 column (0.25 uM coating; 30 m×0.25 mm). The ion source is maintained at 250° C. and spectra were scanned from 50–800 amu at 2 sec per scan.

High pressure liquid chromatography-electrospray mass spectra (LC-MS) were obtained using either a:

(A) Hewlett-Packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120–1200 amu using a variable ion time according to the number of ions in the source. The eluents were A: 2% acetonitrile in water with 0.02% TFA and B: 2% water in acetonitrile with 0.018% TFA. Gradient elution from 10% B to 95% over 3.5 minutes at a flowrate of 1.0 mL/min is used with an initial hold of 0.5 minutes and a final hold at 95% B of 0.5 minutes. Total run time is 6.5 minutes. or (B) Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120–800 amu over 1.5 seconds. ELSD (Evaporative Light Scattering Detector) data is also acquired as an analog channel. The eluents were A: 2% acetonitrile in water with 0.02% TFA and B: 2% water in acetonitrile with 0.018% TFA. Gradient elution from 10% B to 90% over 3.5 minutes at a flowrate of 1.5 mL/min is used with an initial hold of 0.5 minutes and a final hold at 90% B of 0.5 minutes. Total run time is 4.8 minutes. An extra switching valve is used for column switching and regeneration.

Routine one-dimensional NMR spectroscopy is performed on 300 MHz Varian Mercury-plus spectrometers. The samples were dissolved in deuterated solvents obtained from Cambridge Isotope Labs, and transferred to 5 mm ID Wilmad NMR tubes. The spectra were acquired at 293 K. The chemical shifts were recorded on the ppm scale and were referenced to the appropriate solvent signals, such as 2.49 ppm for DMSO-$d_6$, 1.93 ppm for $CD_3CN$-$d_3$, 3.30 ppm for $CD_3OD$-$d_4$, 5.32 ppm for $CD_2Cl_2$-$d_4$ and 7.26 ppm for $CDCl_3$-d for $^1H$ spectra.

EXAMPLE 1

Preparation of 4-[(3-bromophenyl)amino]-5,6,7,8-tetrahydro[1]benzothieno[2,3-d]pyrimidine-7-carboxylic acid

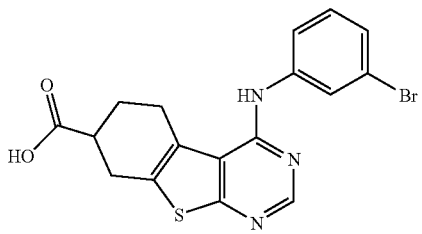

In a 15 mL round-bottom flask were placed 100 mg (0.23 mmol, 1 equiv) of ethyl 4-[(3-bromophenyl)amino]-5,6,7,8-tetrahydro[1]benzothieno[2,3-d]pyrimidine-7-carboxylate in 3 mL of methanol and 1.5 mL of THF. The mixture was stirred until all solids dissolved and then 0.93 mL (0.93 mmol, 4 equiv) of 1N NaOH was added. The reaction was allowed to stir at rt for 16 h and then organic solvents were concentrated in vacuo. The resulting residue was re-dissolved in $H_2O$ (10 mL) and the solution was acidified to pH 5 with 1N HCl. Once the solution was slightly acidic a white solid precipitated; the precipitate was filtered and washed with water (15 mL) and dried in a hi-vac oven overnight to provide 80 mg (87%) of the desired product, 1, as a pure white solid. $^1H$-NMR (DMSO-$d_6$) δ 12.20 (s, 1H), 8.42 (s, 1H), 8.42 (s, 1H), 7.95 (t, 1H), 7.67–7.64 (m, 1H), 7.30–7.21 (m, 2H), 3.25–2.81 (m, 5H), 2.34–2.18 (m, 1H), 1.83–1.97 (m, 1H); LCMS RT=2.94 min; [M+H]$^+$=406.2.

Using the method described above and the appropriate starting materials, Examples 2, 20, 46–47, 50–51 and 53 were similarly prepared.

EXAMPLE 14

Preparation of ethyl 4-[(3-bromophenyl)amino]-5,6,7,8-tetrahydro[1]benzothieno[2,3-d]pyrimidine-7-carboxylate

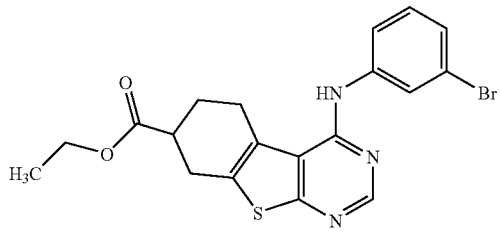

Step 1. Preparation of Example 14: diethyl 2-amino-4,5,6,7-tetrahydro-1-benzothiophene-3,6-dicarboxylate

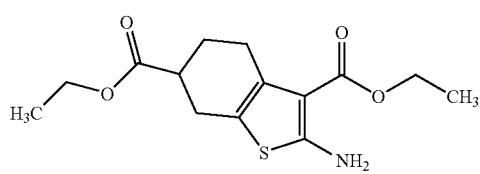

In a 200 mL round-bottom flask were placed 2.0 g (11.75 mmol, 1 equiv) of ethyl cyclohexanone-4-carboxylate, 1.3 g (11.75 mmol, 1 equiv) of ethyl cyanoacetate, 1.02 mL (11.75 mmol, 1 equiv) of morpholine, 376 mg (11.75 mmol, 1 equiv) of elemental sulfur and ethanol (50 mL). The mixture was stirred at rt for 4 days until all sulfur was dissolved. The mixture was concentrated then re-dissolved in EtOAc (75 mL) and poured into a separatory funnel. The organic layer was washed with water (2×75 mL) then dried ($MgSO_4$), filtered, and evaporated. The desired product was obtained in quantitative yield (3.5 g) as a yellow solid and used in further reactions without further purification. $^1H$-NMR ($CDCl_3$-d) δ 4.25 (q, 2H), 4.14 (q, 2H), 2.93 (m,1H), 2.68 (m, 4H), 2.18 (m, 1H), 2.05 (s, 2H), 1.81 (m, 1H), 1.34 (t, 3H), 1.28 (t, 3H). LCMS RT=3.49 min; [M+H]$^+$=297.

Step 2. Preparation of Example 14: Ethyl 4-oxo-3, 4,5,6,7,8-hexahydro[1]benzothieno[2,3-d]pyrimidine-7-carboxylate

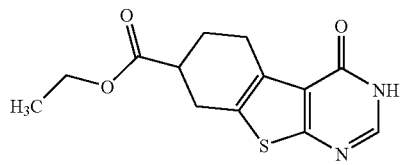

In a 100 mL round-bottom flask was placed 3.5 g (11.75 mmol, 1 equiv) of 2-amino-4,5,6,7-tetrahydro-benzo[b]thiophene-3,6-dicarboxylic acid diethyl ester in 10 mL of formamide. The flask was equipped with a reflux condenser and heated at 140° C. for 16 h. The mixture was then allowed to cool to rt and a brown solid precipitated from solution. The resulting precipitate was filtered and rinsed with EtOAc (200 mL) and dried in a hi-vac oven for 2 h. After drying 3.25 g (99%) of the desired product as a brown solid was obtained and used without further purification in the next step. LCMS RT=2.80 min; [M+H]$^+$=279.

Step 3. Preparation of Example 14: ethyl 4-chloro-5,6,7,8-tetrahydro[1]benzothieno[2,3-d]pyrimidine-7-carboxylate

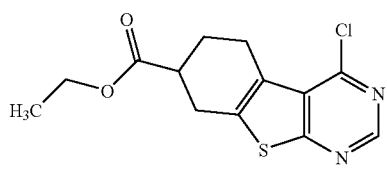

In a 150 mL round-bottom flask was placed 3.0 g (10.78 mmol, 1 equiv) of 4-chloro-5,6,7,8-tetrahydro-benzo[4,5]thieno[2,3-d]pyrimidine-7-carboxylic acid ethyl ester in 60 mL of phosphorous oxychloride. The flask was equipped with a reflux condenser and heated at 80° C. for 2 h. The reaction mixture was cooled to rt and excess phosphorous oxychloride was concentrated in vacuo. Toluene (50 mL) was added to residue and once again concentrated to eliminate remaining POCl$_3$. The resulting crude residue was quenched with ice/water and a solid precipitates from solution. The precipitate was filtered, rinsed with water (100 mL) and dried in a hi-vac oven for 48 h to provide 2.47 g (77%) of the desired product as a light yellow solid. $^1$H-NMR (CDCl$_3$-d) δ 8.75 (s, 1H), 4.21 (q, 2H), 3.11 (m, 4H), 2.91 (m, 1H), 2.37 (m, 1H), 2.05 (m, 1H), 1.25 (t, 3H), 7.36 (t, 1H), 7.35 (t, 1H), 7.20 (t, 1H), 7.02 (t, 1H); LCMS RT=3.04 min; [M+H]$^+$=297.

Step 4. Preparation of Example 14: ethyl 4-[(3-bromophenyl)amino]-5,6,7,8-tetrahydro[1]benzothieno[2,3-d]pyrimidine-7-carboxylate

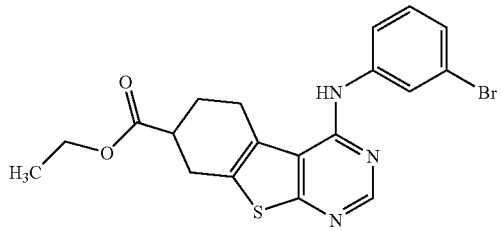

In a 25 mL round-bottom flask were placed 250 mg (0.84 mmol, 1.1 equiv) of 4-chloro-5,6,7,8-tetrahydro-benzo[4,5]thieno[2,3-d]pyrimidine-7-carboxylic acid ethyl ester and 131 mg (0.77 mmol, 1 equiv) m-bromoaniline in 10 mL of ethanol with one drop conc HCl. The flask was equipped with a reflux condenser and heated at 70° C. for 4 h. The mixture was allowed to cool to rt and ethanol was concentrated in vacuo. The resulting crude residue was re-dissolved in EtOAc (10 mL), poured into a separatory funnel and washed with satd NaHCO$_3$ (1×10 mL). The organic layer was dried (MgSO$_4$), filtered and concentrated to give a crude oil. The crude material was further purified by MPLC (Biotage) using 1/4 EtOAc/Hex to provide 257 mg (77%) of the desired product, 14, as a white powder. $^1$H-NMR (CDCl$_3$-d) δ 8.44 (s, 1H), 7.92 (s, 1H), 7.55 (m, 1H), 7.23 (m, 2H), 7.08 (s, 1H), 4.22 (q, 2H), 3.14 (m, 4H), 2.91 (m, 1H), 2.39 (m, 1H), 2.14 (m, 1H), 1.30 (t, 3H); LCMS RT=3.48 min; [M+H]$^+$=432.

Using the method described above and the appropriate starting materials, Examples 24, 32, 39–42, and 44 were similarly prepared.

EXAMPLE 27

Preparation of N-(3-bromophenyl)-7-(1-piperidinylcarbonyl)-5,6,7,8-tetrahydro[1]benzothieno[2,3-d]pyrimidin-4-amine

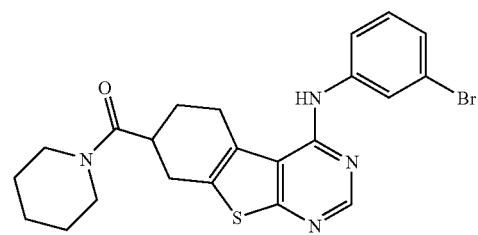

Anhydrous toluene (2 mL) was added to a 50 mL round bottom flask previously evacuated and refilled with argon or nitrogen gas (3×). This was cooled to 0° C. in an ice-water bath for 5 min. Trimethylaluminum, 0.2 mL (1.8 equiv, 2.0M solution in hexanes) was added and the reaction was stirred at 0° C. for 15 min before piperidine (1.1 equiv, 0.25 mmol) was added to the above solution. It was allowed to stir at 0° C. for 10 min before warming to rt for 20 min. A 3 mL toluene solution of 100 mg (0.23 mmol, 1 equiv) of ethyl 4-[(3-bromophenyl)amino]-5,6,7,8-tetrahydro[1]benzothieno[2,3-d]pyrimidine-7-carboxylate, 14, was added and the reaction mixture was heated at 100° C. until reaction was complete by TLC. The reaction mixture was cooled to 0° C. and quenched with 1N HCl. The reaction was adjusted to pH 9.0 with 1N NaOH and extracted with EtOAc (3×5 mL). The organic layer was dried over anhydrous Na$_2$SO$_4$ and concentrated to give a crude oil which was purified via flash column chromatography MeOH/CH$_2$Cl$_2$ 1:9 to provide the required product, 27, as a white solid (100 mg, 92%). $^1$H-NMR (CD$_2$Cl$_2$-d$_4$) δ 8.49 (s, 1H), 8.05 (d, 1H), 7.62–7.59 (m, 1H), 7.23–7.26 (m, 2H), 7.12 (s, 1H), 3.59 (q, 2H), 3.52 (t, 2H), 3.23–3.10 (m, 3H), 2.94 (dd, 1H), 2.20–2.19 (m, 1H), 2.10–2.08 (m, 1H), 1.71–1.58 (m, 7H); LCMS RT=3.28 min; [M+H]$^+$=473.3.

EXAMPLE 30

Preparation of N-(3-bromophenyl)-7-(1-piperidinyl-methyl)-5,6,7,8-tetrahydro[1]benzothieno[2,3-d]pyrimidin-4-amine

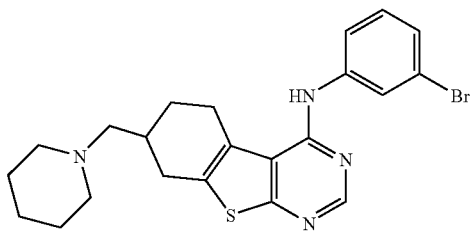

Anhydrous THF (3 mL) was added to a 50 mL round bottom flask followed by N-(3-bromophenyl)-7-(1-piperidinylcarbonyl)-5,6,7,8-tetrahydro[1]benzothieno[2,3-d]pyrimidin-4-amine (27, 0.21 mmol, 1equiv). This was cooled to 0° C. in an ice-water bath for 5 min. Diisobutylaluminum hydride, 0.6 mL (DIBAL-H, 0.64 mmol, 1.0M in THF) was added and the reaction was stirred at 0° C. for 30 min before warming to rt for 2 h until reaction was complete by TLC. The reaction mixture was quenched with a satd solution of Rochelle's salt (3 mL) followed by water (3 mL). The reaction was extracted with EtOAc (3×10 mL). The organic layer was dried over anhyd Na$_2$SO$_4$ and concentrated to give a crude oil which was purified via flash column chromatography MeOH/CH$_2$Cl$_2$ 1:9 w/0.5% NH$_4$OH to provide the required product, 30, as an oil (70 mg, 72%). $^1$H-NMR (CD$_2$Cl$_2$-d$_4$) δ 8.36 (s, 1H), 7.94 (t, 1H), 7.50–7.47 (m, 1H), 7.15–7.13 (m, 2H), 7.10 (s, 1H), 2.95–2.91 (m, 3H), 2.29–2.05 (m, 7H), 1.52–1.47 (m, 5H), 1.36 (t, 1H); LCMS RT=2.36 min; [M+H]$^+$=459.2.

Using the method described above and the appropriate starting materials, Examples 4, 7, 11–12, 15, 17, 22, 25–26, 30, 33–38, 55 and 66 were similarly prepared.

EXAMPLE 56

Preparation of N-allyl-4-[(3-bromophenyl)amino]-5,6,7,8-tetrahydro[1]benzothieno[2,3-d]pyrimidine-7-carboxamide

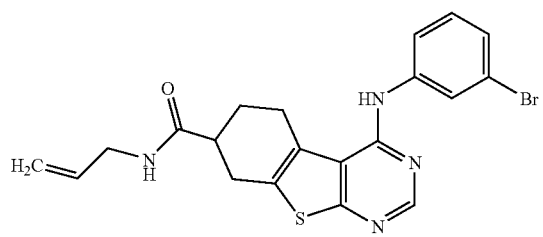

To a 15 mL round-bottom flask were added 50 mg (0.124 mmol, 1 equiv) of 4-[(3-bromophenyl)amino]-5,6,7,8-tetrahydro[1]benzothieno[2,3-d]pyrimidine-7-carboxylic acid, 1, 20 mg (0.124 mmol, 1 equiv) of CDI and THF (1.25 mL). The reaction was stirred for 4 h at rt and then 0.01 mL (0.186 mmol, 1.5 equiv) of allyl amine was added via syringe and the reaction was allowed to stir at rt overnight. The reaction was stopped and THF was concentrated in vacuo and the crude solid was re-dissolved in CH$_2$Cl$_2$ (5 mL). This solution was poured into a separatory funnel and washed with satd NaHCO$_3$ (1×5 mL), water (1×5 mL), and brine (1×5 mL). The organic layer was dried (MgSO$_4$), filtered and concentrated to yield a white solid. The compound was triturated with diethyl ether to yield pure material, 56, as a white solid (36 mg, 66%). $^1$H-NMR (DMSO-d$_6$) δ 8.42 (s, 1H), 8.31 (s, 1H), 8.19 (t, 1H), 7.86 (m, 1H), 7.63 (m, 1H), 7.25 (m, 2H), 5.82 (m, 1H), 5.08 (m, 2H), 3.75 (t, 2H), 3.21 (m, 2H), 2.97 (d, 2H), 2.69 (m, 1H), 2.15 (m, 1H), 1.82 (m, 1H); LCMS RT=2.78 min; [M+H]$^+$=444.

Using the methods described above in Examples 27 and 56 and the appropriate starting materials, Examples 18–19, 21, 23, 27–29, 31, 43, 48–49, 52, 56 and 60 were similarly prepared.

EXAMPLE 63

Preparation of ethyl {4-[(3-bromophenyl)amino]-5,6,7,8-tetrahydro[1]benzothieno[2,3-d]pyrimidin-7-yl}acetate

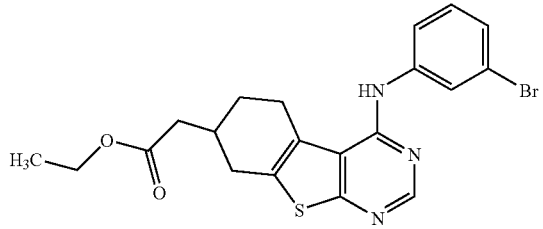

Step 1. Preparation of Example 63: ethyl 1,4-dioxaspiro[4,5]dec-8-ylideneacetate

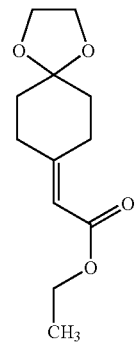

To a solution of THF (18 mL) under argon was added 0.38 g (47.8 mmol, 5 equiv) of LiH, followed by slow addition of 8.78 g (47.8 mmol, 5 equiv) of triethyl phosphonoacetate. The solution was stirred at rt for 1 h and 1.49 g (9.6 mmol, 1 equiv) of 1,4-cyclohexanedione mono-ethylene ketal was added and the solution was heated at 65° C. for 16 h. Upon cooling the solution was treated with MeOH (10 mL) and water (5 mL) and concentrated in vacuo. The resulting yellow oil was purified by silica gel chromatography eluting with 4:1 Hex/EtOAc to yield 1.89 g (93%) of a clear oil.

$^1$H-NMR (CDCl$_3$-d) δ 5.67 (s, 1H), 4.16 (t, 2H), 3.99 (m, 4H), 3.02 (m, 2H), 2.39 (m, 2H), 1.78 (m, 4H), 1.29 (t, 3H); LCMS RT=2.56 min; [M+H]$^+$=226.9.

Step 2. Preparation of Example 63: ethyl 1,4-dioxaspiro[4,5]dec-8-ylacetate

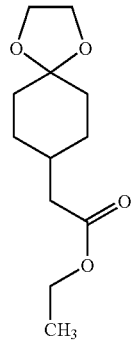

To a solution of EtOH (100 mL) was added 182 mg (10% by weight) Pd/c under argon. As a solution in EtOH, 1.82 g (8.0 mmol, 1 equiv) ethyl 1,4-dioxaspiro[4,5]dec-8-ylideneacetate was added via syringe. The flask was charged with hydrogen (3×) and left stirring for 16 h. The flask was evacuated and charged with argon (3×) and the solution was filtered through a pad of Celite® washing with EtOH (200 mL). The solution was evaporated under reduced pressure yielding 1.74 g (95%) of a clear oil. $^1$H-NMR (CDCl$_3$-d) δ 4.13 (q, 2H), 3.95 (m, 4H), 2.24 (m, 2H), 1.96 (m,1H), 1.75 (m, 4H), 1.58 (m, 2H), 1.31 (m, 2H), 1.27 (t, 3H); TLC R$_f$=0.20 (1:9 EtOAc/Hex).

Step 3. Preparation of Example 63: ethyl (4-oxocyclohexyl)acetate

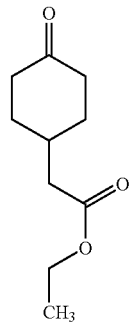

To a solution of acetone (720 mL) was added 10 g (43.8 mmol, 1 equiv) of ethyl 1,4-dioxaspiro[4,5]dec-ylacetate followed by 1 N Hydrochloric acid (180 mL) The reaction was heated at reflux for 2 h. Upon cooling the solution was diluted with EtOAc (100 mL) and washed with water (100 mL). The water layer was back extracted twice with EtOAc (100 mL) and the organic layers were combined, dried (MgSO$_4$), filtered and concentrated to yield 7.57 g (94%) of a clear oil. $^1$H-NMR (CDCl$_3$-d) δ 4.16 (q, 2H), 2.40 (m, 4H), 2.32 (m, 2H), 2.28 (m, 1H), 2.10 (m, 2H), 1.49 (m, 2H), 1.28 (t, 3H); TLC R$_f$=0.32 (3:7 EtOAc/Hex).

Step 4. Preparation of Example 63: ethyl 2-amino-6-(2-ethoxy-2-oxoethyl)-4,5,6,7-tetrahydro-1-benzothiophene-3-carboxylate

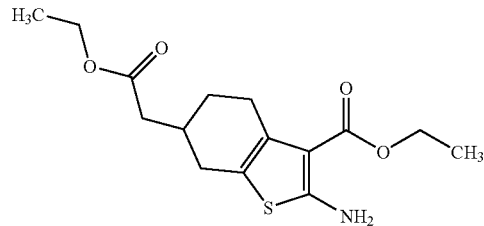

The compound was prepared as described in Example 14, Step 1.

$^1$H-NMR (CDCl$_3$-d) δ 5.96 (s, 2H), 4.25 (q, 2H), 4.15 (q, 2H), 2.87 (m, 1H), 2.65 (m, 2H), 2.32 (m, 4H), 1.91 (m, 1H), 1.46 (m, 1H), 1.34 (t, 3H), 1.28 (t, 3H); LCMS RT=3.17 min; [M+H]$^+$=312.0.

Step 5. Preparation of Example 63: ethyl (4-oxo-3,4,5,6,7,8-hexahydro[1]benzothieno[2,3-d]pyrimidin-7-yl)acetate

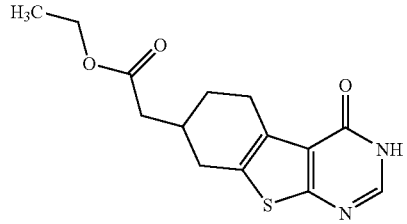

The compound was prepared as described in Example 14, Step 2.

$^1$H-NMR (DMSO-d$_6$) δ 12.31 (s, 1H), 7.99 (s, 1H), 4.09 (q, 2H), 3.06 (m, 1H), 2.87 (m, 1H), 2.75 (m, 1H), 2.40 (m, 3H), 2.19 (m, 1H), 1.89 (m, 1H), 1.47 (m, 1H), 1.19 (t, 3H); LCMS RT=2.40 min; [M+H]$^+$=293.1.

Step 6. Preparation of Example 63: ethyl (4-chloro-5,6,7,8-tetrahydro[1]benzothieno[2,3-d]pyrimidin-7-yl)acetate

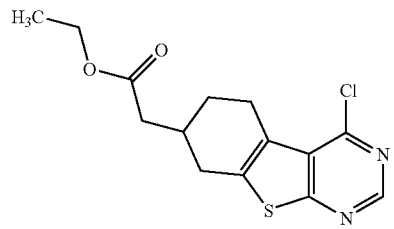

The compound was prepared as described in Example 14, Step 3.

¹H-NMR (CDCl₃-d) δ 8.72 (s, 1H), 4.19 (q, 2H), 3.31 (m, 1H), 3.07 (m, 2H), 2.65 (m, 1H), 2.46 (m, 3H), 2.12 (m, 1H), 1.65 (m, 1H), 1.31 (t, 3H); LCMS RT=3.70 min; [M+H]⁺=311.2.

Step 7. Preparation of Example 63: ethyl {4-[(3-bromophenyl)amino]-5,6,7,8-tetrahydro[1]benzothieno[2,3-d]pyrimidin-7-yl}acetate

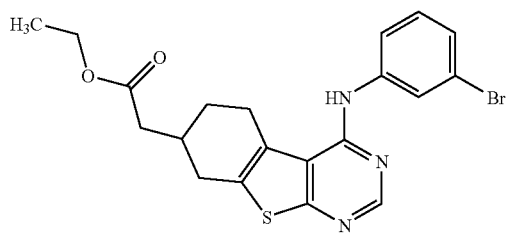

The compound was prepared as described in Example 14, Step 4.

¹H-NMR (CD₂Cl₂-d₄) δ 8.47 (s, 1H), 8.06–8.04 (m, 1H), 7.60–7.57 (m, 1H), 7.26–7.24 (m, 2H), 7.16 (s, 1H), 4.17 (q, 2H), 3.16–3.02 (m, 3H), 2.67–2.59 (m, 1H), 2.46 (s, 3H), 2.21–2.16 (m, 1H), 1.76–1.69 (m, 1H), 1.30 (t, 3H); LCMS RT=4.00 min; [M+H]⁺=448.2.

Using the method described above and the appropriate starting materials, Example 57 was similarly prepared.

EXAMPLE 65

Preparation of {4-[(3-bromophenyl)amino]-5,6,7,8tetrahydro[1]benzothieno[2,3-d]pyrimidin-7-yl}acetic acid

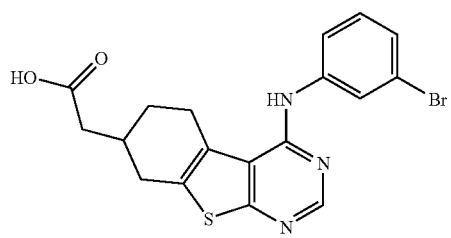

The compound was prepared as described in Example 1.

¹H-NMR (CD₃OD-d₄) δ 8.51 (s, 1H), 7.88 (s, 1H), 7.57–7.36 (m, 3H), 3.26–3.10 (m, 2H), 2.72–2.65 (m, 1H), 2.48 (s, 3H), 2.24–2.16 (m, 1H), 1.76–1.68 (m, 1H); LCMS RT=3.48 min; [M+H]⁺=420.2.

Using the method described above and the appropriate starting materials, Example 72 was similarly prepared.

EXAMPLE 70

Preparation of N-3-bromophenyl)-7-[2-(4-morpholinyl)-2-oxoethyl]-5,6,7,8-tetrahydro[1]benzothieno[2,3-d]pyrimidin-4-amine

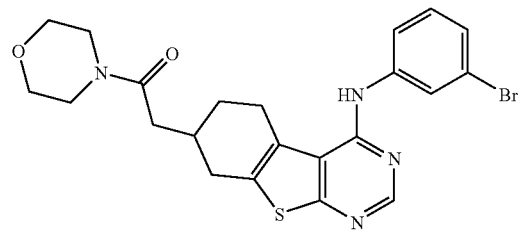

The compound was prepared as described in Example 27.

¹H-NMR (CD₂Cl₂-d₄) δ 8.36 (s, 1H), 7.95 (t, 1H), 7.49–7.46 (m, 1H), 7.15–7.13 (m, 2H), 7.10 (s, 1H), 3.57–3.49 (m, 9H), 3.38–3.34 (m, 2H), 3.04–2.95 (m, 4H), 2.50–2.46 (m, 1H), 2.36–2.32 (m, 3H), 2.13–2.05 (m, 1H), 1.66–1.56 (m, 1H); LCMS RT=2.91 min; [M+H]⁺=487.4.

Using the method described above and the appropriate starting materials, Examples 58, 61–62, 67–71, 77, 81–83, 91–92 and 103–105 were similarly prepared.

EXAMPLE 85

Preparation of N-(3-bromophenyl)-7-[2-(1-pyrrolidinyl)ethyl]-5,6,7,8-tetrahydro[1]benzothieno[2,3-d]pyrimidin-4-amine

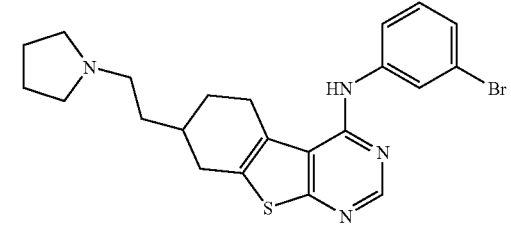

Step 1. Preparation of Example 85: 2-{4-[(3-bromophenyl)amino]-5,6,7,8-tetrahydro[1]benzothieno[2,3-d]pyrimidin-7-yl}ethanol (102)

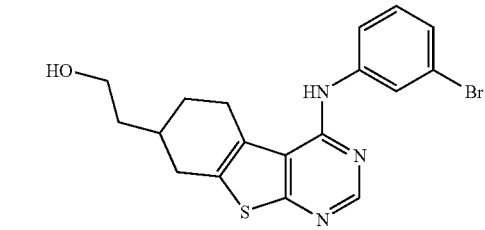

To a solution of THF (45 mL) was added 0.70 g (1.57 mmol, 1 equiv) of ethyl {4-[(3-bromophenyl)amino]-5,6,7,8-tetrahydro[1]benzothieno[2,3-d]pyrimidin-7-yl}acetate. A 1M solution of diisobutylaluminum hydride in hexanes (6.43 mL, 6.43 mmol, 4.1 equiv) was added to the solution and the reaction was stirred at rt for 1 h. The reaction mixture was quenched with Rochelle's salt followed by EtOAc. The solution was separated and the aqueous layer discarded and the organic layer was washed with brine (1×25 mL) and water (1×25 mL). The resulting crude material was purified by flash chromatography eluting with 95:5 $CH_2Cl_2$/MeOH yielding 630 mg (99%) of 102 as a white solid. $^1$H-NMR ($CDCl_3$-d) δ 8.52 (s, 1H), 7.95 (m, 1H), 7.56 (m, 1H), 7.24 (m, 2H), 7.11 (s, 1H), 3.84 (m, 2H), 3.08 (m, 3H), 2.57 (m, 1H), 2.16 (m, 2H), 1.73 (m, 4H); TLC $R_f$=0.22 (95:5 $CH_2Cl_2$/MeOH); LCMS RT=2.91 min; [M+H]$^+$=404.2.

Using the method described above and the appropriate starting materials, Example 64 was similarly prepared.

Step 2. Preparation of Example 85: N-[7-(2-bromoethyl)-5,6,7,8-tetrahydro[1]benzothieno[2,3-d]pyrimidin-4-yl]-N-(3-bromophenyl)amine

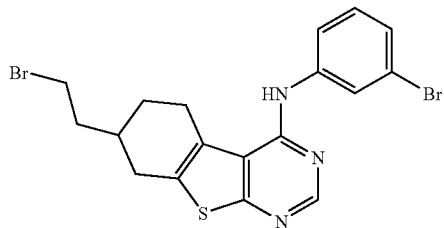

To a solution of THF (20 mL) was added 0.63 (102, 1.56 mmol, 1 equiv) of 2-{4-[(3-bromophenyl)amino]-5,6,7,8-tetrahydro[1]benzothieno[2,3-d]pyrimidin-7-yl}ethanol, 0.82 g (3.12 mmol, 2 equiv) triphenylphosphine and 1.03 g (3.12 mmol, 2 equiv) carbon tetrabromide. The solution was stirred at rt for 1 h until completion and the reaction mixture was evaporated under reduced pressure. The resulting crude material was purified by flash chromatography eluting with 9:1 $CH_2Cl_2$/EtOAc yielding 396 mg (54%) of a light yellow solid. $^1$H-NMR ($CDCl_3$-d) δ 8.52 (s, 1H), 7.94 (m, 1H), 7.58 (m, 1H), 7.24 (m, 2H), 7.10 (s, 1H), 3.56 (m, 2H), 3.15 (m, 2H), 3.03 (m, 1H), 2.57 (m, 1H), 2.19 (m, 2H), 2.04 (m, 2H), 1.68 (m, 1H); TLC $R_f$=0.30 (9:1 $CH_2Cl_2$/EtOAc); LCMS RT=3.92 min; [M+H]$^+$=466.2.

Step 3. Preparation of Example 85:N-(3-bromophenyl)-7-[2-(1-pyrrolidinyl)ethyl]-5,6,7,8-tetrahydro[1]benzothieno[2,3-d]pyrimidin-4-amine

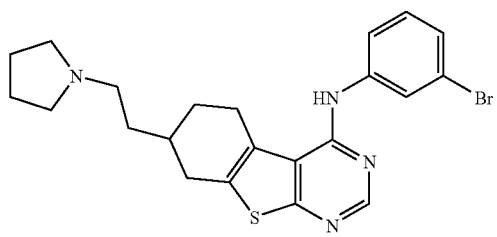

To a solution of DMF was added 46 mg (0.10 mmol, 1 equiv) of N-[7-(2-bromoethyl)-5,6,7,8-tetrahydro[1]benzothieno[2,3-d]pyrimidin-4-yl]-N-3-bromophenyl)amine, 15 mg (0.10 mmol, 1 equiv) sodium iodide, 21 mg (0.20 mmol, 2 equiv) sodium carbonate, and 14 mg (0.20 mmol, 2 equiv) pyrrolidine. The solution was heated at 80° C. for 2 h and upon cooling was purified by prep HPLC (10–90% ACN/H2O). The resulting pure fractions were made basic in aqueous saturated sodium bicarbonate and extracted into EtOAc (10 mL). The EtOAc layer was washed with water (1×10 mL) and then collected and dried over $MgSO_4$. The solution was evaporated under reduced pressure yielding 24 mg (54%) of desired product 85 as a clear oil. $^1$H-NMR ($CDCl_3$-d) δ 8.52 (s, 1H), 7.94 (m, 1H), 7.58 (m, 1H), 7.22 (m, 2H), 7.13 (s, 1H), 3.10 (m, 2H), 3.00 (m, 1H), 2.59 (m, 7H), 2.16 (m, 1H), 1.98 (m, 1H), 1.84 (m, 4H), 1.70 (m, 3H); TLC $R_f$=0.23 (9:1 $CH_2Cl_2$/MeOH); LCMS RT=2.33 min; [M+H]$^+$=457.2.

Using the method described above and the appropriate starting materials, Examples 54, 59, 73–76, 78–80, 84–89, 93–94 and 96–100 were similarly prepared.

EXAMPLE 90

Preparation of N-(3-bromophenyl)-7-(2-methoxyethyl)-5,6,7,8-tetrahydro[1]benzothieno[2,3-d]pyrimidin-4-amine

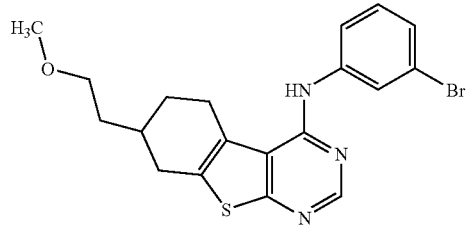

To a solution of DMF were added 52 mg (0.11 mmol, 1 equiv) of N-[7-(2-bromoethyl)5,6,7,8tetrahydro[1]benzothieno[2,3-d]pyrimidin-4-yl]-N-(3-bromophenyl)amine, 17 mg (0.11 mmol, 1 equiv) sodium iodide, and 18 mg (0.33 mmol, 3 equiv) sodium methoxide. The solution was heated at 80° C. for 2 h and upon cooling the solution was purified by prep HPLC (10–90% ACN-H$_2$O). The resulting pure fractions were made basic in aqueous saturated sodium bicarbonate and extracted into EtOAc (10 mL). The EtOAc layer was washed with water (1×10 mL) and dried over $MgSO_4$. The solution was evaporated under reduced pressure yielding 20 mg (44%) of desired product, 90, as a white solid. $^1$H-NMR ($CDCl_3$-d) δ 8.52 (s, 1H), 7.94 (m, 1H), 7.59 (m, 1H), 7.24 (m, 2H), 7.13 (s, 1H), 3.55 (t, 2H), 3.39 (s, 3H), 3.12 (m, 2H), 3.01 (m, 1H), 2.56 (m, 1H), 2.13 (m, 2H), 1.74 (m, 3H); TLC $R_f$=0.75 (9:1 $CH_2Cl_2$/MeOH); LCMS RT=3.57 min; [M+H]$^+$=418.2.

Using the method described above and the appropriate starting materials, Example 101 was similarly prepared.

EXAMPLE 95

Preparation of 1-{4-[(3-bromophenyl)amino]-5,6,7,8-tetrahydro[1]benzothieno[2,3-d]pyrimidin-7-yl}-2-methyl-2-propanol

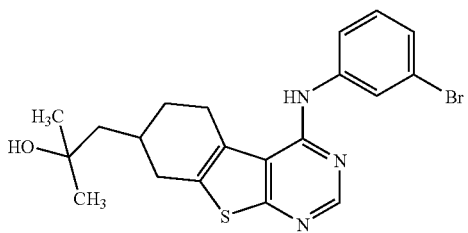

The compound was prepared as described in Example 27 with the exception that imidazole was used in place of piperidine.

$^1$H-NMR (CD$_2$Cl$_2$-d$_4$) δ 8.35 (s, 1H), 7.94 (s, 1H), 7.49–7.46 (m, 1H), 7.14–7.12 (m, 2H), 7.10 (s, 1H), 3.03–2.97 (m, 3H), 2.55–2.45 (m, 1H), 2.12–2.02 (m, 2H), 1.56–1.46 (m, 4H), 1.99 (s, 6H); LCMS RT=3.32 min; [M+H]$^+$=432.3.

EXAMPLE 136

Preparation of {4-[3-Chloro-4-(3-fluoro-benzyloxy)-phenylamino]-5,6,7,8-tetrahydro-benzo[4,5]thieno[2,3-d]pyrimidin-7-yl}-acetic acid ethyl ester

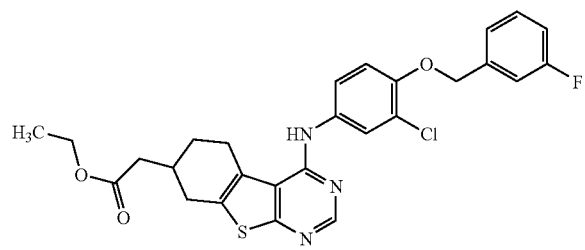

Step 1. Preparation of 3-Chloro-4-(3-fluoro-benzyloxy)phenylamine

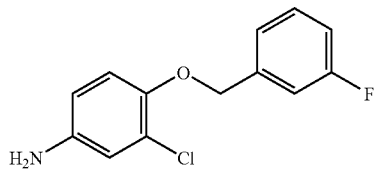

2-Chloro-1-(3-fluoro-benzoyloxy)-4-nitro-benzene 10 g (35.5 mmol, 1 eq) was suspended in 50 mL acetic acid and 150 mL ethyl acetate in a 500 mL flask. Iron 9.9 g (177.5 mmol, 5 eq) was added to this suspension. The reaction was stirred at rt overnight. The reaction mixture was filtered through celite pad. The filtrate was concentrated in vacuo and neutralized with sat. Na$_2$CO$_3$ solution, followed by ethyl acetate extraction. The organic layer was washed with brine and concentrated in vacuo. The resulting crude material was purified by flash chromatography eluting with 15% ethyl acetate/hexane yielding 8.5 g of 3-chloro-4-(3-fluoro-benzyloxy)-phenylamine as a brown solid (95%, TLC Rf=0.4, 30% AcOEt/HEX.).

$^1$H-NMR (CDCl$_3$) δ 3.5 (s, 2H), 5.0 (s, 2H), 6.5 (dd, 1H), 6.76 (m, 2H), 7.0 (m, 1H), 7.2 (m,2H), 7.32 (m,1H).

Following the same procedure 3-Chloro-4-(4-fluoro-benzyloxy)-phenylamine was prepared as well (TLC Rf=0.4, 30% AcOEt/HEX.). $^1$H-NMR (CDCl3) δ 3.5 (s, 2H), 5.0 (s, 2H), 6.5 (dd, 1H), 6.76 (m, 2H), 7.05 (m, 2H), 7.4 (m, 2H).

Step 2. Preparation of Example 136: {4-[3-Chloro-4-(3-fluoro-benzyloxy)-phenylamino]-5,6,7,8-tetrahydro-benzo[4,5]thieno[2,3-d]pyrimidin-7-yl}-acetic acid ethyl ester

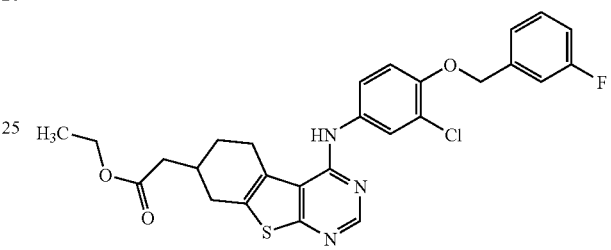

The compound was prepared as described in Example 14, Step 4.

$^1$H-NMR (CDCl$_3$) δ 1.2 (t, 3H), 1.7 (1H), 2.15 (1H), 2.45 (3H), 2.6 (1H), 3.1 (3H), 4.1 (q, 2H), 5.14 (s, 2H), 6.9 (2H), 7.0 (td, 1H), 7.2 (2H), 7.33 (m, 1H), 7.42 (dd, 1H), 7.69 (d, 1H), 8.45 (s, 1H). LCMS RT=4.01 min; [M+H]$^+$=526.2.

EXAMPLE 137

Preparation of 2-{4-[3-Chloro-4-(3-fluoro-benzyloxy)-phenylamino]-5,6,7,8-tetrahydro-benzo[4,5]thieno[2,3-d]pyrimidin-7-yl}-ethanol

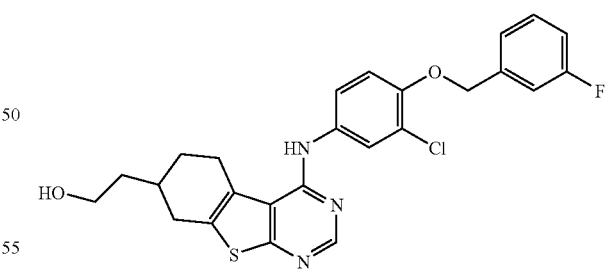

To a solution of THF (40 mL) was added 7 g (13.3 mmol, 1 equiv) of {4-[3-Chloro-4-(3-fluoro-benzyloxy)-phenylamino]-5,6,7,8-tetrahydro-benzo[4,5]thieno[2,3-d]pyrimidin-7-yl}-acetic acid ethyl ester. A 1M solution of diisobutylaluminum hydride in hexanes (53 mL, 53 mmol, 4 equiv) was added to the solution and the reaction was stirred at rt for 3 h. The reaction mixture was quenched with Rochelle's salt followed by EtOAc. The solution was separated and the aqueous layer discarded and the organic layer was washed with brine (100 mL) and water (100 mL). The resulting material 5.5 g (85%)was pure white solid of Example 137.
$^1$H-NMR (DMSO-d6) δ 1.5 (m, 3H), 1.95 (m, 2H), 2.93 (dd,1H), 3.16 (2H), 3.53 (m,2H), 4.45 (t, 1H), 5.2 (s, 2H), 7.17 (m, 2H), 7.28 (m,2H), 7.43 (m, 1H), 7.5 (dd, 2H), 7.76 (dd, 1H), 8.05 (s, 1H). LCMS RT=3.46 min; [M+H]$^+$=484.2.

EXAMPLE 138

Preparation of [7-(2-Bromo-ethyl)-5,6,7,8-tetrahydro-benzo[4,5]thieno[2,3-d]pyrimidin-4-yl]-[3-chloro-4-(3-fluoro-benzyloxy)-phenyl]-amine

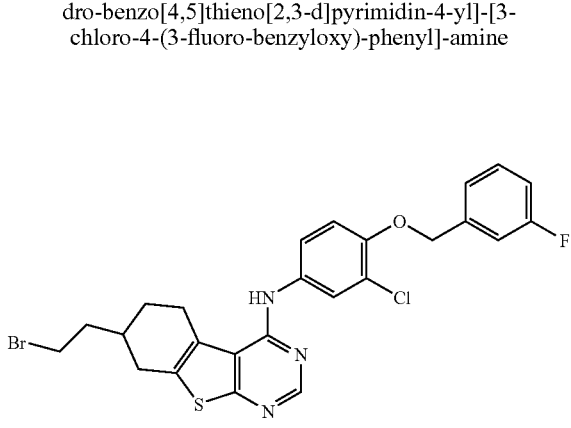

The compound was prepared as described in Example 85, Step 2.
$^1$H-NMR (CDCl3) δ 1.68 (1H), 2.02 (m, 2H), 2.18 (2H), 2.54 (1H), 3.0 (dd, 1H), 3.1 (2H), 3.55 (m, 2H), 5.15 (s, 2H), 6.94 (2H), 7.02 (m, 1H), 7.21 (m, 2H), 7.35 (m, 1H), 7.42 (dd, 1H), 7.71 (d, 1H), 8.46 (s, 1H). LCMS RT=4.41 min; [M+H]$^+$=546.3.

EXAMPLE 160

Preparation of [3-chloro-4-(3-fluoro-benzyloxy)-phenyl-{7-[2-(3-dimethylamino-pyrrolidin-1-yl)-ethyl]-5,6,7,8-tetrahydro-benzo[4,5]thieno[2,3-d]pyrimidin-4-yl}-amine

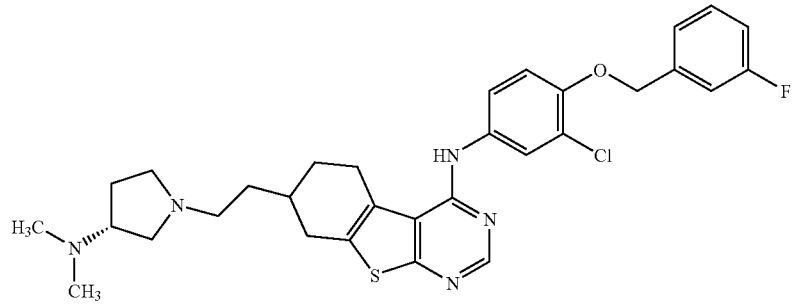

The compound was prepared as described in Example 85, Step 3.
$^1$H-NMR (CDCl3) δ 1.70 (m, 3H), 2.00 (m, 2H), 2.10 (2H), 2.22 (s, 6H), 2.30 (m, 1H), 2.50 (m, 4H), 2.80 (m, 2H), 3.00 (m, 4H), 5.12 (s,2H), 6.94 (2H), 7.02 (m, 1H), 7.21 (m, 2H), 7.35 (m, 1H), 7.42 (dd, 1H), 7.71 (d, 1H), 8.44 (s, 1H). LCMS RT=1.87 min; [M+H]+=580.2

Using the method described above and the appropriate starting materials, Examples 139, 140, 142–172, 186, 197, 200 were similarly prepared.

EXAMPLE 173

Preparation of {4-[3-Chloro-4-(pyridin-2-ylmethoxy)-phenylamino]-5,6,7,8-tetrahydro-benzo[4,5]thieno[2,3-d]pyrimidin-7-yl}-acetic acid ethyl ester

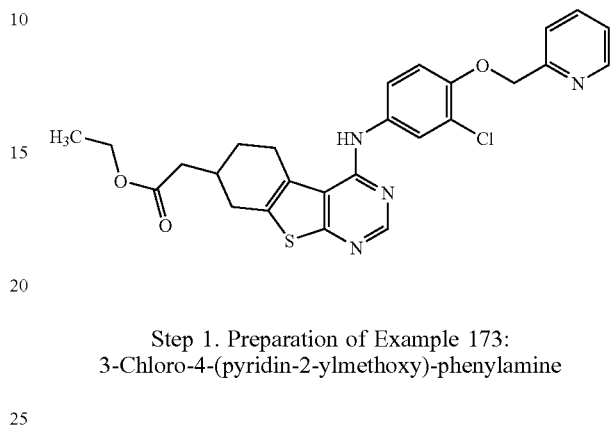

Step 1. Preparation of Example 173: 3-Chloro-4-(pyridin-2-ylmethoxy)-phenylamine

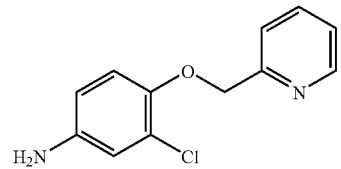

2-chloro-4-nitro phenol 10 g (57.6 mmol, 1 eq), 2-pycolyl chloride hydrogen chloride 9.45 g (57.6 mmol, 1 eq) cesium carbonate 41.3 (126.8 mmol, 2.2 eq) and sodium iodide 8.64 g (57.6 mmol, 1 eq) were suspended in 200 mL acetonitrile. The reaction mixture was stirred at 60° C. for 5 h. The resulted suspension was filtered and washed with 400 mL water, yielding 2-(2-chloro-4-nitro-phenoxymethyl)-pyridine (8 g, 52%) as a red solid.

2-(2-chloro-4-nitro-phenoxymethyl)-pyridine (8 g, 30.2 mmol, 1 eq) and 8.44 g iron (151.1 mmol, 5 eq) were mixed in 100 mL acetic acid and 50 mL ethyl acetate and were stirred at rt overnight. The reaction mixture was filtered through celite pad. The filtrate was concentrated in vacuo and neutralized with sat. Na$_2$CO$_3$ solution. The solution was extracted with ethyl acetate and the organic layer was washed with brine and concentrated in vacuo. The resulting crude material was purified by flash chromatography eluting with 30% ethyl acetate/hexane yielding 3.2 g of 3-chloro-4-(pyridin-2-ylmethoxy)-phenylamine as a white solid (52%). $^1$H-NMR (CDCl$_3$) δ 5.18 (s, 2H), 6.50 (dd, 1H), 6.76 (d, 1H), 6.80 (d, 1H), 7.22 (m, 1H), 7.64 (d, 1H), 7.73 (td, 1H), 8.55 (m, 1H); LCMS RT=0.89 min; [M+H]$^+$=235.1.

Step 2. Preparation of Example 173: {4-[3-chloro-4-(pyridin-2-ylmethoxy)-phenylamino]-5,6,7,8-tetrahydro-benzo[4,5]thieno[2,3-d]pyrimidin-7-yl}-acetic acid ethyl ester

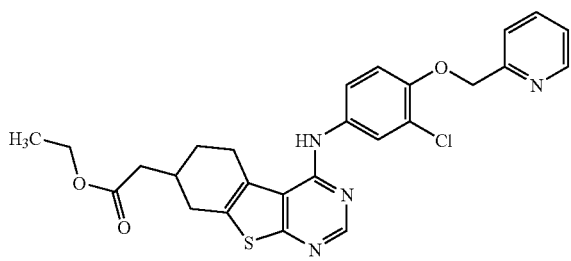

The compound was prepared as described in Example 14, Step 4.

$^1$H-NMR (CD$_3$OD) δ 8.78 (s, 1H), 8.39 (s, 1H), 8.36 (t, 1H), 8.03 (d, J=7.9 Hz, 1H), 7.8 (m, 2H), 7.51 (dd, J=2.8, 8.8 Hz, 1H), 7.26 (d, J=8.8 Hz, 1H), 5.46 (s, 2H), 4.18 (q, 2H), 3.26–3.05 (m, 3H), 2.65 (m, 1H), 2.50 (d, J=7.0 Hz, 2H), 2.42 (m, 1H), 2.16 (m, 1H), 1.70 (m, 1H), 1.29 (t, 3H). LCMS RT=3.18 min; [M+H]$^+$=509.

EXAMPLE 174

Preparation of 2-{4-[3-Chloro-4-(pyridin-2-ylmethoxy)-phenylamino]-5,6,7,8-tetrahydro-benzo[4,5]thieno[2,3-d]pyrimidin-7-yl}-ethanol

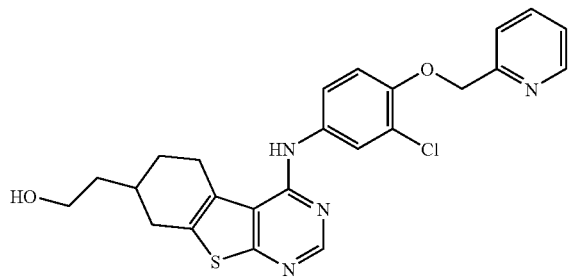

The compound was prepared as described in Example 137.

$^1$H-NMR (CDCl$_3$) δ 1.75 (m, 3H), 2.12 (2H), 2.58 (m, 1H), 3.02 (m, 3H), 3.48 (s, 1H), 3.80 (t, 2H), 5.24 (s, 2H), 6.98 (m, 2H), 7.21 (m, 1H), 7.40 (dd, 1H), 7.62 (d, 1H), 7.70 (m, 2H), 8.42 (s, 1H), 8.60 (d, 1H). LCMS RT=3.03 min; [M+H]$^+$=467.2.

EXAMPLE 175

Preparation of Methanesulfonic acid 2-{4-[3-chloro-4-(pyridin-2-ylmethoxy)-phenylamino]-5,6,7,8-tetrahydro-benzo[4,5]thieno[2,3-d]pyrimidin-7-yl}-ethyl ester

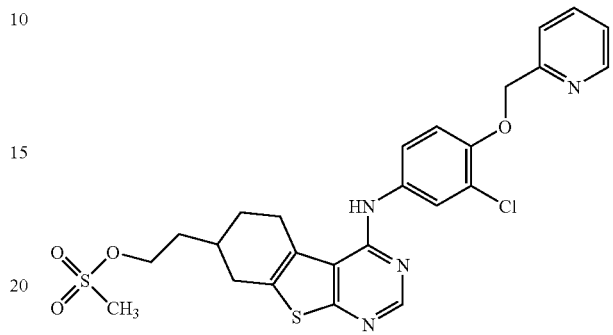

Methanesulfonyl chloride (0.48 mL, 707 mg, 6.17 mmol, 1.2 equiv.) was added to a suspension of 2-{4-[3-Chloro-4-(pyridin-2-ylmethoxy)-phenylamino]-5,6,7,8-tetrahydro-benzo[4,5]thieno[2,3-d]pyrimidin-7-yl}-ethanol (2.4 g, 5.14 mmol, 1 equiv.) in anhydrous DCM (20 mL) at 0° C. The resulting mixture was stirred overnight during which time it was warmed to ambient temperature. The standard aqueous work-up gave Methanesulfonic acid 2-{4-[3-chloro-4-(pyridin-2-ylmethoxy)-phenylamino]-5,6,7,8-tetrahydro-benzo[4,5]thieno[2,3-d]pyrimidin-7-yl}-ethyl ester as a slight yellow solid (2.3 g, 79%). $^1$H-NMR (CD$_3$OD) δ 8.56 (s, 1H), 8.33 (s, 1H), 7.85 (t, 1H), 7.79 (d, J=2.4 Hz, 1H), 7.55 (d, J=7.9 Hz, 1H), 7.51 (dd, J=2.5, 9.1 Hz, 1H), 7.34 (m, 1H), 7.20 (d, J=8.8 Hz, 1H), 5.27 (s, 2H), 4.35 (t, 2H), 3.19 (s, 3H), 3.15 (m, 3H), 2.97 (m, 1H), 2.17 (m, 2H), 1.81 (m, 2H), 1.54 (m, 1H).; LCMS RT=3.03 min; [M+H]$^+$=545.

EXAMPLE 177

Preparation of [3-Chloro-4-(pyridin-2-ylmethoxy)-phenyl]-[7-(2-morpholin-4-yl-ethyl)-5,6,7,8-tetrahydro-benzo[4,5]thieno[2,3-d]pyrimidin-4-yl]-amine

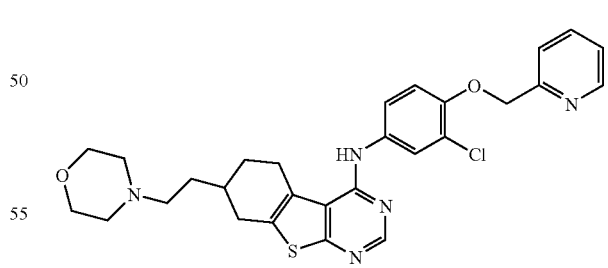

Morpholine (0.03 mL, 26. mg, 0.30 mmol, 1.2 equiv.) was added to a suspension of Methanesulfonic acid 2-{4-[3-chloro-4-(pyridin-2-ylmethoxy)-phenylamino]-5,6,7,8-tetrahydro-benzo[4,5]thieno[2,3-d]pyrimidin-7-yl}-ethyl ester (135 mg, 0.25 mmol, 1 quiv.) and DIEA (0.09 mL, 0.5 mmol, 2 equiv.) in anhydrous acetonitrile (2.0 mL). The resulting mixture was stirred overnight at 80° C. at which time TLC (MeOH/DCM 5:95) indicated no more starting material left. The solvents were evaporated and residue was purified by preparative TLC (20 cm×20 cm×1 mm silica, MeOH/DCM 5:95) to give [3-Chloro-4-(pyridin-2-yl-methoxy)-phenyl]-[7-(2-morpholin-4-yl-ethyl)-5,6,7,8-tetrahydro-benzo[4,5]thieno[2,3-d]pyrimidin-4-yl]-amine as a white solid (16 mg, 12%). $^1$H-NMR (CD$_3$OD) δ 8.51 (s, 1H), 8.24 (s, 1H), 7.87 (t, 1H), 7.81 (d, J=2.4 Hz, 1H) 7.68 (d, J=7.5 Hz, 1H), 7.36 (m, 2H), 7.02 (d, J=9.2 Hz, 1H), 5.18 (s, 2H), 2.69 (t, 4H), 3.35 (s, 1H), 3.11 (m, 1H), 3.02 (m, 1H), 2.91 (m, 1H), 2.48 (m, 6H), 2.09 (m, 1H), 1.89 (m, 1H), 1.62 (m, 3H).; LCMS RT=2.25 min; [M+H]$^+$=536.

Using the method described above and the appropriate starting materials, Examples 141, 173–185, 187 and 196 were similarly prepared.

EXAMPLE 203

Preparation of 2-[4-(1-Benzyl-1H-indazol-5-ylamino)-5,6,7,8-tetrahydro-benzo[4,5]thieno[2,3-d]pyrimidin-7-yl]-ethanol

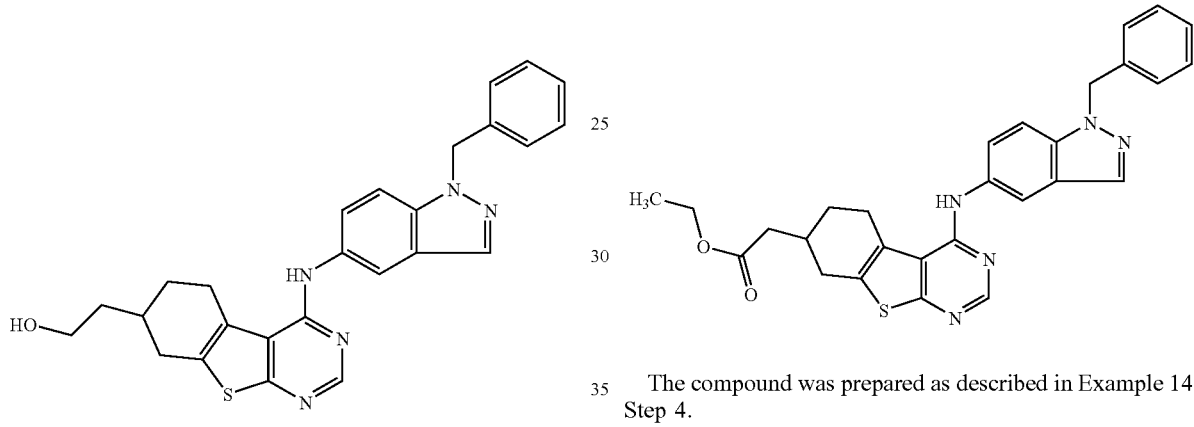

Step 1. Preparation of Example 203: 1-Benzyl-1H-indazol-5-ylamine

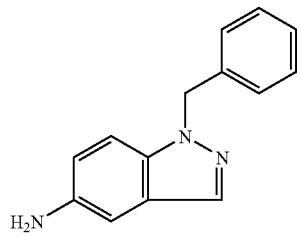

To a solution of 5-nitroindazole (10.0 g, 61.3 mmol) in acetonitrile (100 mL) was added potassium carbonate (16.9 g, 122.6 mmol) and benzyl bromide (13.6 g, 79.7 mmol). The resulting yellow reaction mixture was heated with stirring at 70° C. overnight. Upon cooling down, the solid was filtered off and washed with methylene chloride. The filtrate was concentrated to dryness and the resulting residue was purified by flash chromatography eluting with 17–25% ethyl acetate in hexanes (v/v) yielding 7.0 g (44%) of the corresponding 1-Benzyl-5-nitro-1H-indazole as a yellow solid.

7.61 g (136 mmol, 5 equiv) of Iron powder (4.03 g, 72.1 mmol) was added slowly to the solution of 1-Benzyl-5-nitro-1H-indazole (6.9 g, 27.2 mmol) in acetic acid (200 mL). After stirring at room temperature overnight, the reaction mixture became milky with formation of a white precipitate. The precipitate was filtered off and the filtrate was concentrated to ca. 20 mL. The residue was diluted with water (200 mL) and neutralized by slow addition of sodium hydroxide. The mixture was then extracted with ethyl acetate (500×5 mL). The organic layer were combined, dried over sodium sulfate, filtered and concentrated to dryness to afford 1-benzyl-1H-indazol-5-ylamine (5.23 g, 82%) as a brown solid. $^1$H NMR (DMSO-d$_6$): δ 7.72 (s, 1H), 7.35 (d, J=8.8 Hz, 1H), 7.24–7.14 (m, 5H), 6.74 (m, 2H), 5.49 (s, 2H), 4.80 (br, 2H). ES-LCMS: RT=0.93 min; [M+H]$^+$=224.2.

Step 2. Preparation of Example 203: [4-(1-Benzyl-1H-indazol-5-ylamino)-5,6,7,8-tetrahydro-benzo[4,5]thieno[2,3-d]pyrimidin-7-yl]-acetic acid ethyl ester

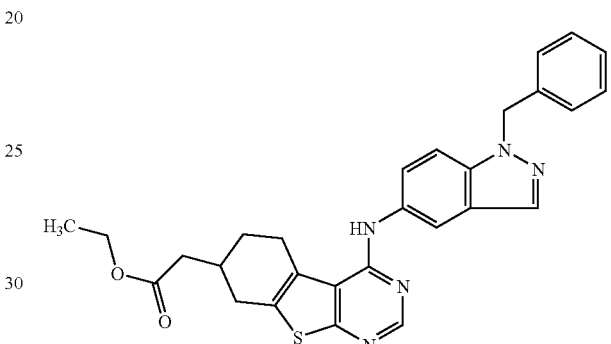

The compound was prepared as described in Example 14, Step 4.

$^1$H-NMR (DMSO-d$_6$) δ 8.76 (s, 1H), 8.41 (s, 1H), 8.15 (s, 1H), 7.98 (d, J=2.6 Hz, 1H), 7.75 (d, J=8.9 Hz, 1H), 7.52 (dd, J=8.9, 2.0 Hz, 1 H), 7.24–7.24 (m, 5H), 5.68 (s, 2H), 4.12 (q, J=7.1 Hz, 2H), 3.22 (m, 2H), 3.02 (dd, J=17.0. 4.7 Hz, 1H), 2.63–2.45 (m, 3H), 2.28 (m, 1H), 2.01 (d, J=13.7 Hz, 1H), 1.58 (m, 1H), 1.21 (t, J=7.1 Hz, 3H). LCMS RT=3.34 min; [M+H]$^+$=498.3.

Step 3. Preparation of Example 203: 2-[4-(1-Benzyl-1H-indazol-5-ylamino)-5,6,7,8-tetrahydro-benzo[4,5]thieno[2,3-d]pyrimidin-7-yl]-ethanol

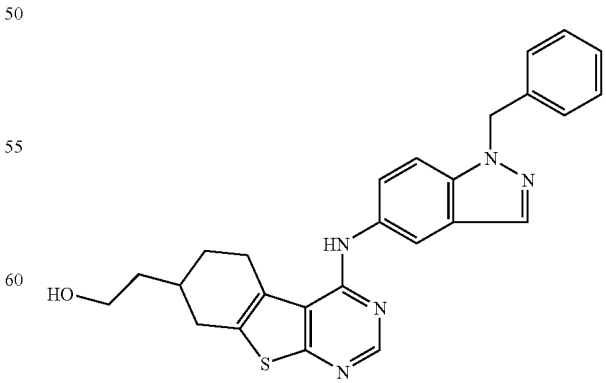

To a solution of THF (100 mL) was added 4.50 g (9.04 mmol, 1 equiv) of [4-(1-Benzyl-1H-indazol-5-ylamino)-5, 6,7,8-tetrahydro-benzo[4,5]thieno[2,3-d]pyrimidin-7-yl]-acetic acid ethyl ester. A 1M solution of diisobutylaluminum hydride in THF (45.2 mL, 45.2 mmol, 5 equiv) was added to the solution at 0° C. and the reaction was stirred for 30 min before warming up to rt and stirring for 2 h. The reaction mixture was quenched with Rochelle's salt followed by EtOAc. The solution was separated and the aqueous layer discarded and the organic layer was washed with brine (200 mL) and water (100 mL). The resulting crude material was purified by flash chromatography eluting with 95/5 $CH_2Cl_2$/MeOH yielding 850 mg (21%) of Example 203 as a white solid. $^1$H-NMR ($CD_2Cl_2$) δ 8.36 (s, 1H), 8.08 (d, J=1.8 Hz, 1H), 8.01 (s, 1H), 7.46–7.19 (m, 8H), 5.60 (s, 2H), 3.77 (q, J=4.4 Hz, 2H), 3.21–2.96 (m, 3H), 2.56 (m, 1H), 2.11 (m, 2H), 1.67 (m, 3H), 1.45 (t, J=4.4 Hz, 1H). LCMS RT=2.68 min; [M+H]$^+$=456.3.

EXAMPLE 214

Preparation of 2-{4-[3-Methyl-4-(6-methyl-pyridin-3-yloxy)-phenylamino]-5,6,7,8-tetrahydro-benzo[4,5]thieno[2,3-d]pyrimidin-7-yl}-ethanol

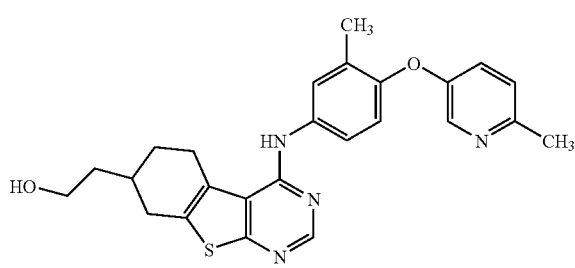

Step 1. Preparation of Example 214: 3-Methyl-4-(6-methyl-pyridin-3-yloxy)-phenylamine

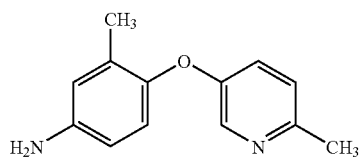

To a DMF suspension (60 mL) of sodium hydride (1.39 g, 60% in mineral oil) was slowly added a DMF solution (40 mL) of 5-hydroxy-2-methylpyridine (3.80 g, 34.8 mmol) dropwise, keeping the temp <5° C. The ice bath was removed, and the contents allowed to warm with stirring for 60 min. To the light yellow colored contents was added a DMF solution of 2-fluoro-5-nitrotoluene (4.50 g, 29.0 mmol) dropwise, and the contents heated to 95° C., overnight. The dark brown contents were removed from heating, and allowed to cool to rt with stirring. The mixture was quenched with water (5 mL), and concentrated in vacuo. The residue was diluted with water (100 mL) and EtOAc (75 mL). The layers were separated, and the aq. layer extracted with EtOAc (2×75 mL). The combined organic layers were washed with brine (2×50 mL), dried over MgSO4, filtered and concentrated in vacuo to collect the 2-Methyl-5-(2-methyl-4-nitro-phenoxy)pyridine as a yellow oil (7.0 g, 94%).

The solution of 2-Methyl-5-(2-methyl-4-nitro-phenoxy)-pyridine (6.4 g, 26.2 mmol), 10 wt % Pd/C (0.50 g) in ethanol (100 mL) was stirred under 1 atm hydrogen at rt for 24 h. Then the Pd/C catalyst was removed by filtration through a layer of celite. Removal of the solvent gave the desired product as an off-white solid (5.55 g, 99%). $^1$H-NMR (DMSO-d6) δ 8.04 (d, J=2.7 Hz, 1H), 7.13 (d, J=5.4 Hz, 1H), 7.02 (dd, J=8.7, 3.1 Hz, 1H), 6.68 (d, J=8.7 Hz, 1H), 6.49 (d, J=2.6 Hz, 1H), 6.42 (dd, J=8.4, 2.8 Hz, 1H), 4.96 (br, 2H), 2.39 (s, 3H), 1.97 (s, 3H). LCMS RT=1.04 min; [M+H]$^+$=215.2.

Step 2. Preparation of Example 214: {4-[3-Methyl-4-(6-methyl-pyridin-3-yloxy)-phenylamino]-5,6,7,8-tetrahydro-benzo[4,5]thieno[2,3-d]pyrimidin-7-yl}-acetic acid ethyl ester

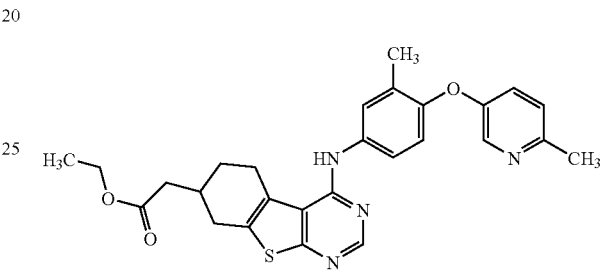

The compound was prepared as described in Example 14, Step 4.

$^1$H-NMR (CDCl$_3$) δ 8.49 (s, 1H), 8.26 (d, J=1.7 Hz, 1 H), 7.52 (s, 1H), 7.47 (dd, J=8.5, 2.6 Hz, 1H), 7.16–7.05 (m, 3H), 6.91 (d, J 8.5 Hz, 1H), 4.18 (q, J=7.2 Hz, 2H), 3.14–3.04 (m, 3H), 2.60 (m, 1H), 2.53 (d, J=2.0 Hz, 3H), 2.46 (s, 3H), 2.27 (s, 3H), 2.17 (m, 1H), 1.71 (m, 1H), 1.30 (q, J=7.2 Hz, 3H). LCMS RT=2.52 min; [M+H]$^+$=489.4.

Step 3. Preparation of Example 214: 2-{4-[3-Methyl-4-(6-methyl-pyridin-3-yloxy) -phenylamino]-5,6,7,8-tetrahydro-benzo[4,5]thieno[2,3-d]pyrimidin-7-yl}-ethanol

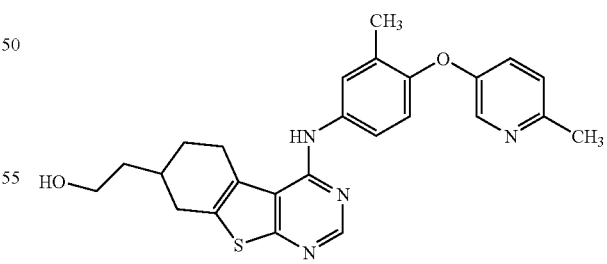

The compound was prepared as described in Example 203, Step 3.

$^1$H-NMR (CD$_2$Cl$_2$) δ 8.40 (s, 1H), 8.20 (dd, J=2.6, 1.0 Hz, 1H), 7.52 (m, 2H), 7.11 (m, 3H), 6.91 (d, J=8.5 Hz, 1H), 3.76 (q, J=4.2 Hz, 2H), 3.17–2.94 (m, 3H), 2.55 (m, 1H), 2.48 (s, 3H), 2.25 (s, 3H), 2.11 (m, 2H), 1.98 (t, J=4.2 Hz, 1H), 1.88–1.74 (m, 1H). LCMS RT=2.21 min; [M+H]$^+$=447.2.

EXAMPLE 235

Preparation of {7-[2-(2,5-Dimethyl-pyrrolidin-1-yl)-ethyl]-5,6,7,8-tetrahydro-benzo[4,5]thieno[2,3-d]pyrimidin-4-yl}-[3-methyl-4-(6-methyl-pyridin-3-yloxy)-phenylamine

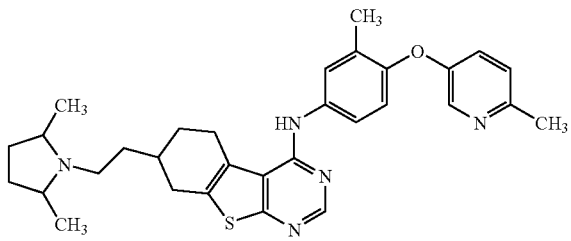

Step 1. Preparation of Example 235: Methanesulfonic acid 2-{4-[3-methyl-4-(6-methyl-pyridin-3-yloxy)-phenylamino]-5,6,7,8-tetrahydro-benzo[4,5]thieno[2,3-d]pyrimidin-7-yl}-ethyl ester

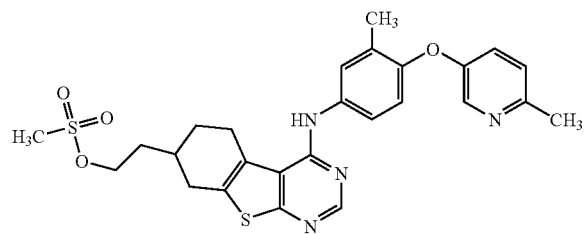

To the suspension of Example 214 (2.18 g 4.9 mmol) in acetonitrile (55 mL) containing pyridine (1.27 g, 16.1 mmol) at 0° C. was added methyl sulfonic anhydride (1.53 g, 8.8 mmol) in several portions. Then the reaction mixture was stirred at rt overnight until no Example 214 was left. The reaction mixture was poured into ethyl acetate/brine (400 mL/150 mL). The organic layer after extraction was washed with saturated sodium carbonate, water in sequence, dried over sodium sulfate, concentrated to get the product (2.44 g, 90%) as a yellow foamy solid. $^1$H-NMR (CD$_2$Cl$_2$) δ 8.41 (s, 1H), 8.20 (s, 1H), 7.52 (m, 2H), 7.10 (m, 3H), 6.89 (d, J=8.5, 1H), 4.37 (t, J=6.4 Hz, 2H), 3.20–2.98 (m, 3H), 3.02 (s, 3H), 2.59 (m, 1H), 2.48 (s, 3H), 2.26 (s, 3H), 2.15 (br, 2H), 1.90 (m, 2H), 1.68 (m, 1H). LCMS RT=2.90 min; [M+H]$^+$=525.2.

Step 2. Preparation of {7-[2-(2,5-Dimethyl-pyrrolidin-1-yl)-ethyl]-5,6,7,8-tetrahydro-benzo[4,5]thieno[2,3-d]pyrimidin-4-yl}-[3-methyl-4-(6-methyl-pyridin-3-yloxy)-phenyl]-amine

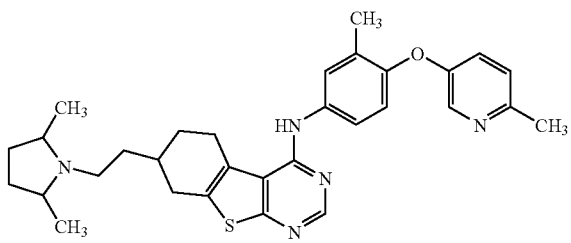

The compound was prepared as described in Example 177. $^1$H-NMR (CD$_2$Cl$_2$) δ 8.40 (s, 1H), 8.19 (d, J=2.4, 0.9 Hz, 1H), 7.54–7.50 (m, 2H), 7.12–7.08 (m, 3H), 6.90 (d, J=8.5 Hz, 1H), 3.16–2.92 (m, 4H), 2.76–2.54 (m, 4H), 2.47 (s, 3H), 2.24 (s, 3H), 2.12 (br, 1H), 1.95 (m, 2H), 1.79 (m, 1H), 1.66–1.53 (m, 3H), 1.37–1.32 (m, 2H), 1.06 (d, J=6.1 Hz, 3H), 0.95 (d, J=6.3 Hz, 3H). LCMS RT=1.97 min; [M+H]$^+$=528.3.

Using the method described above and the appropriate starting materials, Examples 213–227, 230–234, and 236 were similarly prepared.

EXAMPLE 239

Preparation of (1-Benzyl-1H-indazol-5-yl)-[7-(2-piperidine-1-yl-ethyl)-5,6,7,8-tetrahydro-benzo[4,5]thieno[2,3-d]pyrimidin-4-yl]-amine

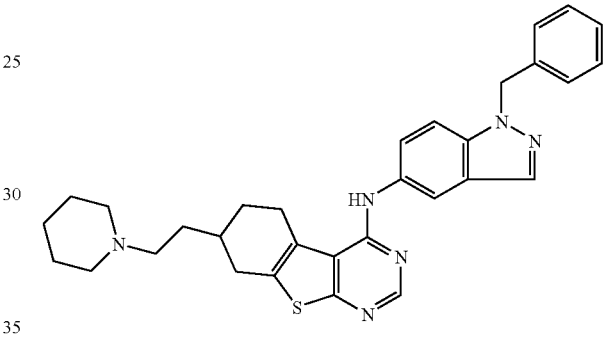

Step 1. Preparation of Example 239: Methanesulfonic acid 2-[4-(1-benzyl-1H-indazol-5-ylamino)-5,6,7,8-tetrahydro-benzo[4,5]thieno[2,3-d]pyrimidin-7-yl]-ethyl ester

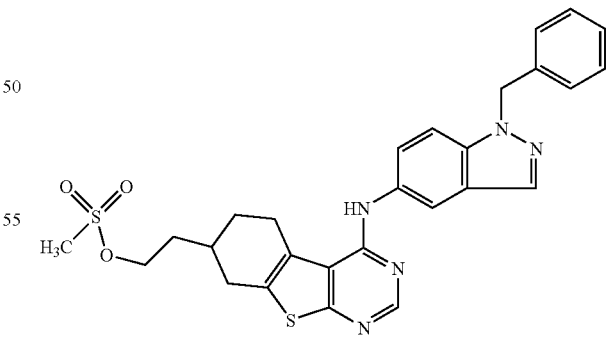

The compound was prepared as described in Example 235, Step 1.

$^1$H-NMR (CD$_2$Cl$_2$) δ 8.37 (s, 1H), 8.08 (d, J=1.8 Hz, 1H), 8.02 (d, J=1.0 Hz, 1H), 7.47–7.16 (m, 8H), 5.60 (s, 2H), 4.37 (t, J=6.4 Hz, 2H), 3.18–2.98 (m, 3H), 3.02 (s, 3H), 2.58 (m, 1H), 2.15 (br, 2H), 1.90 (m, 2H), 1.68 (m, 1H). LCMS RT=3.02 min; [M+H]$^+$=534.2.

Step 2. Preparation of (1-Benzyl-1H-indazol-5-yl)[7-(2-piperidin-1-yl-ethyl)-5,6,7,8-tetrahydro-benzo[4,5]thieno[2,3-d]pyrimidin-4-yl]-amine

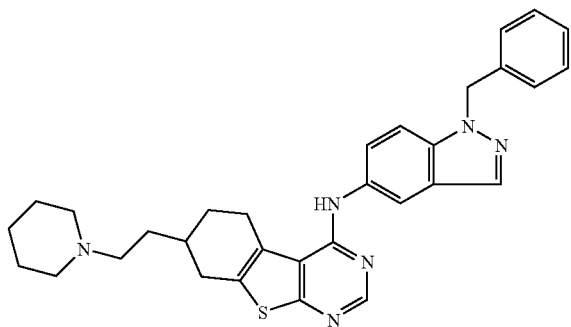

The compound was prepared as described in Example 177. ¹H-NMR (CD₂Cl₂) δ 8.35 (s, 1H), 8.07 (d, J=1.8 Hz, 1H), 8.00 (s, 1H), 7.42–7.27 (m, 5H), 7.21 (d, J=1.8 Hz, 1H), 7.16 (d, J=4.7 Hz, 2H), 5.58 (s, 2H), 3.18–2.90 (m, 3H), 2.56–2.47 (m, 1H), 2.44–2.33 (m, 5H), 2.08–1.95 (m, 3H), 1.64–1.50 (m, 7H), 1.41 (m, 2H). LCMS RT=2.47 min; [M+H]⁺=523.4.

Using the method described above and the appropriate starting materials, Examples 202–212, 227–229, and 237–238 were similarly prepared.

EXAMPLE 242

Preparation of N4-(3-chloro-4-fluorophenyl)-N7-(2-morpholin-4-ylethyl)-5,6,7,8-tetrahydro[1]benzothieno[2,3-d]pyrimidine-4,7-diamine

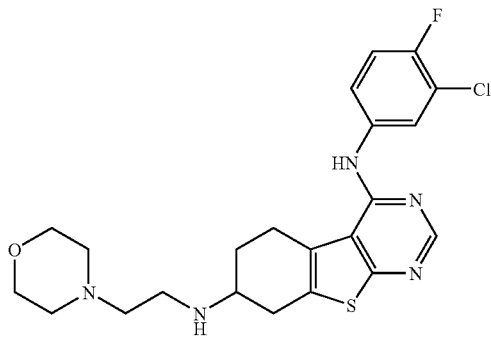

Step 1. Preparation of Ethyl 2-amino-4,7-dihydro-5H-spiro[1-benzothiophene-6,2'-[1,3]dioxolane]-3-carboxylate

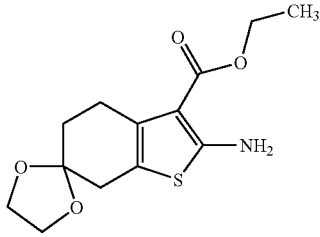

To 600 mL ethanol were sequentially 1,4-Dioxa-spiro[4,5]decan-8-one (25.0 g, 0.160 mol), ethyl cyanoacetate (18.1 g, 0.160 mol), morpholine (14.0 g, 0.160 mol), and sulfur (5.5 g, 0.160 mol). The heterogeneous contents were stirred at room temperature for 4 days, after which time all the sulfur had dissolved. The homogenous contents were concentrated under reduced pressure, and the residue diluted with ethyl acetate (200 mL). The mixture was washed with water (200 mL), and the layers separated. The organic layer was dried over MgSO₄, filtered, and concentrated under reduced pressure to afford the desired product as a dark colored oil (45.0 g, 99%). ¹H-NMR (DMSO-d₆) δ 7.20 (s, 2H), 4.10 (q, 2H), 3.87 (s, 4H), 2.66 (t, 2H), 2.59 (s, 2H), 1.71 (t, 2H), 1.18 (t, 3H); LCMS RT=2.58 min; [M+H]⁺=284.2.

Step 2. Preparation of 3,5,6,8-tetrahydro-4H-spiro[1-benzothieno[2,3-d]pyrimidine-7,2'-[1,3]dioxolan]-4-one

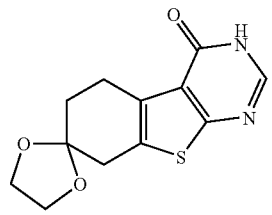

To a stirring 225 mL formamide solution of ethyl 2-amino-4,7-dihydro-5H-spiro[1-benzothiophene-6,2'-[1,3]dioxolane]-3-carboxylate (40.0 g, 0.142 mol) was added ammonium formate (17.8 g, 0.282 mol). The contents were stirred with heating at 140° C. for 16 h, after which time the heterogeneous contents were removed from heating, and allowed to cool to rt. The contents were filtered, the solid filter cake washed with water (2×60 mL), and suction dried overnight to afford the desired product as an off-white solid (33.0 g, 88%). ¹H-NMR (DMSO-d₆) δ 12.35 (broad s, 1H), 8.00 (s, 1H), 3.92 (s, 4H), 2.95 (t, 2H), 2.91 (s, 2H), 1.83 (t, 2H); LCMS RT=1.87 min; [M+H]⁺=265.2.

Step 3. Preparation of 4-chloro-5,8-dihydro-6H-spiro[1-benzothieno[2,3-d]pyrimidine-7,2'-[1,3]dioxolane]

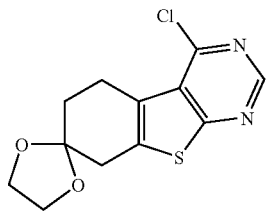

To a stirring 0° C. POCl₃ (200 mL) solution of 3,5,6,8-tetrahydro-4H-spiro[1-benzothieno[2,3-d]pyrimidine-7,2'-[1,3]dioxolan]-4-one (20.0 g, 0.076 mol) was added triethylamine (200 mL) from a dropping funnel over a 15 min. period. The contents were allowed to warm to rt, and then heated to 80° C. After 3 h, the contents were removed from heating, and allowed to cool to rt. The heterogeneous mixture was concentrated under reduced pressure, the residue diluted with ethyl acetate (100 mL), and again concentrated. The residue was diluted with ethyl acetate (100 mL) and the heterogeneous mixture poured onto a stirring mixture of ice-water/sq. NaHCO$_3$ (800 mL). After 5 min. stirring, the now pH=7 contents were filtered and the solid filter cake washed with water. The product was dried in vacuum oven overnight to afford the desired product (20.7 g, 97%) as an off-white solid. $^1$H-NMR (DMSO-d$_6$) δ 8.82 (s, 1H), 3.97 (s, 4H), 3.10 (t, 2H), 3.07 (s, 2H), 1.95 (t, 2H); LCMS RT=2.45 min; [M+H]$^+$=283.1.

Step 4. Preparation of N-(3chloro-4-fluorophenyl)-5,8-dihydro-6H-spiro[1-benzothieno[2,3-d]pyrimidine-7,2'-[1,3]dioxolan]-4-amine:

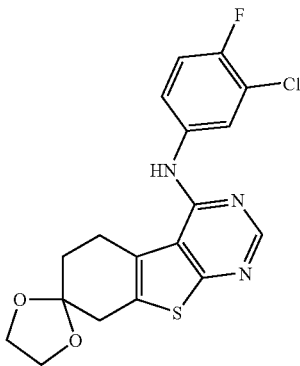

To a stirring ethanol solution (100 mL) of 4-chloro-5,8-dihydro-6H-spiro[1-benzothieno[2,3-d]pyrimidine-7,2'-[1,3]dioxolane] (7.0 g, 24.8 mmol) was added 4-fluoro-3-chloroaniline (3.6 g, 24.8 mmol) and 0.05 mL 4N HCl (in dioxane). The contents were heated to reflux for 5 h, after which time the contents were removed from heating and allowed to cool to rt. The solvent was removed under reduced pressure, the crude residue suspended in aq. NaHCO$_3$ (100 mL), and stirred for 15 min. The contents were again filtered, and the solid filter cake washed with water. The collected yellow solid was triturated with diethyl ether (50 mL) to afford the final product (5.5 g, 57%) as a light yellow solid. $^1$H-NMR (DMSO-d$_6$) δ 8.41 (s, 1H), 8.28 (s, 1H), 7.78 (dd, 1H), 7.58 (m, 1H), 7.35 (t, 1H), 3.97 (s, 4H), 3.22 (t, 2H), 3.00 (s, 2H), 1.93 (t, 2H); LCMS RT=3.26 min; [M+H]$^+$=392.3.

Step 5. Preparation of 4-(3Chloro-4-fluoro-phenylamino)-5,8-dihydro-6H-benzo[4,5]thieno[2,3-d]pyrimidin-7-one

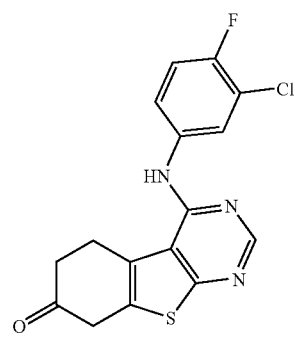

To a stirring acetic acid/water solution (4:1, 300 mL) was added N-(3-chloro-4-fluorophenyl)-5,8-dihydro-6H-spiro [1-benzothieno[2,3-d]pyrimidine-7,2'-[1,3]dioxolan]-4-amine (5.5 g, 14 mmol), and the contents heated at 80° C. for 12 h. The dark colored mixture was cooled to rt, and the solvent removed under reduced pressure. The crude residue was suspended in 1N NaHCO$_3$ (100 mL), stirred for 10 min., and filtered. The filtered solid was triturated with diethyl ether (100 mL) to afford the desired product (4.8 g, 98%) as a dark yellow solid. $^1$H-NMR (DMSO-d$_6$) δ 8.53 (s, 1H), 8.46 (s, 1H), 7.87 (dd, 1H), 7.60 (m, 1H), 7.40 (t, 1H), 3.73 (s, 2H), 3.43 (t, 2H), 2.64 (s, 2H); LCMS RT=3.01 min; [M+H]$^+$=348.2.

Step 6. Preparation of N4-(3-chloro-4-fluorophenyl)-N7-(2-morpholin-4-ylethyl)-5,6,7,8-tetrahydro [1]benzothieno[2,3-d]pyrimidine-4,7-diamine

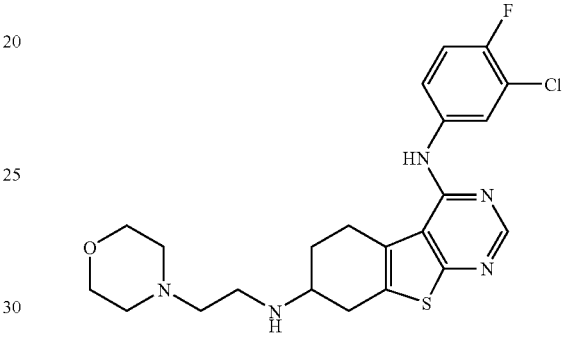

To a stirring DCE/THF solution (1:1, 16 mL) of 4-(3-chloro-4-fluoro-phenylamino)-5,8-dihydro-6H-benzo[4,5] thieno[2,3-d]pyrimidin-7-one (150 mg, 0.43 mmol) was added 1-N-(2-aminoethyl)morphine (62 mg, 0.47 mmol), sodium triacetoxyborohydride (137 mg, 0.65 mmol), and 2 drops of acetic acid. The contents were stirred at rt for 3 h, after which time the stirring was halted and the solvent removed under reduced pressure. The residue was diluted with ethyl acetate (5 mL) and washed with water (5 mL). The organic layer was separated, dried over Na$_2$SO$_4$, filtered, and concentrated under reduced pressure. The crude product was purified by reverse phase HPLC to afford the desired product (30 mg, 15%). $^1$H-NMR (DMSO-d$_6$) δ 8.40 (s, 1H), 7.82 (dd, 1H), 7.50 (m, 1H), 7.23 (t, 1H), 3.94 (t, 4H), 3.80 (m, 1H), 3.66 (t, 2H), 3.49 (t, 2H), 3.37 (m, 1H), 3.29–3.35 (m, 6H), 3.06 (m, 1H), 2.48 (m, 1H), 2.07 (m, 1H); LCMS RT=1.89 min; [M+H]$^+$=462.1.

Using the method described above and the appropriate starting materials, Examples 240–243 were similarly prepared.

Compositions Useful for the Method of this Invention

A compound of Formula I is useful in this method for treating the conditions described further herein when it is formulated as a pharmaceutically acceptable composition. A pharmaceutically acceptable composition is a compound of Formula I in admixture with a pharmaceutically acceptable carrier. A pharmaceutically acceptable carrier is any carrier that is relatively non-toxic and innocuous to a patient at concentrations consistent with effective activity of the active ingredient so that any side effects ascribable to the carrier do not vitiate the beneficial effects of the active ingredient.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$);

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate);

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono-or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures);

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

The compounds of the present invention can be administered with pharmaceutically-acceptable carriers well known in the art using any effective conventional dosage unit forms formulated as immediate, slow or timed release preparations, including, for example, the following.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238–311; Strickley, R. G "Parenteral Formulations of Small Molecule Therapeutics Marketed in the United States (1999)-Part-1" *PDA Journal of Pharmaceutical Science & Technology* 1999, 53(6), 324–349; and Nema, S. et al, "Excipients and Their Use in Injectable Products" *PDA Journal of Pharmaceutical Science & Technology* 1997, 51(4), 166–171.

It is believed that one skilled in the art, utilizing the preceding information, can utilize the present invention to its fullest extent. Nevertheless, the following are examples of pharmaceutical formulations that can be used in the method of the present invention. They are for illustrative purposes only, and are not to be construed as limiting the invention in any way.

Pharmaceutical compositions according to the present invention can be further illustrated as follows:

Sterile IV Solution: A 5 mg/mL solution of the desired compound of this invention is made using sterile, injectable water, and the pH is adjusted if necessary. The solution is diluted for administration to 1–2 mg/mL with sterile 5% dextrose and is administered as an IV infusion over 60 min.

Lyophilized powder for IV administration: A sterile preparation can be prepared with (i) 100–1000 mg of the desired compound of this invention as a lypholized powder, (ii) 32–327 mg/mL sodium citrate, and (iii) 300–3000 mg Dextran 40. The formulation is reconstituted with sterile, injectable saline or dextrose 5% to a concentration of 10 to 20 mg/mL, which is further diluted with saline or dextrose 5% to 0.2–0.4 mg/mL, and is administered either IV bolus or by IV infusion over 15–60 min.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Cancer

The compounds and compositions described herein can be used to treat or prevent hyper-proliferative disorders. An effective amount of a compound or composition of this invention can be administered to a patient in need thereof in order to achieve a desired pharmacological effect. A patient, for the purpose of this invention, is a mammal, including a human, in need of treatment (including prophylactic treatment) for a particular disorder described further herein. A pharmaceutically effective amount of compound or composition is that amount which produces a desired result or exerts an influence on the particular hyper-proliferative disorder being treated.

Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The disorders described above have been well characterized in humans, but also exist with a similar etiology in other mammals. Accordingly, the method of this invention can be administered to mammals, including humans, in need thereof for the treatment of angiogenesis and/or proliferative dependent disorders.

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528–35), taxotere (Bissery et al. *Anti Cancer Drugs* 1995, 6(3), 339), and topoisomerase inhibitors (Edelman et al. *Cancer Chemother. Pharmacol.* 1996, 37(5), 385–93) were demonstrated with the use of in vitro tumor proliferation assays.

The compounds and compositions described herein, including salts and esters thereof, exhibit anti-proliferative activity and are thus useful to prevent or treat the disorders associated with hyper-proliferation. The following assay is one of the methods by which compound activity relating to treatment of the disorders identified herein can be determined.

In vitro Tumor Cell Proliferation Assay

The tumor cell proliferation assay used to test the compounds of the present invention involves a readout called Cell Titer-Glow® Luminescent Cell Viability Assay developed by Promega (Cunningham, B A "A Growing Issue: Cell Proliferation Assays, Modern kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 81–88), that measures inhibition of cell proliferation. Generation of a luminescent signal corresponds to the amount of ATP present, which is directly proportional to the number of metabolically active (proliferating) cells.

A431cells (human epidermoid carcinoma, ATCC # HTB-20) and BT474 (human breast carcinoma, ATCC # CRL-1555) were plated at a density of $2.5 \times 10^3$ cells/well in 96 well black-clear bottom tissue culture plates in RPMI media with 10% Fetal Bovine Serum and incubated at 37° C. Twenty-four hours later, test compounds are added at a final concentration range from as high 100 μM to as low 64 pM depend on the activities of the tested compounds in serial dilutions at a final DMSO concentration of 0.1%. Cells were incubated for 72 hours at 37° C. in complete growth media after addition of the test compound. After 72 hours of drug exposure, the plates were equilibrated to room temperature for approximately 30 min. Then, using a Promega Cell Titer Glo Luminescent® assay kit, lysis buffer containing 100 microliters of the enzyme luciferase and its substrate, luciferin mixture, was added to each well. The plates were mixed for 2 min on orbital shaker to ensure cell lysis and incubated for 10 min at room temperature to stabilize luminescence signal. The samples were read on VICTOR 2 using Luminescence protocol, and analyzed with Analyze5 software to generate IC50 values. Representative compounds of this invention showed inhibition of tumor cell proliferation in this assay.

For determination of IC50's, a linear regression analysis can be used to determine drug concentration which results in a 50% inhibition of cell proliferation using this assay format. The anti-proliferative activities of selective sets of compounds are listed below. In A431 cells, Examples 4, 15, 22, 26, 45, 54–55, 58–62, 66, 70, 72–75, 77–80, 82–88, 92–94, 96–98, 105, 139–142, 145, 148, 150, 152–154, 152–165, 167–171, 175–179, 183–186, 189–198, 200, 202–203, 205–212, 221–224, and 230 have IC50's below 5 µM; whereas Examples 1–3, 8, 12, 16, 20, 23, 24, 31, 32, 39, 40, 42, 46, 48, 49, 52, 56, 57, 63–65, 67–69, 71, 76, 81, 89, 90, 91, 95, 99–103, 136–138, 143–146, 147, 149, 151, 155, 156, 166, 172–174, 180–182, 187, 188, 199, 201, 204, 213–220, 225–229, 231–239 have IC50's below 50 µM. In BT474 cells, Examples 2, 4, 15, 22, 36, 39, 42, 43, 45, 45, 48, 54, 58–60, 62, 66, 67, 73–75, 77–80, 82, 84, 85–88, 92–99, 101, 103, 105, 136–143, 148, 150, 152–200, 202–212, 214–239 have IC50's below 5 µM; whereas Examples 1, 3, 8, 12, 16, 20, 23, 24, 31, 32, 40, 49, 52, 55–57, 61, 63–65, 68–72, 76, 81, 83, 89–91, 100, 102, 144, 146, 147, 149, 151, 201, 213 have $IC_{50}$'s below 50 µM.

Based upon the above and other standard laboratory techniques known to evaluate compounds useful for the prevention and/or treatment of the diseases or disorders described above by standard toxicity tests and by standard pharmacological assays for the determination of the prevention and/or treatment of the conditions identified above in mammals, and by comparison of these results with the results of known medicaments that are used to treat these conditions, the effective dosage of the compounds of this invention can readily be determined for prevention and/or treatment of each desired indication. The amount of the active ingredient to be administered in the prevention and/or treatment of one of these conditions can vary widely according to such considerations as the particular compound and dosage unit employed, the mode of administration, the duration of treatment (including prophylactic treatment), the age and sex of the patient treated, and the nature and extent of the condition to be prevented and/or treated.

The total amount of the active ingredient to be administered will generally range from about 0.001 mg/kg to about 300 mg/kg, and preferably from about 0.10 mg/kg to about 150 mg/kg body weight per day. A unit dosage may contain from about 0.5 mg to about 1500 mg of active ingredient, and can be administered one or more times per day. The daily dosage for administration by injection, including intravenous, intramuscular, subcutaneous and parenteral injections, and use of infusion techniques will preferably be from 0.01 to 200 mg/kg of total body weight. The daily rectal dosage regimen will preferably be from 0.01 to 200 mg/kg of total body weight. The daily vaginal dosage regimen will preferably be from 0.01 to 200 mg/kg of total body weight. The daily topical dosage regimen will preferably be from 0.1 to 200 mg administered between one to four times daily. The transdermal concentration will preferably be that required to maintain a daily dose of from 0.01 to 200 mg/kg. The daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of administration and number of doses of a compound or composition of the present invention or a pharmaceutically acceptable salt or ester thereof can be ascertained by those skilled in the art using conventional prevention and/or treatment tests.

The compounds of this invention can be administered as the sole pharmaceutical agent or in combination with one or more other pharmaceutical agents where the combination causes no unacceptable adverse effects. For example, the compounds of this invention can be combined with other anti-hyper-proliferative or other indication agents, and the like, as well as with admixtures and combinations thereof.

For example, optional anti-hyper-proliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment and/or prevention of neoplastic diseases in *Goodman and Gilman's The Pharmacological Basis of Therapeutics* (Ninth Edition), editor Molinoff et al., publ. by McGraw-Hill, pages 1225–1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of this invention include but are not limited to other anti-cancer agents such as epothilone, irinotecan, raloxifen and topotecan.

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein.

What is claimed is:

1. A compound of formula

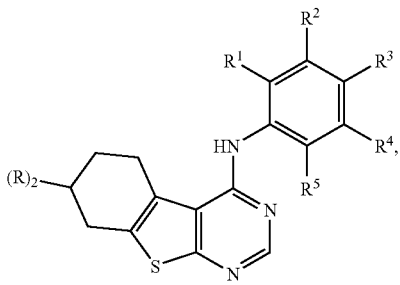

wherein

R is in each instance selected independently from H, $(C_2–C_6)$alkenyl, $C(O)R^6$, hydroxy, $NR^{8-1}R^{8-1}$, and

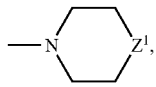

or

R is $(C_1–C_6)$alkyl said alkyl being optionally monosubstituted with $R^7$,
with the proviso that when one R is H, the other R must be other than H or methyl, and with the further proviso that when one R is hydroxy, the other R must be other than hydroxy;

$R^1$ is selected from H, OH, halo, CN, $NH_2$, $CF_3$, $OCF_3$, $(C_1–C_3)$alkyl, $(C_2–C_3)$alkynyl, and $(C_1–C_3)$alkoxy;

$R^2$ is selected from H, OH, halo, $NH_2$, CN, $CF_3$, $OCF_3$, $(C_1–C_3)$alkyl, $(C_2–C_6)$alkynyl, $(C_1–C_3)$alkoxy, $(C_1–C_3)$alkoxy-phenyl where said phenyl is optionally substituted with 1, 2 or 3 substituents each selected independently from $(C_1–C_3)$alkyl, $(C_1–C_3)$alkoxy, halo, $CF_3$, CN, and OH, and $(C_1–C_3)$alkoxy-pyridyl, where said pyridyl is optionally substituted with 1, 2 or 3 substituents each selected independently from $(C_1–C_3)$alkyl, $(C_1–C_3)$alkoxy, halo, $CF_3$, CN, and OH, O-phenyl optionally substituted with 1, 2 or 3 substituents each selected independently from $(C_1–C_3)$alkyl, $(C_1–C_3)$alkoxy, halo, $CF_3$, CN, and OH;

O-pyridyl optionally substituted with 1, 2 or 3 substituents each selected independently from $(C_1–C_3)$alkyl, $(C_1–C_3)$alkoxy, halo, $CF_3$, CN, and OH;

$R^3$ is selected from H, OH, halo, $NH_2$, CN, $CF_3$, $OCF_3$, $(C_1–C_3)$alkyl, $(C_2–C_6)$alkynyl, $(C_1–C_3)$alkoxy, $(C_1–C_3)$alkoxy-phenyl where said phenyl is optionally substituted with 1, 2 or 3 substituents each selected independently from $(C_1–C_3)$alkyl, $(C_1–C_3)$alkoxy, halo, $CF_3$, CN, and OH, and $(C_1–C_3)$alkoxy-pyridyl, where said pyridyl is optionally substituted with 1, 2 or 3 substituents each selected independently from $(C_1–C_3)$alkyl, $(C_1–C_3)$alkoxy, halo, $CF_3$, CN, and OH, O-phenyl optionally substituted with 1, 2 or 3 substituents each selected independently from $(C_1–C_3)$alkyl, $(C_1–C_3)$alkoxy, halo, $CF_3$, CN, and OH;

O-pyridyl optionally substituted with 1, 2 or 3 substituents each selected independently from $(C_1–C_3)$alkyl, $(C_1–C_3)$alkoxy, halo, $CF_3$, CN, and OH;

or $R^2$ and $R^3$ together with the carbon atoms to which they are attached form a pyrazole, where said pyrazole is optionally substituted with 1 or 2 substituents each selected independently from methyl, ethyl and benzyl or pyridylmethyl, wherein benzyl and pyridylmethyl can optionally be substituted with 1 or 2 substituents each selected independently from methyl, halo, cyano and methoxy;

$R^4$ is selected from H, OH, halo, CN, $CF_3$, $OCF_3$, $NH_2$, $(C_1–C_3)$alkyl, $(C_2–C_6)$alkynyl, $(C_1–C_3)$alkoxy, trifluoromethyl, trifluoromethoxy, $(C_1–C_3)$alkoxy-phenyl where said phenyl is optionally substituted with 1, 2 or 3 substituents each selected independently from $(C_1–C_3)$alkyl, $(C_1–C_3)$alkoxy, halo, $CF_3$, CN, and OH, and $(C_1–C_3)$alkoxy-pyridyl, where said pyridyl is optionally substituted with 1, 2 or 3 substituents each selected independently from $(C_1–C_3)$alkyl, $(C_1–C_3)$alkoxy, halo, $CF_3$, CN, and OH, O-phenyl optionally substituted with 1, 2 or 3 substituents each selected independently from $(C_1–C_3)$alkyl, $(C_1–C_3)$alkoxy, halo, $CF_3$, CN, and OH;

O-pyridyl optionally substituted with 1, 2 or 3 substituents each selected independently from $(C_1–C_3)$alkyl, $(C_1–C_3)$alkoxy, halo, $CF_3$, CN, and OH;

or $R^5$ is selected from H, OH, halo, CN, $CF_3$, $OCF_3$, $NH_2$, $(C_1–C_3)$alkyl, $(C_2–C_3)$alkynyl, and $(C_1–C_3)$alkoxy;

$R^6$ is selected from OH, $(C_1–C_6)$alkyl, $(C_1–C_3)$alkoxy, phenyl, pyridyl, $NR^8R^8$,

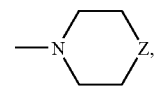

$NH(C_2–C_6)$alkenyl, and
a five membered heterocycle optionally substituted with a substituent selected from OH, $N[(C_1–C_3)$alkyl$]_2$, and $(C_1–C_3)$alkyl, said alkyl being optionally substituted with a substituent selected from OH, $(C_1–C_3)$alkoxy, and

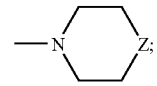

$R^7$ is selected from OH, halo, $(C_1–C_4)$alkoxy, phenoxy optionally substituted with halo or amino, $C(O)R^6$, halo, $NR^8R^8$, imidazolyl, phenyl, indazolyl, aminoindazolyl, $—OS(O)_2(C_1–C_3)$,

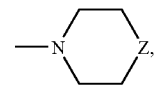

$NHC(O)NR^8R^8$, $NHS(O)_2R^9$, NHC(O)-pyrrolidinyl, NHC(O)-morpholinyl, and pyrrolidinyl optionally substituted with one or two substituents selected from hydroxy, $(C_1-C_3)$alkoxy, $N[(C_1-C_3)$alkyl$]_2$, and $(C_1-C_3)$alkyl optionally mono-substituted with hydroxy or $(C_1-C_3)$alkoxy;

$R^8$ is in each instance selected independently from H, pyridyl,
  $(C_1-C_4)$alkyl optionally mono-substituted with hydroxy, $(C_1-C_3)$alkoxy, $-S(O)_2(C_1-C_3)$alkyl, $NR^{10}R^{10}$, or

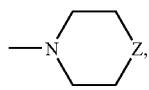

and
  phenyl optionally substituted with 1, 2, or 3 substituents each independently selected from CN, OH, halo, $CF_3$, $NR^{10}R^{10}$ and $(C_1-C_3)$alkoxy, or $R^8$ is

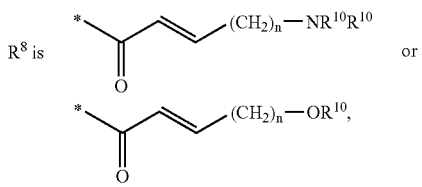

or wherein n is a number from 1 to 5 and $R^{10}$ is selected from H and $(C_1-C_3)$alkyl;

$R^{8-1}$ is in each instance selected independently from H, and
  $(C_1-C_4)$alkyl optionally mono-substituted with $(C_1-C_3)$alkoxy, $NR^{10}R^{10}$, or

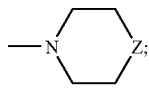

$R^9$ is selected from $(C_1-C_3)$alkyl, pyridyl, thienyl, and phenyl where said phenyl is optionally substituted with 1, 2, or 3 substituents each independently selected from $(C_1-C_3)$alkyl, $(C_1-C_3)$alkoxy, CN, OH, halo, $CF_3$, and $NR^8R^8$;

$R^{10}$ is selected from H and $(C_1-C_3)$alkyl;

Z is selected from $CH_2$, O, S, SO, $SO_2$, and NH, and when Z is NH, H is optionally replaced with pyridyl,
  $(C_1-C_3)$alkyl optionally substituted with a substituent selected from hydroxy, $(C_1-C_3)$alkoxy and pyridyl, or
  phenyl optionally substituted with 1, 2, or 3 substituents each independently selected from $(C_1-C_3)$alkyl, $(C_1-C_3)$alkoxy, CN, halo, $CF_3$, and $NR^8R^8$;

$Z^1$ is selected from $CH_2$, O, S, SO, $SO_2$, and NH, and when $Z^1$ is NH, H is optionally replaced with pyridyl,
  $(C_1-C_3)$alkyl optionally substituted with a substituent selected from hydroxy, $(C_1-C_3)$alkoxy and pyridyl, or
  phenyl optionally substituted with 1, 2, or 3 substituents each independently selected from $(C_1-C_3)$alkyl, $(C_1-C_3)$alkoxy, CN, halo, $CF_3$, and $NR^8R^8$;

or a pharmaceutically acceptable salt or ester thereof, excluding the following compounds:

5,6,7,8-tetrahydro-7-methyl-N-[4-(phenylmethoxy)phenyl]-[1]benzothieno-[2,3-d]pyrimidin-4-amine, monohydrochloride;

5,6,7,8-tetrahydro-N-(4-methoxyphenyl)-7-methyl-[1]benzothieno[2,3-]pyrimidin-4-amine, monohydrochloride;

5,6,7,8-tetrahydro-7-methyl-N-[3-(trifluoromethyl)phenyl]-[1]benzothieno-[2,3-d]pyrimidin-4-amine;

N-(3,4-dimethylphenyl)-5,6,7,8-tetrahydro-7-methyl [1]benzothieno-[2,3-d]pyrimidin-4-amine.

2. The compound of claim 1, wherein

R is selected independently from hydrogen and $C(O)R^6$, or

R is $(C_1-C_6)$alkyl said alkyl being optionally mono-substituted with $R^7$;

with the proviso that when one R is H, the other R must be other than H or methyl;

$R^1$ is selected from H, OH, halo, CN, $NH_2$, $CF_3$, methyl, ethyl, ethynyl, methoxy, and ethoxy;

$R^2$ is selected from H, OH, halo, $NH_2$, CN, $CF_3$, $(C_1-C_3)$alkyl, $(C_2-C_6)$alkynyl, $(C_1-C_3)$alkoxy,
  $(C_1-C_3)$alkoxy-phenyl where said phenyl is optionally substituted with 1, 2 or 3 substituents each selected independently from $(C_1-C_3)$alkyl, $(C_1-C_3)$alkoxy, halo, $CF_3$, CN, and OH, and
  $(C_1-C_3)$alkoxy-pyridyl, where said pyridyl is optionally substituted with 1, 2 or 3 substituents each selected independently from $(C_1-C_3)$alkyl, $(C_1-C_3)$alkoxy, halo, $CF_3$, CN, and OH,
  O-phenyl optionally substituted with 1, 2 or 3 substituents each selected independently from $(C_1-C_3)$alkyl, $(C_1-C_3)$alkoxy, halo, $CF_3$, CN, and OH;

$R^3$ is selected from H, OH, halo, $NH_2$, CN, $CF_3$, $(C_1-C_3)$alkyl, $(C_2-C_6)$alkynyl, $(C_1-C_3)$alkoxy,
  $(C_1-C_3)$alkoxy-phenyl where said phenyl is optionally substituted with 1, 2 or 3 substituents each selected independently from $(C_1-C_3)$alkyl, $(C_1-C_3)$alkoxy, halo, $CF_3$, CN, and OH,
  $(C_1-C_3)$alkoxy-pyridyl, where said pyridyl is optionally substituted with 1, 2 or 3 substituents each selected independently from $(C_1-C_3)$alkyl, $(C_1-C_3)$alkoxy, halo, $CF_3$, CN, and OH,
  O-phenyl optionally substituted with 1, 2 or 3 substituents each selected independently from $(C_1-C_3)$alkyl, $(C_1-C_3)$alkoxy, halo, $CF_3$, CN, and OH,
  O-pyridyl optionally substituted with 1, 2 or 3 substituents each selected independently from $(C_1-C_3)$alkyl, $(C_1-C_3)$alkoxy, halo, $CF_3$, CN, and OH; or $R^2$ and $R^3$ together with the carbon atoms to which they are attached form a pyrazole, where said pyrazole is optionally N-substituted with 1 substituent selected from methyl, ethyl and benzyl;

$R^4$ is H;

$R^5$ is H;

$R^5$ is selected from $NR^8R^8$,

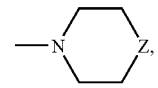

$NH(C_2-C_6)$alkenyl, and a five membered heterocycle optionally substituted with a substituent selected from OH, $N[(C_1-C_3)$ alkyl]$_2$, and (C$_1$–C$_3$)alkyl, said alkyl being optionally substituted with a substituent selected from OH, (C$_1$–C$_3$)alkoxy, and

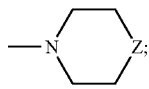

R$^7$ is selected from phenoxy optionally substituted with halo or amino, NR$^8$R$^8$, imidazolyl, indazolyl, aminoindazolyl,

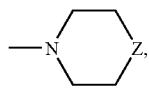

NHC(O)NR$^8$R$^8$, NHS(O)$_2$R$^9$, NHC(O)-pyrrolidinyl, NHC(O)-morpholinyl, and
pyrrolidinyl optionally substituted with one substituent selected from (C$_1$–C$_3$)alkoxy, N[(C$_1$–C$_3$)alkyl]$_2$, and (C$_1$–C$_3$)alkyl optionally mono-substituted with (C$_1$–C$_3$)alkoxy;

R$^8$ is in each instance selected independently from H, pyridyl,
(C$_1$–C$_4$)alkyl optionally mono-substituted with (C$_1$–C$_3$)alkoxy, —S(O(C$_1$–C$_3$)alkyl, NR$^{10}$R$^{10}$, or

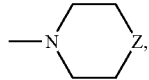

and
phenyl optionally substituted with 1, 2, or 3 substituents each independently selected from CN, OH, halo, CF$_3$, NR$^{10}$R$^{10}$ and (C$_1$–C$_3$)alkoxy;

R$^9$ is selected from (C$_1$–C$_3$)alkyl, pyridyl, thienyl, and phenyl where said phenyl is optionally substituted with 1, 2, or 3 substituents each independently selected from (C$_1$–C$_3$)alkyl, (C$_1$–C$_3$)alkoxy, CN, OH, halo, CF$_3$, and NR$^8$R$^8$;

R$^{10}$ is selected from H and (C$_1$–C$_3$)alkyl;

Z is selected from CH$_2$, O, S and NH, and
when Z is NH, H is optionally replaced with pyridyl,
(C$_1$–C$_3$)alkyl optionally substituted with a substituent selected from hydroxy, (C$_1$–C$_3$)alkoxy and pyridyl, or
phenyl optionally substituted with 1, 2, or 3 substituents each independently selected from (C$_1$–C$_3$) alkyl, (C$_1$–C$_3$)alkoxy, CN, halo, CF$_3$, and NR$^8$R$^8$;

or a pharmaceutically acceptable salt or ester thereof, excluding the following compounds:
5,6,7,8-tetrahydro-7-methyl-N-[4-phenylmethoxy)phenyl]-[1]benzothieno-[2,3-d]pyrimidin-4-amine, monohydrochloride;
5,6,7,8-tetrahydro-N-(4-methoxyphenyl)-7-methyl-[1]benzothieno[2,3-d]pyrimidin-4-amine, monohydrochloride;
5,6,7,8-tetrahydro-7-methyl-N-[3-(trifluoromethyl)phenyl]-[1]benzothieno-[2,3-d]pyrimidin-4-amine;
N-(3,4-dimethylphenyl)-5,6,7,8-tetrahydro-7-methyl [1]benzothieno-[2,3-d]pyrimidin-4-amine.

3. A process for preparing a compound according to claim 1, wherein a compound of formula (II)

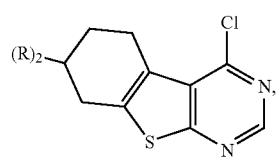

(II)

wherein R has the meaning indicated in claim 1,
is reacted with a compound of formula (III)

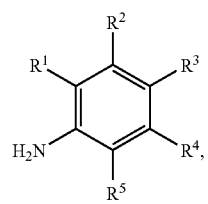

(III)

wherein R$^1$ to R$^5$ have the meaning indicated in claim 1.

4. A pharmaceutical composition comprising a compound according to claim 1.

5. A pharmaceutical composition comprising a compound of claim 1 in combination with at least one pharmaceutically acceptable, pharmaceutically safe carrier or excipient.

6. A process for preparing a pharmaceutical composition according to claim 5, comprising combining at least one compound according to claim 1 with at least one pharmaceutically acceptable, pharmaceutically safe carrier or excipient.

7. A method of treating lung or breast cancer in a mammal comprising administering to a mammal in need thereof an effective amount of a compound of formula (I).

* * * * *